(12) United States Patent
Stoloff et al.

(10) Patent No.: US 10,765,734 B2
(45) Date of Patent: *Sep. 8, 2020

(54) INFLUENZA PEPTIDES AND COMPOSITIONS

(71) Applicant: PepTcell limited, London (GB)

(72) Inventors: Gregory A. Stoloff, London (GB); Wilson Romero Caparros-Wanderley, Buckinghamshire (GB)

(73) Assignee: PepTcell Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/295,488

(22) Filed: Mar. 7, 2019

(65) Prior Publication Data

US 2019/0201519 A1    Jul. 4, 2019

Related U.S. Application Data

(63) Continuation of application No. 15/865,214, filed on Jan. 8, 2018, now Pat. No. 10,279,032, which is a continuation of application No. 15/231,347, filed on Aug. 8, 2016, now Pat. No. 9,889,191, which is a continuation of application No. 13/906,232, filed on May 30, 2013, now Pat. No. 9,446,116, which is a continuation of application No. 12/278,728, filed as application No. PCT/GB2007/000383 on Feb. 5, 2007, now Pat. No. 8,475,802.

(30) Foreign Application Priority Data

Feb. 7, 2006  (GB) .................................. 0602416.0
Jul. 13, 2006  (GB) .................................. 0613977.8

(51) Int. Cl.
| | | |
|---|---|---|
| *A61K 39/145* | (2006.01) | |
| *A61K 39/12* | (2006.01) | |
| *C07K 14/005* | (2006.01) | |
| *C07K 7/08* | (2006.01) | |
| *C07K 14/11* | (2006.01) | |
| *A61K 39/00* | (2006.01) | |

(52) U.S. Cl.
CPC ............ *A61K 39/145* (2013.01); *A61K 39/12* (2013.01); *C07K 7/08* (2013.01); *C07K 14/005* (2013.01); *C07K 14/11* (2013.01); *A61K 2039/55566* (2013.01); *A61K 2039/57* (2013.01); *A61K 2039/572* (2013.01); *A61K 2039/70* (2013.01); *C12N 2760/16122* (2013.01); *C12N 2760/16134* (2013.01); *C12N 2760/16171* (2013.01); *C12N 2760/16222* (2013.01); *C12N 2760/16234* (2013.01); *C12N 2760/16271* (2013.01)

(58) Field of Classification Search
None
See application file for complete search history.

(56) References Cited

U.S. PATENT DOCUMENTS

| | | | |
|---|---|---|---|
| 5,741,493 A | * | 4/1998 | Moste-Deshairs ......................... A61K 39/145 424/184.1 |
| 6,740,325 B1 | | 5/2004 | Arnon et al. |
| 6,939,546 B2 | | 9/2005 | Nauss et al. |
| 8,444,995 B2 | | 5/2013 | Soloff et al. |
| 8,475,802 B2 | | 7/2013 | Stoloff et al. |
| 9,446,116 B2 | | 9/2016 | Stoloff et al. |
| 9,889,191 B2 | | 2/2018 | Stoloff et al. |
| 2004/0087521 A1 | | 5/2004 | Donnelly et al. |
| 2004/0223976 A1 | | 11/2004 | Bianchi et al. |
| 2004/0247612 A1 | | 12/2004 | Wang et al. |
| 2004/0265987 A1 | | 12/2004 | Trager et al. |
| 2005/0002954 A1 | | 1/2005 | Arnon et al. |
| 2005/0009008 A1 | | 1/2005 | Robinson et al. |
| 2005/0250933 A1 | | 11/2005 | Binz et al. |
| 2006/0024670 A1 | | 2/2006 | Luke et al. |
| 2007/0122430 A1 | | 5/2007 | Shneider et al. |
| 2010/0047275 A1 | | 2/2010 | Stoloff et al. |
| 2012/0219575 A1 | | 8/2012 | Stoloff et al. |

FOREIGN PATENT DOCUMENTS

| | | |
|---|---|---|
| EP | 1991563 B1 | 11/2008 |
| WO | 1988008852 A1 | 11/1988 |
| WO | 1993020846 A1 | 10/1993 |
| WO | 1994003205 A1 | 2/1994 |
| WO | 1994026903 A1 | 11/1994 |
| WO | WO/96/10631 * | 10/1995 |
| WO | 1996010631 A1 | 4/1996 |
| WO | 2002024876 A2 | 3/2002 |
| WO | 2002026252 A1 | 4/2002 |

(Continued)

OTHER PUBLICATIONS

GenBank Accession P13880, Matrix protein 1, Jan. 2006.*
GenBank Accession AAX56544, nucleocapsid protein [Influenza A virus (A/New York/149/1999(H3N2))], Apr. 2005.*
GenBank Accession AF100361, nucleoprotein (Influenza B virus), May 1999.*
GenBank Accession AAZ43413, polymerase PB1 [Influenza A virus (A/Memphis/59/1999(H3N2))]., Aug. 2005.*
Gen Bank Accession AF255369, membrane ion channel M2 [Influenza A virus (A/Hong Kong/497/97(H3N2))], Sep. 2004.*
U.S. Appl. No. 12/278,728, filed May 26, 2009, US 2010/0047275, U.S. Pat. No. 8,475,802.

(Continued)

*Primary Examiner* — Benjamin P Blumel
(74) *Attorney, Agent, or Firm* — UltimatEdge IP Law Group, P.C.; Dean G. Stathakis

(57) ABSTRACT

The present specification discloses recombinant nucleic acid constructs encoding an immunogenic multiepitope polypeptide comprising two or more polypeptides, recombinant nucleic acid constructs encoding at least two epitopes from two or more internal proteins of influenza virus, compositions comprising such recombinant nucleic acid constructs and methods of eliciting a T cell immune response against an influenza virus in a vertebrate using such recombinant nucleic acid constructs and compositions.

26 Claims, 5 Drawing Sheets

Specification includes a Sequence Listing.

(56) References Cited

FOREIGN PATENT DOCUMENTS

| WO | 2004080403 A3 | 9/2004 |
| WO | 2005099752 A2 | 10/2005 |
| WO | 2005116270 A2 | 12/2005 |
| WO | 2005120564 A2 | 12/2005 |
| WO | 2006116082 A1 | 11/2006 |
| WO | 2007091030 A2 | 8/2007 |
| WO | 2007092792 A2 | 8/2007 |

OTHER PUBLICATIONS

U.S. Appl. No. 13/465,940, filed May 7, 2012, US 2012/0219575, U.S. Pat. No. 8,444,995.
U.S. Appl. No. 13/906,232, filed May 30, 2013, US 2013/0243804, U.S. Pat. No. 9,446,116.
U.S. Appl. No. 15/231,347, filed Aug. 8, 2016, US 2017/0028053, U.S. Pat. No. 9.889,191.
U.S. Appl. No. 15/865,214, filed Jan. 8, 2018, US 20180147277, U.S. Pat. No. 10,279,032.
U.S. Appl. No. 15/876,781, filed Jan. 22, 2018, US 20180185470, U.S. Pat. No. 10,335,480.
U.S. Appl. No. 16/540,811, filed Aug. 14, 2019.
Aichele, et al., T cell priming versus T cell tolerance induced by synthetic peptides, J. Exp. Med., 182(1); 261-266 (1995).
Alexander, et al., Functional CTL Repertoire and Recognition of Human A11-Restricted CTL Epitopes, J. Immunol. 159(10): 4753-4761 (1997).
Altuvia, et al., Ranking potential binding peptides to MHC molecules by a computational threading approach, J. Mol. Biol. 249:244-250 (1995).
Altuvia, et al., A structure-based algorithm to predict potential binding peptides to MHC molecules with hydrophobic binding pockets, Hum. Immunol. 58: 1-11 (1997).
Anderson, et al., Poor correspondence between predicted and experimental binding of peptides to class I MHC molecules, Tissue Antigens 55: 519-531 (2000).
Bastin, et al., Use of synthetic peptides of influenza nucleoprotein to define epitopes recognized by class I-restricted cytotoxic T lymphocytes, J. Exper. Med. 165(6): 1508-1523 (1987).
Belz, et al., Diversity of epitope and cytokine profiles for primary and secondary influenza A virus-specific CD8+ T cell responses, J. Immunol. 167(3): 4627-4633 (2001).
Bender, et al., Transgenic mice lacking class I major histocompatibility complex-restricted T cells have delayed viral clearance and increased mortality after influenza virus challenge, J. Exper. Med. 175: 1143-1145 (1992).
Ben-Yedidia, et al., Towards an Epitope-Based Human Vaccine for Influenza, Hum. Vaccines 1(3): 95-101 (2005).
Berkhoff, et al., A Mutation in the HLA-B*705-Restricted NP383-391 Epitope Affects the Human Influenza A Virus-Specific Cytotoxic T-Lymphocyte Response In Vitro, J. Virol. 78(10): 5216-5222 (2004).
Berkhoff, et al., Functional Constraints of Influenza A Virus Epitopes Limit Escape from Cytotoxic T Lymphocytes, J. Virol. 79(17): 11239-11246 (2005).
Bernhard, et al., Cytotoxic T lymphocytes from HLA-A2 transgenic mice specific for HLA-A2 expressed on human cells, J. Exp. Med., 168: 1157-1162 (1988).
Bodmer, et al., Class I cross-restricted T cells reveal low responder allele due to processing of viral antigen, Nature, 337(6208): 653-655 (1989).
Boon, et al., The Magnitude and Specificity of Influenza A Virus-Specific Cytotoxic T-Lymphocyte Responses in Humans Is Related to HLA-A and -B Phenotype, J. Virol. 76: 582-590 (2002).
Boon, et al., Recognition of homo- and heterosubtypic variants of influenza A viruses by human CD8+ T lymphocytes, J. Immunol. 172(4): 2453-2460 (2004).
Boon, et al., Functional profile of human influenza virus-specific cytotoxic T lymphocyte activity is influenced by Interleukin-2 concentration and epitope specificity, Clin. Exp. Immunol. 142: 45-52 (2005).
Brander, et al., Definition of an optimal cytotoxic T lymphocyte Epitope in the latently expressed Kaposi's Sarcoma-Associated Herpesvirus Kaposin Protein, J. Infect. Dis. 184: 119-126 (2001).
Caparros-Wanderley, et al., Intratype sequence variation among clinical isolates of the human papillomavirus type 6 L1 ORF: Clustering of mutations and identification of a frequent amino acid sequence variant, J. Gen.I Virol. 80 (4): 1025-1033 (1999).
Castrucci, et al., Genetic Reassortment between Avian and Human influenza A Viruses in Italian Pigs, Virol. 193 (1): 503-506 (1993).
Castrucci, et al., EMBL-EBI Submission, Accession No. Q67194, Matrix Protein, fragment, Influenza A virus (A/swine/Italy/526/1985(H3N2)) (1996).
Chen, et al., Naturally processed peptides longer than nine amino acid residues bind to the class I MHC molecule HLA-A2.1 with high affinity and in different conformations, J. Immunol. 152: 2874-2881 (1994).
Chenna, et al., Multiple sequence alignment with the Clustal series of programs, Nucleic Acids Res. 31(13): 3497-3500 (2003).
Cheuk, et al., Human MHC class I transgenic mice deficient for H2 class I expression facilitate identification and characterization of new HLA class-I-restricted viral T cell epitopes, J. Immunol. 169: 5571-5580 (2002).
Cheuk, et al., Strong memory CD8+ T cell responses against immunodominant and three new subdominant HLA-B27-restricted influenza A CTL epitopes following secondary infection of HLA-B27 transgenic mice, Cell. Immunol. 234 (2): 110-123 (2005).
Chi et al., Molecular evolution of human influenza A/H3N2 virus in Asia and Europe from 2001 to 2003, J. Clin. Microbiol. 43(12): 6130-6132 (2005).
Cole, et al., Efficient priming of CD8+ memory T cells specific for a subdominant epitope following Sendai virus Infection, J. Immunol. (1997), 158: 4301-4309 (1997).
Conti, et al., Expression and Secretion of RANTES by Human Peripheral Blood CD4+ Cells are Dependent on the Presence of Monocytes, Ann. Clin. Lab. Sci. 31(1): 75-84 (2001).
De Jong, et al., Influenza Virus: a Master of Metamorphosis, J. Infect. 40: 218-228 (2000).
Deavin, et al., Statistical comparison of established T-cell epitope predictors against a large database of human and murine antigens, Mol. Immunol. 33(2): 145-155 (1996).
Deliyannis, et al., Induction of long-term memory CD8+ T cells for recall of viral clearing responses against influenza virus, J. Virol. 76(9): 4212-4221 (2002).
Donnelly, et al., Further protection against antigenic drift of influenza virus in a ferret model by DNA vaccination, Vaccine 15(8): 865-868 (1997).
Dorrell, et al., Recombinant modified vaccinia virus Ankara efficiently restimulates human cytotoxic T lymphocytes in vitro, Vaccine 19(2-3): 327-336 (2000) (Abstract only).
Elliott, et al., Peptide-induced conformational change of the class I heavy chain, Nature, 351: 402-407 (1991).
The European Medicine Agency Evaluation of Medicines for Human Use (EMEA), Guideline on Adjuvants in Vaccines for Human Use, pp. 18 (2005).
EPO, Extended European Search Report, European Application No. 11157383.8 (dated Apr. 18, 2012).
EPO, Extended European Search Report, European Application No. 11157382.0 (dated Apr. 26, 2012).
EPO, Extended European Search Report, European Application No. 17180723 (dated Sep. 22, 2017).
Epstein, et al., Vaccination with DNA encoding internal proteins of influenza virus does not require CD8+ cytotoxic T lymphocytes: either CD4+ or CD8+ T cells can promote survival and recovery after challenge, Int. Immunol. 12(1): 91-101 (2000).
Epstein, et al., DNA Vaccine Expressing Conserved Influenza Virus Proteins Protective against H5N1 Challenge Infection in Mice, Emer. Infect. Dis. 8(8): 796-801 (2002).
Falk, et al., Allele-specific motifs revealed by sequencing of self-peptides eluted from MHC molecules, Nature 351: 290-297 (1991).

(56) References Cited

OTHER PUBLICATIONS

Falsey, et al., Respiratory syncytial virus and influenza A infections in the hospitalized elderly, J. Infect. Dis. 172(2): 389-394 (1995).
Flower, et al., Towards in silica prediction of immunogenic epitopes, TRENDS Immunol. 24(12): 667-674 (2003).
Gahery-Segard, et al., Long-term specific immune responses induced in humans by a human immunodeficiency virus type I lipopeptide vaccine: characterization of CD8+-T-cell epitopes recognized, J. Virol. (2003) 77(20): 11220-11231 (2003).
Gao, et al., Effect of a single amino acid change in MHC class I molecules on the rate of progression to AIDS, N. Engl. J. Med. 344(22): 1668-1675 (2001).
Gerdil, et al., The annual production cycle for influenza vaccine, Vaccine, 21(16): 1776-1779 (2003).
Gianfrani, et al., Human memory CTL response specific for influenza A virus is broad and multispecific, Hum. Immunol. 61(5): 438-452 (2000).
Gileadi, U. et al., Generation of an Immunodominant CTL Epitope is Affected Proteasome Subunit Composition and Stability of the Antigenic Protein, J. Immunol. 163: 6045-6052 (1999).
Gotch, et al., Cytotoxic T lymphocytes recognize a fragment of influenza virus matrix protein in association with HLA-A2., Nature, 326: 881-882 (1987).
Graham, et al., Resistance to and recovery from lethal influenza virus infection in B lymphocyte-deficient mice, J. Exp. Med. 186(12): 2063-2068 (1997).
Greenspan, et al., Defining epitopes: Its not as easy at it seems, Nat. Biotech. 17: 936-937 (1999).
Gregory, et al., Emergence of Influenza A H1N2 Reassortant Viruses in the Human Population during 2001, Virology 300(1): 1-7 (2002).
Guan, et al., Emergence of Avian H1N1 Influenza Viruses in Pigs in China, J. Virol. 70(11): 8041-8046 (1996).
Guan, et al., MHCPred: a server for quantitative prediction of peptide-MHC binding, Nucl. Acids Res. 31(13): 3621-3624 (2003).
Gulukota, et al., Two complementary methods for predicting peptides binding major histocompatibility complex molecules, J. Mol. Biol., 267(5): 1258-1267 (1997).
Guo, et al., Different length peptides bind to HLA-Aw68 similarly at their ends but bulge out in the middle, Nature 360: 364-367 (1992).
Hall, Variation in nucleotide sequences coding for the N-terminal regions of the Matrix and non-structural proteins of Influenza A Viruses, J. Virol. 38(1): 1-7 (1981).
Haste-Andersen, et al., Prediction of residues in discontinuous B-cell epitopes using protein 3D structures, Protein Sci. 15(11): 2558-2567 (2006).
Haywood, et al., Pharmaceutical excipients—where do we begin? Aust. Prescriber 34(4): 112-114 (2011).
Hiromoto, et al., Evolutionary characterization of the six internal genes of H5N1 human influenza A virus, J. Gen. Virol. 81(5): 1293-1303 (2000).
Hopp, et al., Prediction of protein antigenic determinants from aminco acids sequences, Proc. Natl. Acad. Sci., USA 78: 3824-3828 (1981).
Hu, et al., Highly conserved pattern of recognition of influenza A wild-type and variant CD+ CTL epitopes in HLA-A2+ humans and transgenic HLA-A2+/H2 class I deficient mice, Vaccine 23(45): 5231-5244 (2005).
Hunt, et al., Characterization of peptides bound to the class I MHC molecule HLA-A2.1 by mass spectrometry, Science 255: 1261-1263 (1992).
Immune Epitope Database & Analysis Resource (IEDB), Table from Immune Eitope Database showing infuenza A epitopes citations (Feb. 6, 2006).
IPEC, The IPEC Excipient Composition Guide, pp. 11 (2009).
Jameson, et al., Human CD8+ and CD4+ T lymphocyte memory to influenza A virus s of swine and avian species, J. Immunol. 162(12): 7578-7583 (1999).
Jameson, et al., Human Cytotoxic T-Lymphocyte Repertoire to Influenza A Viruses, J. Virol. 72(11): 8682-8689 (1998).
Janeway, et al., Immunobiology: The Immune System in Health and Disease, Appendix I, Immunologist's Toolboc, pp. 42 (5th ed., New York: Garland Science, 2001).
Kast, et al. Protection against lethal Sendai virus infection by in vivo priming of virus-specific cytotoxic T lymphocytes with a free synthetic peptide, Proc. Natl. Acad. Sci. USA 88(6): 2283-2287 (1991).
Kawaoka, et al., Avian-to-human transmission of the PB1 gene of influenza A viruses in the 1957 and 1968 pandemics, J. Virol. 63: 4603-4608 (1989).
Kulkarni-Kale, et al., CEP: a conformational epitope prediction server, Nucleic Acids Res., 33: W168-W171 (2005).
Kuwano, et al., Active immunization against virus infections due to antigenic drift by induction of crossreactive cytotoxic T lymphocytes, J. Exp. Med. 169: 1361-1371 (1989).
Laver, et al. Antigenic drift in type A influenza virus: peptide mapping and antigenic analysis of A/PR/8/34 (H1N1) variants selected with monoclonal antibodies, Proc. Natl. Acad. Sci. USA 76(3): 1425-1429 (1979).
Lawrence, et al., Frequency, Specificity, and Sites of Expansion of CD8+ T Cells during Primary Pulmonary Influenza Virus Infection, J. Immunol. 174: 5332-5340 (2005).
Le, A-XT, et al., Cytotoxic T cell responses in HLA-A2.1 transgenic mice, J. Immunol. 142: 1366-1371 (1989).
Levy, French economic evaluation of influenza and influenza vaccination, PharmacoEconomic 9(Suppl. 3): 62-66 (1996).
Li, GenBank Submission, Accession No. AAG22554, Matrix protein, partial, Inflenza A virus (A/Denver/1957)(2007).
Macken, et al., "The value of a database in surveillance and vaccine selection," in Options for the Control of Influenza IV. A.D.M.E. Osterhaus, N. Cox and A.W. Hampson (Eds.), Amsterdam, Elsevier Science, (2001), pp. 103-106, Influenza Sequence Database (ISD).
Mallios, et al., Predicting class II MHC/peptide multi-level binding with an iterative stepwise discriminant analysis meta-algorithm, Bioinformatics 17: 942-948 (2001).
Man et al. Definition of a human T cell epitope from influenza A non-structual protein 1 usin gHLA-A2.1 transgenic mice, Int. Immunol. 597-605 (1995).
Meister, et al., Two novel T cell epitope prediction algorithms based on MHC-binding motifs comparison of predicted and published epitopes from Mycobacterium tuberculosis and HIV protein sequences, Vaccine 13: 581-591 (1995).
Moss, et al., "Antigenic drift in the hemagglutinin from various strains of influenza virus A/Hong-Kong/68 (H3N2)," p. 329, in: Laver, W.G., Air, G.M. (Eds.), Structure and Variation in Influenza Virus (Elsevier/North Holland, Amsterdam, The Netherlands, 1980).
Murphy, et al., "Orthomyxoviruses, In Fields." Virology, 3rd Edition, (1996), pp. 1397-1445, Edited by B.N. Fields, D. M. Knipe & P.M. I lolwy, Philadelphia: Lippincott-Raven.
Nehete, et al., Protection against chronic infection and AIDS by an HIV envelope peptide-cocktail vaccine in a pathogenic SHIV-rhesus model, Vaccine 20(5-6): 813-825 (2001).
Nerome, et al., Genetic analysis of porcine H3N2 viruses originating in southern China, J. Gen. Virol. 76: 613-624 (1995).
Nicholson, et al., Textbook of Influenza, Chapters 21 and 24, (1998).
Nicholson, et al., Table titled "Known Influenza Virus Antigenic Peptides Listed by . . . " as an excerpt from Chapter 24, Textbook of Influenza (1998).
Nielsen, et al. Improved prediction of MHC class I and class II epitopes using a novel Gibbs sampling approach, Bioinfo. 20(9): 1388-1397 (2004).
Nielsen, et al., NetMHCpan, a method for quantitative predictions of peptide binding to any HLA-A and -B locus protein of known sequence, PLoS one 2: e796-e805 (2007).
Nielsen, et al., Prediction of MHC class II binding affinity using SMM-align, a novel stabilization matrix alignment method, BMC Bioinfo. 8: 238-249 (2007).
Nijman, et al., Identification of peptide sequences that potentially trigger HLA-A2.1-restricted cytotoxic T lymphocytes, Eur. J. Immunol. 23(6): 1215-1219 (1993) (Abstract only).

(56) References Cited

OTHER PUBLICATIONS

Oukka, et al., Protection against lethal viral infection by vaccination with nonimmunodominat peptides, J. Immunol. 157(7): 3039-3045 (1996).
Pamer, et al., Precise prediction of a dominant class I MHC-restricted epitope of Listeria monocytogenes, Nature, 353(6347): 852-855 (1991).
Parham, Deconstructing the MHC, Nature, (1992), 360: 300-301 (1992).
Parker, et al., Sequence motifs important for peptide binding to the human MHC class I molecule HLA-A2, J. Immunol. 149(11): 3580-3587 (1992)(Abstract only).
Parker, et al., Scheme for ranking potential HLA-A2 binding peptides based on independent binding of individual peptide side-chains, J. Immunol. 152: 163-175 (1994).
PCT Form IB 373, International Preliminary Report on Patentability, PCT/GB2007/000383, pp. 11 (dated Aug. 12, 2008).
Peachman, et al., Human dendritic cells and macrophages exhibit different intracellular processing pathways for soluble and liposome-encapsulated antigens, Immunobiol. 210(5): 321-333 (2005).
Peters, et al., A community resource benchmarking predictions of peptide binding to MHC-I molecules, PLoS Comput. Biol., 2(6)e65: 574-584 (2006).
Price, et al., Viral escape by selection of cytotoxic T-cell-resistant variants in influenza A virus pneumonia, J. Exp. Med. 191(11): 1853-1868 (2000).
Rammensee, et al., MHC ligands and peptide motifs: First listing, Immunogenet. 41: 178-228 (1995).
Rammensee, Some considerations on the use of peptides and mRNA for therapeutic vaccination against cancer, Immunol. Cell Biol. 84(3): 290-294 (2006).
Reche, et al., PEPVAC: a web server for multi-epitope vaccine development based on the prediction of supertypic MHC ligands, Nucl. Acids Res. 33: W138-W142 (2005).
Rimmelzwaan, et al., Cytotoxic T lymphocyte memory: role in cross-protective immunity against influenza?, Vaccine 13(8): 703-705 (1995).
Rimmelzwaan, et al., Sequence variation in the influenza A virus nucleoprotein associate with escape from cytotoxic T lymphocytes, Virus Res. 103(1-2): 97-100 (2004).
Rimmelzwaan, et al., Influenza virus CTL epitopes, remarkably conserved and remarkably variable, Vaccine 27(45): 6363-6365 (2009).
Robbins, et al., A broad cytotoxic T lymphocyte response to influenza type B virus presented by multiple HLA molecules, Inter.I Immunol. 9(6): 815-823 (1997).
Ruppert, et al., Prominent role of secondary anchor residues in peptide binding to HLA-A2.1 molecules, Cell 74(5): 929-937 (1993).
Scheibenbogen, et al., A sensitive ELISPOT assay for detection of CD8-+ T lymphocytes specific for HLA class I-binding epitopes derived from influenza proteins in the blood of healthy donors and melanoma patients, Clin. Can. Res. 3(2): 221-226 (1997).
Schmittel, et al., Application of the IFN-gamma ELISPOT assay to quantify T cell responses against proteins, J. Immunol. Meth. 247: 17-24 (2001).
Schoenborn, et al., Regulation of interferon-gamma during innate and adaptive immune responses, Adv. Immunol. 96: 41-101 (2007) (Abstract only).
Schrader, et al., Genetic Characterization of a Porcine H1N2 Influenza Virus Strain Isolated in Germany, Intervirol. 46(1): 66-70 (2003).
Schrader, et al., UNIPROT Submission, Accession No. Q45VS4, Necleoprotein, fragment, Influenza A virus (A/swine/Bakum/1832/00) (2005).
Schueler-Furman, et al., Knowledge-based structure prediction of MHC class I bound peptides: A study of 23 complexes, Folding Design 3: 549-564 (1998).
Schweiger, GenBank Submission, Accession No. ABR20736, Matrix protein 2, partial, Inflenza A virus (A/Sachsen-Anhait/6/00(H3N2))(2000).
Bette, et al., Prediction of major histocompatibility complex binding regions of protein anitgens by sequence pattern analysis, Proc. Natl. Acad. Sci. USA 86: 3296-3300 (1989).
Bette, et al., The relationship between class I binding affinity and immunogenicity of potential cytotoxic T cell epitopes, J. Immunol. 153: 5586-5592 (1994).
Bette, et al., Peptide binding to the most frequent HLA-A class I alleles measured by quantitative molecular binding assays, Mol. Immunol. 31: 813-822 (1994).
Shin, et al., Combinatorial solid phase peptide synthesis and bioassays, J Biochem. Mol. Biol. 38(5): 517-525 (2005).
Shirai, et al., CTL responses of HLA-A2.1-transgenic mice specific for hepatitis C viral peptides predict epitopes for CTL of humans carrying Hla-A2.1, J. of Immunol. 154(6): 2733-2742 (1995).
Smith, et al., Evolution and adaptation of H5N1 influenza virus in avian and human hosts in Indonesia and Vietnam, Virology, 350(2): 258-268 (2006).
Smith, et al., UNIPROT Submission, Accession No. Q1KJ15, Influenza A strain (A/duck/Vietnam/5649/2005(H5N1)) (2006).
Snyder, et al., Protection against lethal vaccinia virus challenge in HLA-A2 transgenic mice by immunization with a single CD8+ T-cell peptide epitope of vaccinia and variola viruses, J. Virol. 78(13) 7052-7060 (2004).
SIPO, Search Report, SG Patent Application Serial No. 201100861-2, pp. 9, (dated Jun. 15, 2012).
Stevanovic, Structural basis of immunogenicity, Transplant Immunol. 10: 133-136 (2002).
Stoloff, et al., Synthetic multi-epitope peptides identified in sillico induce protective immunity against multiple influenza serotypes, Eur. J. Immunol. 37(9): 2441-2449 (2007).
Sturniolo, et al., Generation of tissue-specific and promiscuous HLA ligand databases using DNA microarrays and virtual HLA class II matrices, Nat. Biotech. 17: 555-561 (1999).
Sudo, et al., Differences in MHC Class I self peptide repertoires among HLA-A2 subtypes, J. Immunol. 155: 4749-4756 (1995).
Tamura, et al., Defense mechansims against Influenza Virus infection in the respiratory tract mucosa, Jpn. J. Infect. Dis. 57: 236-247 (2004).
Tamura, et al., Mechanisms of broad cross-protection provided by influenza virus infection and their application to vaccines, Jpn. J. Infect. Dis. 58(4): 195-207 (2005).
Tana, et al., A HLA binding motif-aided peptide epitope library: A novel library design for the screening of HLA-DR4-restricted antigenic peptides recognized by CD4+ T cells, J. Hum. Genet. 43: 14-21 (1998).
Tang, et al., Isolation and Characterization of H3N2 Influenza A Virus from Turkeys, Avian Dis. 49(2): 207-213 (2005).
Tang, et al., EMBL-EBI Submission, Accession No. Q5UAH5, Matrix protein, fragment, Influenza A virus (A/turkey/Ohio/313053/04(H3N2)) (2004).
Taubenberger, et al., Initial Genetic Characterization of the 1918 Spanish Influenza Virus, Science, 275: 1793-1796 (1997).
Taubenberger, et al., EMBL-EBI Submission, Accession No. O10427, Matrix protein 2, fragment, Influenza A virus (A/South Carolina/1/18(H1N1)) (1997).
Thomas, et al., Cell-mediated protection in influenza infection, Emerg. Infect. Dis. 12(1): 48-54 (2006).
Thornton, et al., Location of "continuous" antigenic determinants in the protruding regions of proteins, EMBO J. 5: 409-413 (1986).
Tolle, et al. Variability of the env gene in cynomolgus macaques persistently infected with human immunodeficiency virus type 2 strain ben, J. Virol. 68(4): 2765-2771 (1994).
Tourdot, et al., Characterization of a new H-2Dk-restricted epitope prominent in primary influenza A virus infection, J. Gen. Virol. 82: 1749-1755 (2001).
Townsend, et al., Cytotoxic T cells recognize fragments of the influenza nucleoprotein, Cell 42: 457-467 (1985).

(56) References Cited

OTHER PUBLICATIONS

Trojan, et al., Immune reactivity against a novel HLA-A3-restricted Influenza virus peptide identified by predictive algorithms and interferon-gamma quantitative PCR, J. Immunother. 26(1): 41-46 (2003).

Ulmer, et al., Heterologous Protection Against Influenza by Injection of DNA Encoding a Viral Protein, Science 259: 1745-1749 (1993).

US Congress, "A Potential Influenza Pandemic: Possible Macroeconomic Effects and Policy Issues," Congressional Budget Office Assessment (2005).

Uzi, et al, Generation of an immunodominant CTL epitope is affected by proteasome subunit composition and stability of the antigenic protein, J. Immunol. 163: 6045-6052 (1999).

Voeten, et al., Antigen processing for MHC class I restricted presentation of exogenous influenza A virus nucleoprotein by B-lymphoblastoid cells, Clin. Exp. Immunol. 125(3): 423-431 (2001)(Abstract only).

Ward, et al., Immunotherapeutic potential of whole tumour cells, Can. Immunol. Immunother, 51(7): 351-357 (2002).

Webster, et al., The importance of animal influenza for human disease, Vaccine, 20(2): S16-S20 (2002).

WHO global influenza preparedness plan: The role of WHO and recommendations for national measures before and during pandemics, World Health Organization, (2005).

Woodland, Cell-mediated immunity to respiratory virus infections, Curr. Opin. Immunol. 15(4): 430 (2003).

Xu, et al., Genetic variation in neuramindase genes of influenza A (H3N2) viruses, Virology 224(1): 175-183 (1996).

Yang, et al., Expression of HLA-DP0401 molecules for identification of DP0401 restricted antigen specific T cells, J. Clin. Immunol. 25(5): 428-436 (2005).

Yewdell, et al., Immunodominance in major histocompatibility complex class I-restricted T lymphocyte responses, Annu. Rev. Immunol. 17: 51-88 (1999).

Zhong, et al., Genome-wide characterization of a viral cytotoxic T lymphocyte epitope repertoire, J. Biol. Chem. 278 (46): 45135-45144 (2003).

\* cited by examiner

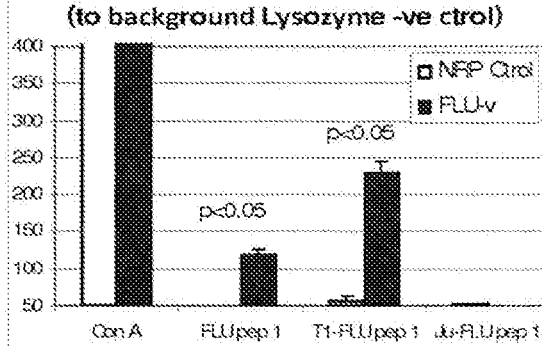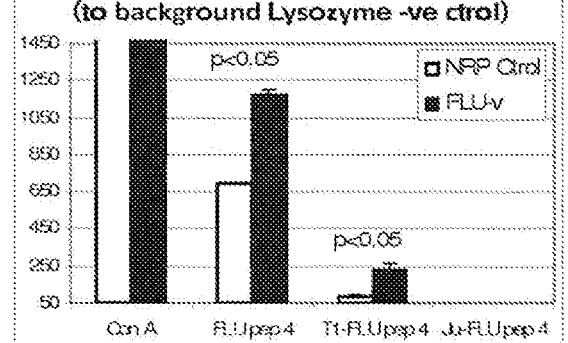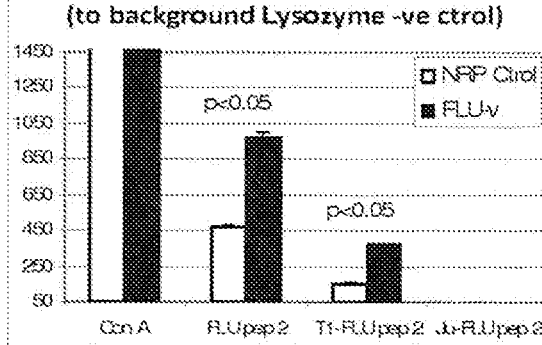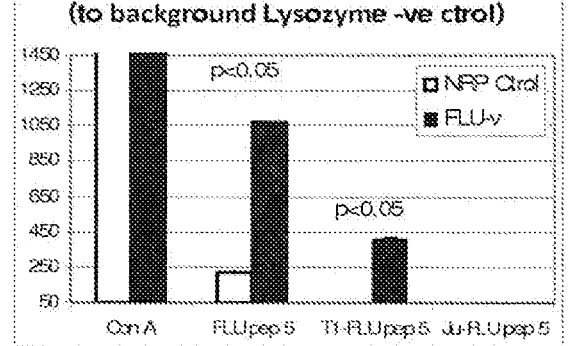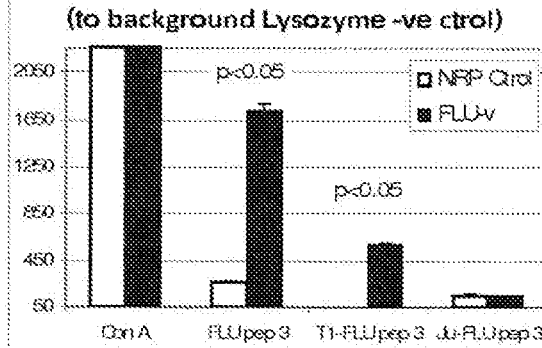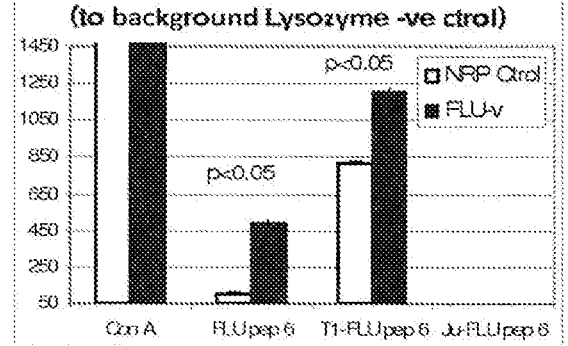

FLU-v = combination of P1 P2 P3 P4 P5 & P6
Immunise mouse with FLU-v
Harvest splenocytes after 21

T1 transfected with P1 (or P2 etc.)
or
mouse antigen presenting cells allowed to
present P1 naturally by adding P1 (or P2 etc.) to splenocytes APC(HLA)-P1 +
T cells reactive to APC(HLA)-P1  ⟶  HLA ↘ (APC) ↙ P1   (T) ∿ INF-γ
(or P2 etc.)

Innoculation was with FLU-v

JURKAT transfected with P1 (or P2 etc.)
or
mouse antigen presenting cells allowed to
present P1 naturally by adding P1 (or P2 etc.) to splenocytes APC(non-HLA)-P1 +
T cells reactive to APC(HLA)-P1  ⟶  No reaction (no IFN-γ)
(or P2 etc.)

Innoculation was with FLU-v

FIG. 6

```
                          SEQUENCE LISTING

<160> NUMBER OF SEQ ID NOS: 12

<210> SEQ ID NO 1
<211> LENGTH: 32
<212> TYPE: PRT
<213> ORGANISM: Artificial Sequence
<220> FEATURE:
<223> OTHER INFORMATION: Influenza virus consensus sequence

<400> SEQUENCE: 1

Asp Leu Glu Ala Leu Met Glu Trp Leu Lys Thr Arg Pro Ile Leu Ser
1               5                   10                  15

Pro Leu Thr Lys Gly Ile Leu Gly Phe Val Phe Thr Leu Thr Val Pro
            20                  25                  30

<210> SEQ ID NO 2
<211> LENGTH: 35
<212> TYPE: PRT
<213> ORGANISM: Artificial Sequence
<220> FEATURE:
<223> OTHER INFORMATION: Influenza virus consensus sequence

<400> SEQUENCE: 2

Leu Leu Tyr Cys Leu Met Val Met Tyr Leu Asn Pro Gly Asn Tyr Ser
1               5                   10                  15

Met Gln Val Lys Leu Gly Thr Leu Cys Ala Leu Cys Glu Lys Gln Ala
            20                  25                  30

Ser His Ser
        35

<210> SEQ ID NO 3
<211> LENGTH: 21
<212> TYPE: PRT
<213> ORGANISM: Artificial Sequence
<220> FEATURE:
<223> OTHER INFORMATION: Influenza virus consensus sequence

<400> SEQUENCE: 3

Asp Leu Ile Phe Leu Ala Arg Ser Ala Leu Ile Leu Arg Gly Ser Val
1               5                   10                  15

Ala His Lys Ser Cys
```

-continued

20

<210> SEQ ID NO 4
<211> LENGTH: 21
<212> TYPE: PRT
<213> ORGANISM: Artificial Sequence
<220> FEATURE:
<223> OTHER INFORMATION: Influenza virus consensus sequence

<400> SEQUENCE: 4

```
Pro Gly Ile Ala Asp Ile Glu Asp Leu Thr Leu Leu Ala Arg Ser Met
1               5                   10                  15

Val Val Val Arg Pro
            20
```

<210> SEQ ID NO 5
<211> LENGTH: 34
<212> TYPE: PRT
<213> ORGANISM: Artificial Sequence
<220> FEATURE:
<223> OTHER INFORMATION: Influenza virus consensus sequence

<400> SEQUENCE: 5

```
Leu Leu Ile Asp Gly Thr Ala Ser Leu Ser Pro Gly Met Met Met Gly
1               5                   10                  15

Met Phe Asn Met Leu Ser Thr Val Leu Gly Val Ser Ile Leu Asn Leu
            20                  25                  30

Gly Gln
```

<210> SEQ ID NO 6
<211> LENGTH: 24
<212> TYPE: PRT
<213> ORGANISM: Artificial Sequence
<220> FEATURE:
<223> OTHER INFORMATION: Influenza virus consensus sequence

<400> SEQUENCE: 6

```
Ile Ile Gly Ile Leu His Leu Ile Leu Trp Ile Leu Asp Arg Leu Phe
1               5                   10                  15

Phe Lys Cys Ile Tyr Arg Leu Phe
            20
```

<210> SEQ ID NO 7
<211> LENGTH: 252
<212> TYPE: PRT
<213> ORGANISM: Artificial Sequence
<220> FEATURE:
<223> OTHER INFORMATION: M1 Influenza A consensus sequence

<400> SEQUENCE: 7

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95
```

-continued

```
Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Lys His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val Gln Ala Met Arg Thr Val Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250

<210> SEQ ID NO 8
<211> LENGTH: 248
<212> TYPE: PRT
<213> ORGANISM: Artificial Sequence
<220> FEATURE:
<223> OTHER INFORMATION: M1 Influenza B Consensus sequence
<400> SEQUENCE: 8

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205
```

```
Ile Gly Val Leu Arg Ser Leu Gly Ala Ser Gln Lys Asn Gly Glu Gly
            210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245
```

<210> SEQ ID NO 9
<211> LENGTH: 498
<212> TYPE: PRT
<213> ORGANISM: Artificial Sequence
<220> FEATURE:
<223> OTHER INFORMATION: NP Influenza A Consensus sequence

<400> SEQUENCE: 9

```
Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Lys Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320
```

-continued

```
Asn Pro Ala His Lys Ser Gln Leu Val Trp Met Ala Cys His Ser Ala
            325                 330                 335

Ala Phe Glu Asp Leu Arg Leu Leu Ser Phe Ile Arg Gly Thr Lys Val
        340                 345                 350

Ser Pro Arg Gly Lys Leu Ser Thr Arg Gly Val Gln Ile Ala Ser Asn
    355                 360                 365

Glu Asn Met Asp Asn Met Gly Ser Ser Thr Leu Glu Leu Arg Ser Gly
370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Lys Ser Thr Val Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 10
<211> LENGTH: 560
<212> TYPE: PRT
<213> ORGANISM: Artificial Sequence
<220> FEATURE:
<223> OTHER INFORMATION: NP Influenza B Consensus sequence

<400> SEQUENCE: 10

```
Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Ala Asp Val Gly Arg
    50                  55                  60

Lys Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175
```

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
            195                 200                 205

Phe Gln Arg Ser Lys Ala Leu Lys Arg Val Gly Leu Asp Pro Ser Leu
            210                 215                 220

Ile Ser Thr Phe Ala Gly Ser Thr Leu Pro Arg Arg Ser Gly Ala Thr
225                 230                 235                 240

Gly Val Ala Ile Lys Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
            275                 280                 285

Ser Ala Pro Gln Gln Lys Ala Leu Val Asp Gln Val Ile Gly Ser Arg
            290                 295                 300

Asn Pro Gly Ile Ala Asp Ile Glu Asp Leu Thr Leu Leu Ala Arg Ser
305                 310                 315                 320

Met Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
            355                 360                 365

Val Ser Ile Leu Arg Met Gly Asp Asp Ala Lys Asp Lys Ser Gln Leu
370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
            405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
            435                 440                 445

Gly Gly Asn Glu Val Gly Gly Asp Gly Gly Ser Gly Gln Ile Ser Cys
450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
            485                 490                 495

Lys Gly Asn Leu Leu Lys Met Met Asn Asp Ser Met Ala Lys Lys Thr
            500                 505                 510

Asn Gly Asn Ala Phe Ile Gly Lys Lys Met Phe Gln Ile Ser Asp Lys
            515                 520                 525

Asn Lys Thr Asn Pro Val Glu Ile Pro Ile Lys Gln Thr Ile Pro Asn
            530                 535                 540

Phe Phe Phe Gly Arg Asp Thr Ala Glu Asp Tyr Asp Asp Leu Asp Tyr
545                 550                 555                 560

<210> SEQ ID NO 11
<211> LENGTH: 758
<212> TYPE: PRT
<213> ORGANISM: Artificial Sequence
<220> FEATURE:
<223> OTHER INFORMATION: PB1 Influenza Consensus sequence

<400> SEQUENCE: 11

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Gly Tyr Leu Ile Arg Ala Leu Thr Leu
210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser

```
                    405                 410                 415
Thr Val Leu Gly Val Ser Ile Leu Asn Leu Gly Gln Lys Lys Tyr Thr
                420                 425                 430

Lys Thr Thr Tyr Trp Trp Asp Gly Leu Gln Ser Ser Asp Phe Ala
            435                 440                 445

Leu Ile Val Asn Ala Pro Asn His Glu Gly Ile Gln Ala Gly Val Asp
        450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
                515                 520                 525

Val Ile Lys Asn Asn Met Ile Asn Asn Asp Leu Gly Pro Ala Thr Ala
        530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Lys Ala Gly Leu Leu Val Ser
                580                 585                 590

Asp Gly Gly Pro Asn Leu Tyr Asn Ile Arg Asn Leu His Ile Pro Glu
                595                 600                 605

Val Cys Leu Lys Trp Glu Leu Met Asp Glu Asp Tyr Arg Gly Arg Leu
        610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
                740                 745                 750

Leu Arg Arg Gln Lys Lys
            755

<210> SEQ ID NO 12
<211> LENGTH: 97
<212> TYPE: PRT
<213> ORGANISM: Artificial Sequence
<220> FEATURE:
<223> OTHER INFORMATION: M2 Influenza consensus sequence

<400> SEQUENCE: 12

Met Ser Leu Leu Thr Glu Val Glu Thr Pro Ile Arg Asn Glu Trp Gly
```

-continued

```
1               5                   10                  15
Cys Arg Cys Asn Asp Ser Ser Asp Pro Leu Val Val Ala Ala Ser Ile
            20                  25                  30

Ile Gly Ile Leu His Leu Ile Leu Trp Ile Leu Asp Arg Leu Phe Phe
            35                  40                  45

Lys Cys Ile Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Asn Ala Val Asp Ala Asp Asp Ser His Phe Val Ser Ile Glu Leu
                85                  90                  95

Glu
```

INFLUENZA PEPTIDES AND COMPOSITIONS

This is a continuation application and claims priority pursuant to 35 U.S.C. § 120 to U.S. Non-Provisional patent application Ser. No. 15/865,214, filed Jan. 8, 2018, a continuation application that claims priority to U.S. Non-Provisional patent application Ser. No. 15/231,347, filed Aug. 8, 2016, now U.S. Pat. No. 9,889,191, a continuation application that claims priority to U.S. Non-Provisional patent application Ser. No. 13/906,232, filed May 30, 2013, now U.S. Pat. No. 9,446,116, a continuation application that claims priority to U.S. Non-Provisional patent application Ser. No. 12/278,728, filed May 26, 2009, now U.S. Pat. No. 8,475,802, a 35 U.S.C. § 371 National Stage Filing of PCT/GB2007/000383, filed Feb. 5, 2007, an International Patent Application that claims priority to GB 0613977.8, filed Jul. 13, 2006 and GB 0602416.0, filed Feb. 7, 2006, each of which is hereby incorporated by reference in its entirety.

The invention concerns peptide sequences, compositions comprising the peptide sequences, and in particular influenza vaccines comprising the sequences and the compositions, and uses of the sequences. The present invention is especially concerned with vaccines that are protective against a plurality of influenza virus strains, including existing viruses across different species (e.g. protective against both human and avian influenza) as well as future viruses that have mutated from existing viruses (such as a future mutated form of avian flu that is readily transmissible from human to human, which could potentially give rise to an influenza pandemic).

The defense against disease is critical for the survival of all animals, and the defense mechanism employed for this purpose is the animal immune system. Understanding the immune system is therefore a key to understanding the development of new and more sophisticated treatments for humans and animals alike.

The mechanism of operation of the immune system has been under investigation for many years. The system is composed of a number of cell types and a variety of molecules, making it extremely complex. Even after many years of study, the full extent of the immune system components, and their interaction with each other, is imperfectly understood.

Many years ago it was recognised that a person who recovers from a particular disease may acquire some protection in future against that disease, but not against a disease which that person has not yet contracted. This fundamental aspect of the immune system was interpreted at that time by considering that the immune system acquired a kind of 'memory' against certain pathogens once exposure to such pathogens had taken place, that memory being specific to a certain disease.

Gradually, it became known that exposure to less harmful variants of a pathogen could induce protection against more harmful variants (e.g. exposure to cowpox to protect against smallpox, or exposure to an inactivated anthrax to protect against live anthrax). Thus, the idea of vaccination against a disease arose.

It is now known that the immune system has at least two divisions: innate immunity and adaptive immunity. The innate system is fully functional before a pathogen enters the system, whilst the adaptive system is switched on after the pathogen enters the system. It then develops an attack specific to the pathogen. The innate system comprises a number of components, including phagocytes such as macrophages, which (as the name suggests) 'eat' or engulf foreign bodies such as pathogens.

Typically, but not exclusively, the present invention is concerned with the adaptive immune system, and unless specifically indicated otherwise, 'immune system' in the present context refers to the adaptive immune system.

In order to understand more fully how the immune system functions, the role of its individual components must be carefully considered. In respect of the adaptive immune system, it is well known that immunity against pathogens is provided by the action of lymphocytes, which constitute the most common cell type in the immune system. There are two types of lymphocyte: the B lymphocyte and the T lymphocyte. These are generally termed B cells and T cells respectively.

B cells have the ability to develop into plasma cells, which manufacture antibodies. Antibodies are very important components of the animal immune system. They are produced in response to some signature portion of the invading pathogen (an antigen of the pathogen—antigens here being defined as any foreign substance recognised by the immune system) and are usually specific to that pathogen. However, if two pathogens are very similar, or at least contain the same antigen, then antibodies produced against one can nevertheless be effective against the other (they may 'cross-react'). This explains why inoculation with cowpox may protect against smallpox. It is important to realise that the antibodies 'recognise' only a small portion of the antigenic molecule of the pathogen rather than the pathogen as a whole. These portions are termed epitopes.

T cells do not possess or produce antibodies. Instead, they recognise fragments (i.e. epitopes) of the foreign antigen complexed with major histocompatibility complex (MHC) (or in the case of humans, human leucocyte antigen (HLA)) via a specialised receptor known as TCR (T cell receptor). T cells are themselves divisible into subsets which can have either a regulatory function or an effector function. The effector cells are involved with 'effecting' the removal of foreign substances. For example, cytotoxic T cells (CTL) are effector cells that are able to kill infected cells, as well as other unwanted species such as tumour cells. Regulatory T cells, on the other hand, play a role in helping effector T and B cells to become more effective. Due to this function, these regulatory T cells are often termed 'helper' T cells. Other regulatory T cells, termed 'suppressor' T cells, are thought to inhibit immune responses, but these are less well understood. Regulatory T cells may also interact with components of the innate immune system to boost their activity.

In a normal healthy individual, the lymphocytes in the immune system remain in an inactive 'resting' state until an immune response is triggered. When an immune response is required, the lymphocytes become activated, proliferate and begin to carry out their designated functions. For example, any resting T cell displaying on its surface a TCR that recognises an epitope of the invading pathogen complexed with a MHC molecule is activated, proliferates (this being termed clonal expansion) and the resulting offspring start to actively carry out their predetermined effector functions required to combat the invading organisms.

When the immune response is completed, (i.e. the pathogens and/or infected cells have been eliminated) the lymphocytes revert to a resting state once again. This resting state is not, however, equivalent to the initial inactive resting state. Activated, but resting lymphocytes, can be rapidly recruited and induced to proliferate in response to an infection by the same, or closely related, pathogen at a later time.

This ability of activated resting lymphocytes, to deliver a faster and more powerful response following a second encounter with an invading pathogen, effectively provides the immune system with 'memory'. The exploitation of the immune system's memory is the basis for all long-term immunoprophylactic drugs (e.g. vaccines) and remains the goal of much long-term immunotherapeutic drug development.

In order for cells to perform their functions within the complex systems of an animal, the cells need to have 'receptors' on their surfaces. These receptors are capable of 'recognising' specific substances that control various essential processes such as activation, proliferation and adherence to other cells or substrates. For example, in the case of the immune system, the receptors on T and B cells allow them not only to recognise antigen but also to interact with each other and thus regulate their activities. Without these receptors, the cells would lack an essential means of communication and would be unable to act effectively in the concerted way that is essential for the immune system of a multicellular organism.

In order to be able to specifically recognise and deal with the wide range of pathogens present in the environment, the immune system has developed two types of highly variable antigen receptor on lymphocytes: antibodies in B cells and T cell receptors, or TCRs, in T cells.

There are a great many different possible antigen receptors present in the body, to enable the immune system to recognise a wide variety of invading pathogens. In fact there are approximately $10^{12}$ different B cells and T cell receptors in an individual. Each individual B cell has only one type of receptor, and so to deal with a particular pathogen, a B cell having the 'best fitting' receptor for an antigen of that pathogen must be selected. This process is termed 'clonal selection'. In theory, only a single clone may respond (a monoclonal response) or several (an oligoclonal response) or many (a polyclonal response) depending on the number of antigens/epitopes exhibited by the pathogen, and the specificity of the various selected B cells to these antigen/epitopes.

There is a major difference between the types of antigen that can be recognised by B cells and T cells. As far as it is known, only the receptors on the surface of B lymphocytes (i.e. antibodies) are capable of directly recognising antigens such as proteins on viruses and bacteria, or foreign molecules dissolved in body fluid. Antibodies can also be produced in a soluble form by the B cells when they are activated and develop into plasma cells. The antibodies are also termed immunoglobulins (abbreviated to Ig). T cell receptors, on the other hand, recognise only short peptides, also known as T cell epitopes, on the surface of cells of the body. These T-cell epitopes are produced by degradation of larger proteins that are either self (i.e. naturally occurring body proteins) or non-self (i.e. derived from foreign organisms infecting the body). Only those derived from foreign proteins, i.e. antigens, are normally capable of inducing an immune response in the body. Once produced, these epitopes are bound to a special type of molecule, the MHC (major histocompatibility complex) and the resulting complex is then presented on the cell surface for binding the T cell receptor.

It should be clear that due to the destructive nature of the immune response, the response has to act only against foreign pathogens, not against the body's own cells or proteins. Thus, the immune system needs to distinguish between 'self' and 'non-self'. It has been proposed that although clones of lymphocytes reacting against self are produced, they are deleted before any reaction can occur. This process is termed 'clonal deletion'. It has also been proposed that any self-reacting lymphocytes could be retained but only in a 'switched-off' state. This mechanism is termed 'clonal anergy'. Whatever the process considered, it remains unclear what is the exact underlying mechanism allowing lymphoid tissues, such as the thymus, to identify individual T cell clones reacting against self from the pool of T lymphocytes reacting only against non-self. The present inventors have now investigated more fully the mechanism of self/non-self discrimination, which has led to the development of the present invention. The inventors have now established a method of predicting the immunogenicity of a substance such as a peptide, which has enabled quicker identification of immunogenic peptide sequences within large proteins.

It has been known for many years that the major histocompatibility complex (MHC) plays a key role in the immune system of animals. The MHC molecules enable T cells to recognise antigens, as has already been discussed above. There are three general types of MHC molecule, class I, class II and class III. Class I and class II MHC molecules are glycoproteins that are present on the surface of the cell, whilst class III are usually soluble molecules present inside the cell. There are a large number of different types of MHC molecule. For example in humans (where MHC is termed HLA, human leukocyte antigen) there are several hundreds of different alleles of the genes coding for MHC molecules, meaning that in the human population there are many different types of HLA. The MHC of different species is typically named according to different conventions, thus MHC for mouse is termed H-2, for rat RT1 and for rabbit RLA. The different gene regions coding for different MHC molecules in an individual are usually individually named, such as HLA-A, HLA-C etc. in humans.

The MHC molecule is a critical immune system molecule, since it is this molecule that presents the epitopes of the antigens to the immune system. For example, if a T cell is to respond to a particular pathogen, the pathogen must have a least one antigen (such as a protein) that has at least one epitope (such as a peptide portion of the protein) that can bind to an MHC molecule on the surface of a cell and thus interact with a T cell which binds to the MHC-peptide complex. Thus, the immune response is dependent on the ability of the MHC to bind to an epitope. If there is no epitope that the MHC will bind to, or if there is no T cell which will bind to the MHC-peptide complex, then no immune response will occur.

In respect of 'self' proteins, however, one of several epitopes may be able to bind to the MHC molecule and hence potentially induce an immune response. On these occasions a specific "signal" must be provided for the self-reacting lymphocyte clones to be deleted or "switched off".

Since, as indicated above, both self and foreign (i.e. non-self) peptides can bind to MHC molecules, the binding of various peptides to MHC molecules has received particular scrutiny in the immunology field. Many investigations have sought to calculate or predict the strength of binding between certain MHC (particularly HLA and H-2) types and peptide sequences, to try to account for immune responses, or the lack of them (i.e. the "signal" required for discrimination between self and foreign). Examples of these include the following: Altuvia Y, Schueler O, Margalit H. 1995. "Ranking potential binding peptides to MHC molecules by a computational threading approach". J. Mol. Biol., 249: 244-250. Altuvia Y, Sette A, Sidney J, Southwood S, Margalit H. 1997. "A structure-based algorithm to predict potential binding peptides to MHC molecules with hydrophobic binding pockets". Hum. Immunol. 58: 1-11. G. E. Meister, C. G. P. Roberts, J. A. Berzofsky, A. S. De Groot, "Two novel T cell epitope prediction algorithms based on MHC-binding motifs; comparison of predicted and published epitopes from *Mycobacterium tuberculosis* and HIV protein sequences" Vaccine, 13:581-591, (1995). Gulukota K, Sidney J, Sette A, DeLisi C. 1997. "Two complementary methods for predicting peptides binding major histocompatibility complex molecules". J. Mol. Biol. 267:1258-1267. Pamer E G, Harty J T, Bevan M J. "Precise prediction of a dominant class I MHC-restricted epitope of *Listeria monocytogenes*". Nature 1991; 353: 852-855. Parker K C, Bednarek M A, Coligan J E. 1994. "Scheme for ranking potential HLA-A2 binding peptides based on independent binding of individual peptide side-chains". J. Immunol. 152:163-175. Rammensee H G, Friede T, Stevanoviic S. 1995. "MHC ligands and peptide motifs: First listing". Immunogenetics 41:178-228. Ruppert J, Sidney J, Celis E, Kubo R T, Grey H M, Sette A. 1993. "Prominent role of secondary anchor residues in peptide binding to HLA-A2.1 molecules". Cell 74:929-937. Schueler-Furman O, Elber R, Margalit H. 1998. "Knowledge-based structure prediction of MHC class I bound peptides: A study of 23 complexes". Fold Des. 3:549-564. Sette A, Buus S, Appella E, Smith J A, Chesnut R, Miles C, Colon S M, Grey H M. 1989. "Prediction of major histocompatibility complex binding regions of protein antigens by sequence pattern analysis". Proc. Natl. Acad. Sci. USA 86:3296-3300. Sette A, Sidney J, del Guercio M F, Southwood S, Ruppert J, Dahlberg C, Grey H M, Kubo R T. 1994a. "Peptide binding to the most frequent HLA-A class I alleles measured by quantitative molecular binding assays". Mol. Immunol. 31:813-822. Sette A, Vitiello A, Reherman B, Fowler P, Nayersina R, Kast W M, Melief C J M, Oseroff C, Yuan L, Ruppert J, et al. 1994b. "The relationship between class I binding affinity and immunogenicity of potential cytotoxic T cell epitopes". J. Immunol. 153:5586-5592. Stefan Stevanovic (2002): "Structural basis of immunogenicity", Transplant Immunology 10 133-136. Sturniolo T, Bono E, Ding J, Raddrizzani L, Tuereci O, Sahin U, Braxenthaler M, Gallazzi F, Protti M P, Sinigaglia F, Hammer J. 1999. "Generation of tissue-specific and promiscuous HLA ligand databases using DNA microarrays and virtual HLA class II matrices". Nat. Biotechnol. 17:555-561. T. Sudo, N. Kamikawaji, A. Kimura, Y. Date, C. J. Savoie, H. Nakashima, E. Furuichi, S. Kuhara, and T. Sasazuki, "Differences in MHC Class I self peptide repertoires among HLA-A2 subtypes." J. Immunol.: 155: 4749-4756, (1995). T. Tana, N. Kamikawaji, C. J. Savoie, T. Sudo, Y. Kinoshita, T. Sasazuki, "A HLA binding motif-aided peptide epitope library: A novel library design for the screening of HLA-DR4-restricted antigenic peptides recognized by CD4+ T cells." J. Human Genet., 43:14-21 (1998). K. Falk, et al. "Allele-specific motifs revealed by sequencing of self-peptides eluted from MHC molecules", Nature, Vol. 351, 290-297 (1991). T Elliott et al. "Peptide-induced conformational change of the class I heavy chain", Nature, Vol. 351, 402-407, (1991). P. Parham, "Deconstructing the MHC", Nature, Vol. 360, 300-301, (1992). Hwai-Chen Guo et al., "Different length peptides bind to HLA-Aw68 similarly at their ends but bulge out in the middle", Nature, Vol. 360, 364-367, (1992). Y. Chen et al. "Naturally processed peptides longer than nine amino acid residues bind to the class I MHC molecule HLA-A2.1 with high affinity and in different conformations", J. Immunol., 152, 2874-2881, (1994). D. F. Hunt et al. "Characterization of peptides bound to the class I MHC molecule HLA-A2.1 by mass spectrometry", Science, Vol. 255, 1261-1263, (1992).

Generally, the prior art attempts to predict the immunogenicity of particular peptides by calculating the strength of binding between that peptide and the known binding environment of a particular MHC molecule. The binding environment involves a 'pocket' in the MHC molecule that is adapted to accept a peptide of a certain length (such as 7-15 amino acids). The structure of the pocket may already be known from previous X-ray crystallographic studies. This strength may be calculated mathematically using appropriate algorithms for atomic and molecular interaction. Alternatively, the prior art may attempt to 'score' the binding strength of a peptide based upon motifs existing in the peptide, such as particular amino acids being present at particular positions in a peptide of a certain length, e.g. a proline present at position 3 in an 8-amino acid peptide binding to a particular known HLA molecule. Generally these approaches have met with limited success.

The present inventors believe that they have improved upon the above theories from a better understanding of how T cells reacting against self-substances such as self-proteins are identified prior to their elimination (clonal deletion) or silencing (clonal energy). Accordingly, the inventors have been able to identify specific immunogenic peptide sequences that may provide protection against specific pathogens, and have developed vaccines to these pathogens, using the identified sequences. In the case of the present invention, the inventors have developed peptides useful in influenza vaccines eliciting a T cell response.

Previously, influenza vaccines have been developed by identifying an existing influenza virus strain and then producing a vaccine specific to that virus. Generally, the vaccines have been based upon a B cell (antibody) response, the antibody being reactive with the surface antigens (i.e. Hemagglutinin and Neuraminidase) of the specific influenza virus strain against which it has been developed. Typically, the surface proteins comprising the antigens are variable from one influenza virus strain to the next, since mutation of the virus to produce a new virus tends to occur in the surface proteins. The consequence of this is that conventional influenza vaccines generally protect only against one specific virus strain, and will not protect against a new strain that results from a mutation. Thus, a new vaccine is required for protection against an emerging strain. The clear problem with this approach is that there is a period of time between emergence of the new virus strain, and development of the vaccine, during which there is no protection available against the virus. If the virus is particularly harmful, this can lead to many millions of deaths, as occurred in the major influenza pandemics of the last century.

It has been known for some time that cytotoxic T lymphocytes may provide an immune response to influenza virus strains. Recent studies have shown that a CTL response in humans may be directed towards multiple epitopes. It has been suggested that there is a dominant response to the HLA-A2 restricted M-1 58-66 epitope. Such studies include A. C. Boon et al, J. Virol, January 2002, 582-90; S. Tamura et al Jpn. J. Infect. Dis., December 2004, 236-47; G. Deliyannis et al J. Virol., May 2002, 4212-21; C. Gianfrani et al Hum. Immunol., May 2000, 438-52; and J. Jameson et al J. Immunol., June 1999, 7578-83.

There has recently also been investigation into specific immunogenic peptides that might be useful in developing an influenza vaccine eliciting a T cell response. Typically, such work has involved investigation of CTL response to test influenza peptides, e.g. in transgenic mice. The tested peptides tend to be short sequences that might be reactive to one MHC (or HLA) type, and are taken from a specific test influenza strain. For example, in Vaccine, 2005, 5231-44, N. Hu et al disclose testing wild type M1 58-66 peptide in HLA Tg mice expressing HLA-A2, -B7 or -B27. The results show that the peptide is an influenza epitope recognised by transgenic mice expressing HLA-A2. In Clin. Exp. Immunol., October 2005, 45-52, A. C. Boon et al disclose M1 58-66 and NP 44-52 influenza A peptides as epitopes recognised in HLA-A*0101 and HLA-A*0201 individuals. In Cell Immunol., April 2005, 110-123, E. Cheuk et al disclose NP 383-391 influenza A peptide as an epitope recognised in HLA-B27/H2 class I-deficient mice. Using epitope prediction programs, the authors identified three more B27 restricted influenza A epitopes, BP-2 702-710, PB-1 571-579 and PB-2 368-376. In J. Immunol., February 2004, 2453-60, A. C. Boon et al disclose human CTL clones specific for natural variants of the HLA-B*3501-restricted epitope in NP 418-426. In J. Immunother., January-February 2003, 41-6, A. Trojan et al disclose the HLA-A3-restricted 9-mer which is capable of inducing specific CTL reactivity. HLA-A2 restricted influenza A virus matrix peptide GILGFVFTL is also disclosed. In J. Gen. Virol., July 2001, 1749-55, S. Tourdot et al identify a murine D(k) restricted epitope derived from the influenza virus strain A/PR/8/34 polymerase protein PB-1, corresponding to amino acid residues 349-357. In J. Immunol., April 2001, 4627-33, G. T. Belz et al identify an immunogenic peptide (SSYRPVGI) from influenza polymerase protein PB-1, corresponding to amino acid residues 703-711 and a mimotope from PB-2 polymerase. PCT/US2005/002954 discloses CTL epitopes comprising NP 265-273 and also epitopes comprising NP 305-313. Finally, U.S. Pat. No. 6,740,325 discloses two CTL epitopes: NP 335-350, and NP 380-393.

Further studies have shown that data from transgenic mice provide a reliable model for the investigation of CTL responses in humans. In Int. Immunol., April 1995, 597-605, S. Man et al have shown that the dominant influenza A epitope recognised by HLA-A2.1-restricted cytotoxic T lymphocytes from HLA-A2.1 transgenic mice was the matrix protein 1 (M-1) peptide epitope that is immunodominant in human CTL responses. Further studies in this area have been conducted by E. J. Bernhard et al (J. Exp. Med., September 1998, 1157-62) and E. Cheuk et al (J. Immunol., November 2002, 5571-80).

However, although known epitopes have been studied extensively, none has yet been satisfactory for forming the basis of an influenza vaccine that is capable of protecting against more than a single strain of influenza virus. Moreover, vaccines based upon these single epitopes, even if they were to provide some protection, would likely be specific for a particular HLA, making them ineffective in a large proportion of the human population.

Thus, a significant problem with known vaccines, whether relying on a B-cell or T-cell response is that they only protect against an existing virus strain, and do not provide protection against possible future strains that might develop. With the emergence of the highly dangerous H5N1 strain in the avian population, the need for a vaccine in advance of a human pandemic based upon a subsequent mutation of the H5N1 strain has become more acute. Moreover, vaccines based upon known peptides eliciting T-cell responses may not be effective in large sections of the population.

Accordingly, it is an aim of the present invention to solve the problems associated with the known prior art as set out above. It is a further aim of the present invention to provide a polypeptide that is capable of eliciting a CTL immune response in vertebrates against a plurality of influenza strains and/or in a plurality of individuals expressing differing MHCs (HLAs). It is a further aim of the present invention to provide an influenza vaccine using the polypeptide of the invention. Preferably the vaccine is capable of protection against a plurality of influenza strains and/or is effective in a plurality of individuals expressing differing MHCs (HLAs).

Accordingly, the present invention provides a polypeptide having no more than 100 amino acids, which polypeptide comprises one or more sequences having at least 60% homology with any of SEQ ID 1-6, or comprises two or more epitopes having 7 amino acids or more, each epitope having at least 60% homology with a sub-sequence of any of SEQ ID 1-6 that has the same length as the epitope:

| | |
|---|---|
| SEQ ID 1 | DLEALMEWLKTRPILSPLTKGILGFVFTLTVP |
| SEQ ID 2 | LLYCLMVMYLNPGNYSMQVKLGTLCALCEKQASHS |
| SEQ ID 3 | DLIFLARSALILRGSVAHKSC |
| SEQ ID 4 | PGIADIEDLTLLARSMVVVRP |
| SEQ ID 5 | LLIDGTASLSPGMMMGMFNMLSTVLGVSILNLGQ |
| SEQ ID 6 | IIGILHLILWILDRLFFKCIYRLF | wherein, the polypeptide is immunogenic in a vertebrate expressing a major histocompatibility complex (MHC) allele, and wherein the polypeptide is not a complete influenza virus protein.

Thus, the polypeptide is one that may comprise the whole of (or may comprise at least two 7 or more residue parts of) any of the above sequences, but cannot have more than 100 amino acid residues in total. The polypeptide must also be immunogenic in a vertebrate expressing an MHC (HLA in humans) allele. An immunogenic polypeptide is understood in the present context to mean a polypeptide that elicits an immune response in a vertebrate, such as by binding to a vertebrate MHC and causing it to react with a cytotoxic T cell lymphocyte. One method for determining whether a polypeptide possesses immunogenicity is set out in Experiment 1 below. However, the present invention is not limited to such methods, and the skilled person may select any known method for determining immunogenicity, as desired.

As mentioned above, the polypeptide may be one comprising two 7 or more residue epitopes that react with one or more MHCs and so elicit a broad CTL response. The response may be in a single individual or may be in at least two different individuals (and the individuals may be of the same species or different species). Thus, the polypeptide may comprise at least two different 7 or more residue epitopes, each of which individually provides a response to a different subject. An epitope in the context of the present invention is a part of a polypeptide which is capable of binding to a vertebrate MHC in a vertebrate, preferably eliciting an immune response, such as by causing the MHC-epitope complex to react with a CTL. One method for determining whether a polypeptide is or contains an epitope is set out in Experiment 1 below. However, the present invention is not limited to such methods, and the skilled person may select any known method for determining whether a polypeptide is or contains an epitope, as desired.

The present inventors have found that the above sequences comprise a plurality of CTL epitopes, which may afford protection against influenza for a wide variety of vertebrates in a population. In addition, the inventors have analyzed all known influenza virus strain sequences across all species, and have found that the specified sequences are remarkably conserved across all known influenza virus strains. As such, these sequences are very unlikely to be significantly altered in new strains resulting from mutation of existing strains. Accordingly, the epitopes within these sequences that provide protection are highly likely to be present in unchanged form in new strains, since mutation does not normally occur in these regions. Consequently, these epitopes provide excellent opportunity not only for providing protection against existing influenza strains (such as the H5N1 strain of 'bird flu'), but also protecting against as yet unknown strains (such as a mutated form of H5N1 that could pass easily from human to human and form the basis of a pandemic).

As discussed above, the sequences have been identified after analysis of all known influenza virus strain sequences across all species. The sequences are thus consensus sequences developed from the above analysis. Despite being consensus sequences, the sequences in some cases correspond exactly to natural sequences in some of the known influenza virus strains. Due to the remarkable conservation in the sequences across all viruses in all species, the consensus sequences, even when differing from actual sequences, only differ in a small number of residues, and thus contain many smaller epitopes (8-mers, 9-mers, 10-mers etc.) for which there are no differences from natural sequences. The above consensus sequences as a whole thus contain many effective epitopes that are the same as the natural epitopes, as well as effective epitopes that differ only slightly from natural epitopes. It will be apparent to the skilled person that the invention extends not only to the consensus sequences and their epitopes, but also to the corresponding actual sequences in any influenza virus strains. Thus, sequences with some homology to the consensus sequences are also within the scope of the invention. Such homology allows substitution of, for example, up to 3 amino acids in an 8-mer epitope (62.5% homology) or in a 9-mer, 10-mer, or 11-mer epitope. It is preferred that no more than 10 such substitutions are identifiable in a sequence of the invention corresponding to the full sequences of SEQ ID 1-6 (66.6% homology for a 30-mer). Such substitutions are preferably conservative substitutions in line with known substitution schemes.

Having in mind that the invention extends from the consensus sequence to the corresponding natural sequences, then the invention also provides a polypeptide having no more than 100 amino acids, which polypeptide comprises one or more sequences defined by the following amino acid residues of an influenza virus protein, or comprises two or more epitopes having 7 amino acids or more from a sequence defined by the following amino acid residues of an influenza virus protein:

| | |
|---|---|
| residues 36-75 | of an M1 protein (preferably from an influenza A strain) |
| residues 124-158 | of an M1 protein (preferably from an influenza B strain) |
| residues 255-275 | of an NP protein (preferably from an influenza A strain) |
| residues 306-326 | of an NP protein (preferably from an influenza B strain) |
| residues 395-428 | of a PB1 protein residues 32-55 of an M2 protein | wherein, the polypeptide is immunogenic in a vertebrate expressing a major histocompatibility complex (MHC) allele, and wherein the polypeptide is not a complete influenza virus protein.

The sequence numbering referred to in the present invention is defined according to well-recognised principles. Thus, the numbering begins at 1 from the recognised translation initiation codon (ATG). This corresponds to a Methionine (M), for the segment of the Influenza genome coding for the protein of interest. In other words, it begins at 1 in respect of the Methionine shown as the first amino acid in the protein sequence of interest as used and defined by the databases in which the sequences have been set forth (i.e. GenBank, SwissProt, etc.).

The present invention will be described in more detail by way of example only with reference to the following Figures, in which:

FIG. 1A to 1F show IFN-γ production by primary splenocyte cultures of FLU-v and NRP vaccinated mice stimulated with Con A (10 μg/ml), soluble Lysozyme (5 μg/ml), purified soluble polypeptides (P1 (FIG. 1A), P2 (FIG. 1B), P3 (FIG. 1C), P4 (FIG. 1D), P5 (FIG. 1E) and P6 (FIG. 1F); 5 μg/ml) and HLA-matched T1 (T1) and mismatched JURKAT (Ju) human cells transfected with either Lysozyme, P1, P2, P3, P4, P5 or P6 according to the protocol described in Example 1 below (splenocyte to transfected cell ratio is 10:1). IFN-γ production is represented as the differential between the level of production in response to the antigen considered minus the IFN-γ produced in response to either soluble Lysozyme or the corresponding cell transfected with Lysozyme. Background levels of Lysozyme mediated production of IFN-γ were for soluble antigen 25±10 μg/ml, for antigen in T1 316±43 μg/ml, and for antigen in Jurkat 19±6 μg/ml;

FIG. 2 shows IFN-γ production by primary splenocyte cultures of FLU-v and NRP vaccinated mice stimulated with Con A (10 μg/ml), soluble Lysozyme (5 μg/ml), purified soluble FLU-v polypeptide preparation (P1, P2, P3, P4, P5 and P6 all together at 5 μg/ml) and HLA-matched T1 (T1) and mismatched JURKAT (Ju) human cells either infected with influenza strains A/New_Calcdonia/20/99, A/NYMC/X-147 or B/Johannesburg/5/99 or transfected with Lysozyme according to the protocol described in Example 1 below (splenocyte to infected/transfected cell ratio is 10:1); IFN-γ production is represented as the differential between the level of production in response to the antigen considered minus the IFN-γ produced in response to either soluble Lysozyme or the corresponding cell transfected with Lysozyme; background levels of Lysozyme mediated production of IFN-γ were for soluble antigen 25±10 μg/ml, for antigen in T1 316±43 μg/ml, and for antigen in Jurkat 19±6 μg/ml; and FIGS. 3A and 3B show survival of animals following a lethal challenge with Influenza A/PR/8/34; animals were immunised subcutaneously with either FLU-v or NRP-v on days 1 and 15 and on day 20 all were challenged intranasally with 45 μl of the virus (5×10$^7$ pfu per dose) under anaesthesia; animals in FIG. 3A were inoculated intraperitoneally with 100 μg of rat anti-mouse CD8 sera on days 19 and 22; animals in FIG. 3B were inoculated intraperitoneally with an irrelevant rat sera on days 19 and 22; the arrow indicates the date of intranasal challenge whilst the diamonds indicate the date animals were inoculated with the anti-CD8 sera.

FIG. 4 shows Scheme 1 innoculation.

FIG. 6 shows Scheme 3—FLU-v test for T1 and JUR-KAT.

Figure 3A:
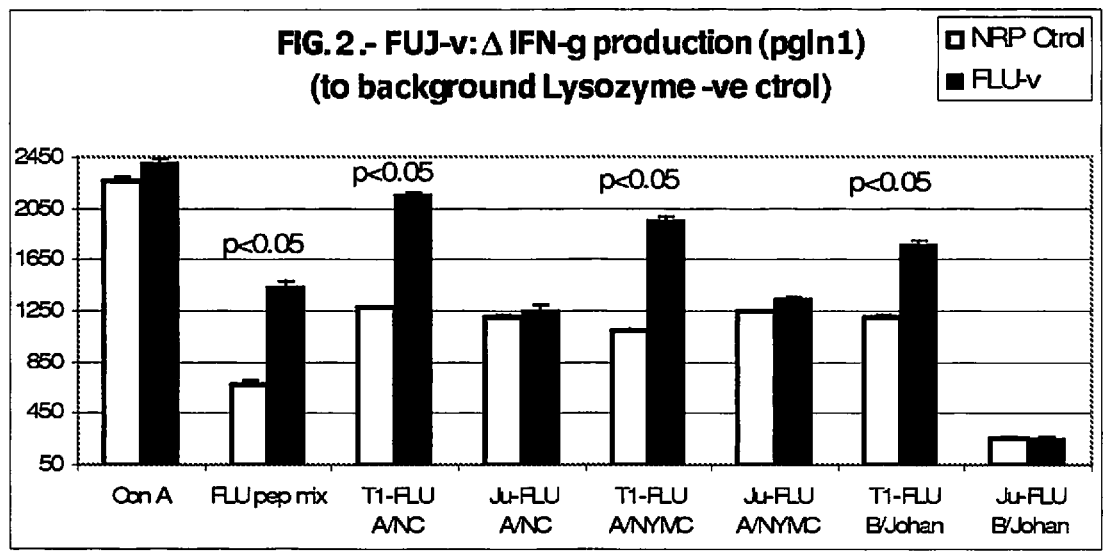

The polypeptide described above typically comprises one or more (preferably two or more) epitopes. These epitopes are preferably T cell epitopes, such as cytotoxic T lymphocyte (CTL) epitopes. Generally the polypeptide is immunogenic to an influenza virus strain, and preferably to a plurality of influenza virus strains. In the present context, a polypeptide immunogenic to an influenza virus strain is understood to mean a polypeptide that is part of an influenza virus protein and that elicits an immune system response, such as by exhibiting CTL reactivity when bound to an MHC. One method for determining whether a polypeptide possesses such immunogenicity is set out in Experiment 1 below. However, the present invention is not limited to such methods, and the skilled person may select any known method for determining immunogenicity, as desired.

In the present invention, the polypeptide comprises two or more sequences as described above. Typically, two, three, four, five or more such sequences may be present in the polypeptide, if desired. The more such epitopes are present, the greater the breadth of protection afforded within a population of humans and/or animals individuals with differing HLAs or MHCs.

The polypeptide according to the present invention may also comprise one or more further sequences that are not epitopes, if desired. Typically the further sequences are from one or more influenza virus proteins. These sequences may be situated between two or more of the sequences (the epitopes) described above, or may be situated at one or both ends of the polypeptide. The presence of such further sequences should not affect the function of the polypeptide, provided that the polypeptide as a whole does not become too large, interfering with the presentation of the epitopes in the vertebrate's immune system. In specific embodiments of the invention, when the polypeptide is homologous to SEQ ID 1, the further sequences are preferably one or more from an influenza M1 protein (preferably from an influenza A strain), when the polypeptide is homologous to SEQ ID 2, the further sequences are preferably one or more from an influenza M1 protein (preferably from an influenza B strain), when the polypeptide is homologous to SEQ ID 3, the further sequences are preferably one or more from an influenza NP protein (preferably from an influenza A strain), when the polypeptide is homologous to SEQ ID 4, the further sequences are preferably one or more from an influenza NP protein (preferably from an influenza B strain), when the polypeptide is homologous to SEQ ID 5, the further sequences are preferably one or more from an influenza PB1 protein, and when the polypeptide is homologous to SEQ ID 6, the further sequences are preferably one or more from an influenza M2 protein.

In the most preferred embodiments, the further sequences from the above-mentioned proteins are ones within the following consensus sequences, or ones having at least 60% homology with a sequence within the following consensus sequences:

```
M1 Influenza A Consensus-
                                                         SEQ ID 7
MSLLTEVETYVLSIVPSGPLKAEIAQRLEDVFAGKNTDLEALMEWLKTRPILSPLTKGILGFVF

TLTVPSERGLQRRRFVQNALNGNGDPNNMDKAVKLYRKLKREITFHGAKEIALSYSAGALASCM

GLIYNRMGAVTTEVAFGLVCATCEQIADSQHRSHRQMVATTNPLIKHENRMVLASTTAKAMEQM

AGSSEQAAEAMEIASQARQMVQAMRTVGTHPSSSTGLRDDLLENLQTYQKRMGVQMQRFK

M1 Influenza B Consensus-
                                                         SEQ ID 8
MSLFGDTIAYLLSLTEDGEGKAELAEKLHCWFGGKEFDLDSALEWIKNKRCLTDIQKALIGASI

CFLKPKDQERKRRFITEPLSGMGTTATKKKGLILAERKMRRCVSFHEAFEIAEGHESSALLYCL

MVMYLNPGNYSMQVKLGTLCALCEKQASHSHRAHSRAARSSVPGVRREMQMVSAMNTAKTMNGM

GKGEDVQKLAEELQSNIGVLRSLGASQKNGEGIAKDVMEVLKQSSMGNSALVKKYL

NP Influenza A Consensus-
                                                         SEQ ID 9
MASQGTKRSYEQMETDGDRQNATEIRASVGKMIDGIGRFYIQMCTELKLSDYEGRLIQNSLTIE

KMVLSAFDERRNRYLEEHPSAGKDPKKTGGPIYRRVDGKWMRELVLYDKEEIRRIWRQANNGED

ATAGLTHMMIWHSNLNDATYQRTRALVRTGMDPRMCSLMQGSTLPRRSGAAGAAVKGIGTMVME

LIRMIKRGINDRNFWRGENGRKTRSAYERMCNILKGKFQTAAQRAMVDQVRESRNPGNAEIEDL

IFLARSALILRGSVAHKSCLPACVYGPAVSSGYDFEKEGYSLVGIDPFKLLQNSQVYSLIRPNE

NPAHKSQLVWMACHSAAFEDLRLLSFIRGTKVSPRGKLSTRGVQIASNENMDNMGSSTLELRSG

YWAIRTRSGGNTNQQRASAGQISVQPTFSVQRNLPFEKSTVMAAFTGNTEGRTSDMRAEIIRMM

EGAKPEEVSFRGRGVFELSDEKATNPIVPSFDMSNEGSYFFGDNAEEYDN

NP Influenza B Consensus-
                                                         SEQ ID 10
MSNMDIDGINTGTIDKTPEEITSGTSGTTRPIIRPATLAPPSNKRTRNPSPERATTSSEADVGR

KTQKKQTPIEIKKSVYNMVVKLGEFYNQMMVKAGLNDDMERNLIQNAHAVERILLAATDDKKTE
```

```
                            -continued
FQKKKNARDVKEGKEEIDHNKTGGTFYKMVRDDKTIYFSPIRITFLKEEVKTMYKTTMGSDGFS

GLNHIMIGHSQMNDVCFQRSKALKRVGLDPSLISTFAGSTLPRRSGATGVAIKGGGTLVAEAIR

FIGRAMADRGLLRDIKAKTAYEKILLNLKNKCSAPQQKALVDQVIGSRNPGIADIEDLTLLARS

MVVVRPSVASKVVLPISIYAKIPQLGFNVEEYSMVGYEAMALYNMATPVSILRMGDDAKDKSQL

FFMSCFGAAYEDLRVLSALTGTEFKPRSALKCKGFHVPAKEQVEGMGAALMSIKLQFWAPMTRS

GGNEVGGDGGSGQISCSPVFAVERPIALSKQAVRRMLSMNIEGRDADVKGNLLKKMNDSMAKKT

NGNAFIGKKMFQISDKNKTNPVEIPIKQTIPNFFFGRDTAEDYDDLDY

PB1 Influenza Consensus-
                                                SEQ ID 11
MDVNPTLLFLKVPAQNAISTTFPYTGDPPYSHGTGTGYTMDTVNRTHQYSEKGKWTTNTETGAP

QLNPIDGPLPEDNEPSGYAQTDCVLEAMAFLEESHPGIFENSCLETMEVVQQTRVDKLTQGRQT

YDWTLNRNQPAATALANTIEVFRSNGLTANESGRLIDFLKDVMESMDKEEMEITTHFQRKRRVR

DNMTKKMVTQRTIGKKKQRVNKRGYLIRALTLNTMTKDAERGKLKRRAIATPGMQIRGFVYFVE

TLARSICEKLEQSGLPVGGNEKKAKLANVVRKKMINSQDTELSFTITGDNTKWNENQNPRMFLA

MITYITKNQPEWFRNILSIAPIMFSNKMARLGKGYMFESKRMKLRTQIPAEMLASIDLKYFNES

TRKKIEKIRPLLIDGTASLSPGMKMGMFNMLSTVLGVSILNLGQKKYTKTTYWWDGLQSSDDFA

LIVNAPNHEGIQAGVDRFYRTCKLVGINMSKKKSYINKTGTFEFTSFFYRYGFVANFSMELPSF

GVSGINESADMSIGVTVIKNNMINNDLGPATAQMALQLFIKDYRYTYRCHRGDTQIQTRRSFEL

KKLWDQTQSKAGLLVSDGGPNLYNIRNLHIPEVCLKWELMDEDYRGRLCNPLNPFVSHKEIESV

NNAVVMPAHGPAKSMEYDAVATTHSWIPKRNRSILNTSQRGILEDEQMYQKCCNLFEKFFPSSS

YRRPVGISSMVEAMVSRARIDARIDFESGRIKKEEFSEIMKICSTIEELRRQKK

M2 Influenza Consensus-
                                                SEQ ID 12
MSLLTEVETPIRNEWGCRCNDSSDPLVVAASIIGILHLILWILDRLFFKCIYRFKHGLKRGPS

TEGVPESMREEYRKEQQNAVDADDSHFVSIELE
```

The homology referred to above in respect of these sequences is preferably 75%, 85%, 95% or substantially 100%.

In the present invention, the influenza strain is not especially limited, and the polypeptides may be immunogenic against, and/or derived from, any known influenza strain. Preferably, however, the relevant strain is an Influenza A or Influenza B strain. Future influenza strains that have mutated from any of these existing strains may also be ones against which the polypeptides are immunogenic, or from which the polypeptides are derived.

The proteins within which the sequences defining the polypeptides of the present invention are situated are selected from M1, NP, PB and M2 proteins from any influenza virus strain (especially A and B strains) (the consensus sequences of which for all analyzed sequences, or alternatively the positions of which within the protein, are described above). The following specific proteins were analyzed by the inventors, and preferably the influenza virus proteins referred to in the invention are selected from these specific proteins, or mutations from these proteins. Thus, the specific sequences homologous to SEQ ID 1-6 described above are preferably the ones at the appropriate positions within the following proteins. Similarly, the sequences of the present invention defined by the residue positions within proteins from any influenza strain, namely residues 36-75 of M1 protein (especially infuenza A M1), residues 124-158 of M1 protein (especially in influenza B M1), residues 255-275 of NP protein (especially in influenza A NP), residues 306-326 of NP protein (especially in influenza B NP), residues 395-428 of PB1 protein, and residues 32-55 of M2 protein, are preferably those within the following specific proteins. The list is in the form |version number (gi number)|database identification (e.g. gb for GenBank)|NCBI accession number|optional further information (e.g. the accession number of the nucleotide sequence from which the protein sequence is derived). The sequences and corresponding influenza strains from which they derive can all be found from the public NCBI protein database. The protein database contains sequence data from the translated coding regions from DNA sequences in GenBank, EMBL, and DDBJ as well as protein sequences submitted to Protein Information Resource (PIR), SWISS-PROT, Protein Research Foundation (PRF), and Protein Data Bank (PDB) (sequences from solved structures).

| M1 proteins | | |
|---|---|---|
| \|27530653\|dbj\|BAC54009.1\|; | \|27530634\|dbj\|BAC53998.1\|; | \|53829719\|gb\|AAU94746.1\|; |
| \|53829716\|gb\|AAU94744.1\|; | \|53829713\|gb\|AAU94742.1\|; | \|53829710\|gb\|AAU94740.1\|; |

-continued

| M1 proteins |||
|---|---|---|
| \|53829707\|gb\|AAU94738.1\|; | \|53829704\|gb\|AAU94736.1\|; | \|53829701\|gb\|AAU94734.1\|; |
| \|53829698\|gb\|AAU94732.1\|; | \|53829695\|gb\|AAU94730.1\|; | \|53829692\|gb\|AAU94728.1\|; |
| \|53829689\|gb\|AAU94726.1\|; | \|53829686\|gb\|AAU94724.1\|; | \|53829683\|gb\|AAU94722.1\|; |
| \|8486160\|ref\|NP_056664.1\|; | \|30466242\|ref\|NP_848689.1\|; | \|30349250\|gb\|AAP22121.1\|; |
| \|30466211\|ref\|NP_848672.1\|; | \|30349219\|gb\|AAP22104.1\|; | \|4761025\|gb\|AAD29208.1\|AF100392_1\|; |
| \|4761022\|gb\|AAD29206.1\|AF100391_1\|; | | \|4761019\|gb\|AAD29204.1\|AF100390_1\|; |
| \|4761016\|gb\|AAD29202.1\|AF100389_1\|; | | \|4761013\|gb\|AAD29200.1\|AF100388_1\|; |
| \|4761010\|gb\|AAD29198.1\|AF100387_1\|; | | \|4761007\|gb\|AAD29196.1\|AF100386_1\|; |
| \|4761004\|gb\|AAD29194.1\|AF100385_1\|; | | \|4761001\|gb\|AAD29192.1\|AF100384_1\|; |
| \|4760998\|gb\|AAD29190.1\|AF100383_1\|; | | \|4760995\|gb\|AAD29188.1\|AF100382_1\|; |
| \|4760992\|gb\|AAD29186.1\|AF100381_1\|; | | \|4760989\|gb\|AAD29184.1\|AF100380_1\|; |
| \|4760986\|gb\|AAD29182.1\|AF100379_1\|; | | \|4760983\|gb\|AAD29180.1\|AF100378_1\|; |
| \|4760980\|gb\|AAD29178.1\|AF100377_1\|; | | \|4760977\|gb\|AAD29176.1\|AF100376_1\|; |
| \|4760974\|gb\|AAD29174.1\|AF100375_1\|; | | \|4760971\|gb\|AAD29172.1\|AF100374_1\|; |
| \|12862823\|dbj\|BAB32623.1\|; | \|12862820\|dbj\|BAB32621.1\|; | \|12862817\|dbj\|BAB32619.1\|; |
| \|5702096\|gb\|AAD47140.1\|; | \|51340785\|gb\|AAU01001.1\|; | \|50059438\|gb\|AAT69451.1\|; |
| \|50059400\|gb\|AAT69429.1\|; | \|50059419\|gb\|AAT69440.1\|; | \|325196\|gb\|AAA67100.1\|; |
| \|325202\|gb\|AAA43726.1\|; | \|138823\|sp\|P03489\|VMT1_INBLE\|; | \|138824\|sp\|P06816\|VMT1_INBSI\|; |
| \|138822\|sp\|P13880\|VMT1_INBAD\|; | \|138821\|sp\|P13879\|VMT1_INBAC\|; | \|325198\|gb\|AAA66416.1\|; |
| \|325194\|gb\|AAA66414.1\|; | \|9049382\|dbj\|BAA99399.1\|; | \|5764368\|gb\|AAD51265.1\|AF153257_1\|; |
| \|76443315\|gb\|ABA42441.1\|; | \|76443312\|gb\|ABA42439.1\|; | \|76443309\|gb\|ABA42437.1\|; |
| \|76443306\|eb\|ABA42435.1\|; | \|76443303\|gb\|ABA42433.1\|; | \|21636455\|gb\|AAM70003.1\|AF457712_1\|; |
| \|21636450\|gb\|AAM70000.1\|AF457710_1\|; | | \|21636434\|gb\|AAM69991.1\|AF457703_1\|; |
| \|21636416\|gb\|AAM69981.1\|AF457695_1\|; | | \|21636398\|gb\|AAM69971.1\|AF457687_1\|; |
| \|21636378\|gb\|AAM69960.1\|AF457678_1\|; | | \|9802291\|gb\|AAF99672.1\|AF258523_1\|; |
| \|9802288\|gb\|AAF99670.1\|AF258522_1\|; | | \|5764374\|gb\|AAD51269.1\|AF153259_1\|; |
| \|5805289\|gb\|AAD51928.1\|AF144306_1\|; | | \|5764371\|gb\|AAD51267.1\|AF153258_1\|; |
| \|71655384\|gb\|AAZ38740.1\|; | \|71655379\|gb\|AAZ38738.1\|; | \|71655371\|gb\|AAZ38736.1\|; |
| \|71655356\|gb\|AAZ38734.1\|; | \|71655345\|gb\|AAZ38732.1\|; | \|71655341\|gb\|AAZ38730.1\|; |
| \|71655320\|gb\|AAZ38728.1\|; | \|73852957\|ref\|YP_308671.1\|; | \|73912688\|ref\|YP_308854.1\|; |
| \|28849409\|gb\|AAO52887.1\|AF509044_1\|; | | \|5732422\|gb\|AAD49093.1\|AF156470_2\|; |
| \|5732419\|gb\|AAD49091.1\|AF156469_2\|; | | \|5732416\|gb\|AAD49089.1\|AF156468_2\|; |
| \|28194354\|gb\|AAO33517.1\|AF474058_1\|; | | \|28194351\|gb\|AAO33515.1\|AF474057_1\|; |
| \|28194348\|gb\|AAO33513.1\|AF474056_1\|; | | \|28194345\|gb\|AAO33511.1\|AF474055_1\|; |
| \|28194342\|gb\|AAO33509.1\|AF474054_1\|; | | \|28194339\|gb\|AAO33507.1\|AF474053_1\|; |
| \|28194336\|gb\|AAO33505.1\|AF474052_1\|; | | \|28194333\|gb\|AAO33503.1\|AF474051_1\|; |
| \|28194330\|gb\|AAO33501.1\|AF474050_1\|; | | \|28194327\|gb\|AAO33499.1\|AF474049_1\|; |
| \|28849451\|gb\|AAO52908.1\|AF509065_1\|; | | \|28849449\|gb\|AAO52907.1\|AF509064_1\|; |
| \|28849447\|gb\|AAO52906.1\|AF509063_1\|; | | \|28849445\|gb\|AAO52905.1\|AF509062_1\|; |
| \|28849443\|gb\|AAO52904.1\|AF509061_1\|; | | \|28849441\|gb\|AAO52903.1\|AF509060_1\|; |
| \|28849439\|gb\|AAO52902.1\|AF509059_1\|; | | \|28849437\|gb\|AAO52901.1\|AF509058_1\|; |
| \|28849435\|gb\|AAO52900.1\|AF509057_1\|; | | \|28849433\|gb\|AAO52899.1\|AF509056_1\|; |
| \|28849431\|gb\|AAO52898.1\|AF509055_1\|; | | \|28849429\|gb\|AAO52897.1\|AF509054_1\|; |
| \|28849427\|gb\|AAO52896.1\|AF509053_1\|; | | \|28849425\|gb\|AAO52895.1\|AF509052_1\|; |
| \|28849423\|gb\|AAO52894.1\|AF509051_1\|; | | \|28849421\|gb\|AAO52893.1\|AF509050_1\|; |
| \|28849419\|gb\|AAO52892.1\|AF509049_1\|; | | \|28849417\|gb\|AAO52891.1\|AF509048_1\|; |
| \|28849415\|gb\|AAO52890.1\|AF509047_1\|; | | \|28849413\|gb\|AAO52889.1\|AF509046_1\|; |
| \|28849411\|gb\|AAO52888.1\|AF509045_1\|; | | \|28849407\|gb\|AAO52886.1\|AF509043_1\|; |
| \|28849405\|gb\|AAO52885.1\|AF509042_1\|; | | \|28849403\|gb\|AAO52884.1\|AF509041_1\|; |
| \|28849401\|gb\|AAO52883.1\|AF509040_1\|; | | \|5732407\|gb\|AAD49083.1\|AF156465_2\|; |
| \|5732425\|gb\|AAD49095.1\|AF156471_2\|; | | \|5732413\|gb\|AAD49087.1\|AF156467_2\|; |
| \|5732410\|gb\|AAD49085.1\|AF156466_2\|; | | \|5732404\|gb\|AAD49081.1\|AF156464_2\|; |
| \|5732401\|gb\|AAD49079.1\|AF156463_2\|; | | \|5732398\|gb\|AAD49077.1\|AF156462_2\|; |
| \|5732395\|gb\|AAD49075.1\|AF156461_2\|; | | \|5732392\|gb\|AAD49073.1\|AF156460_2\|; |
| \|5732389\|gb\|AAD49071.1\|AF156459_2\|; | | \|5732386\|gb\|AAD49069.1\|AF156458_2\|; |
| \|324263\|gb\|AAA43254.1\|; | \|37933077\|gb\|AAO46713.1\|; | \|37933074\|gb\|AAO46711.1\|; |
| \|37933071\|gb\|AAO46709.1\|; | \|37933068\|gb\|AAO46707.1\|; | \|37933065\|gb\|AAO46705.1\|; |
| \|37933062\|gb\|AAO46703.1\|; | \|37933059\|gb\|AAO46701.1\|; | \|37933056\|gb\|AAO46699.1\|; |
| \|37933053\|gb\|AAO46697.1\|; | \|37933050\|gb\|AAO46695.1\|; | \|37933047\|gb\|AAO46693.1\|; |
| \|37933044\|gb\|AAO46691.1\|; | \|37933041\|gb\|AAO46689.1\|; | \|37933038\|gb\|AAO46687.1\|; |
| \|37933035\|gb\|AAO46685.1\|; | \|37933032\|gb\|AAO46683.1\|; | \|37933029\|gb\|AAO46681.1\|; |
| \|37933026\|gb\|AAO46679.1\|; | \|37933023\|gb\|AAO46677.1\|; | \|37933020\|gb\|AAO46675.1\|; |
| \|37933017\|gb\|AAO46673.1\|; | \|37933014\|gb\|AAO46671.1\|; | \|37933011\|gb\|AAO46669.1\|; |
| \|37933008\|gb\|AAO46667.1\|; | \|37933005\|gb\|AAO46665.1\|; | \|37933002\|gb\|AAO46663.1\|; |
| \|37932999\|gb\|AAO46661.1\|; | \|37932996\|gb\|AAO46659.1\|; | \|37932993\|gb\|AAO46657.1\|; |
| \|37932990\|gb\|AAO46655.1\|; | \|37932987\|gb\|AAO46653.1\|; | \|37932984\|gb\|AAO46651.1\|; |
| \|37785163\|gb\|AAO46420.1\|; | \|37785160\|gb\|AAO46418.1\|; | \|37785157\|gb\|AAO46416.1\|; |
| \|37785154\|gb\|AAO46414.1\|; | \|37785151\|gb\|AAO46412.1\|; | \|37785145\|gb\|AAO46408.1\|; |
| \|37785142\|gb\|AAO46406.1\|; | \|37785139\|gb\|AAO46404.1\|; | \|37785136\|gb\|AAO46402.1\|; |
| \|37785133\|gb\|AAO46400.1\|; | \|37785130\|gb\|AAO46398.1\|; | \|37785127\|gb\|AAO46396.1\|; |
| \|37785124\|gb\|AAO46394.1\|; | \|37785121\|gb\|AAO46392.1\|; | \|37785118\|gb\|AAO46390.1\|; |
| \|37785115\|gb\|AAO46388.1\|; | \|37785112\|gb\|AAO46386.1\|; | \|37785109\|gb\|AAO46384.1\|; |
| \|37785106\|gb\|AAO46382.1\|; | \|37785103\|gb\|AAO46380.1\|; | \|37785100\|gb\|AAO46378.1\|; |
| \|37785097\|gb\|AAO46376.1\|; | \|37785094\|gb\|AAO46374.1\|; | \|37785091\|gb\|AAO46372.1\|; |
| \|37785088\|gb\|AAO46370.1\|; | \|37785085\|gb\|AAO46368.1\|; | \|37785082\|gb\|AAO46366.1\|; |
| \|37785079\|gb\|AAO46364.1\|; | \|37785076\|gb\|AAO46362.1\|; | \|37785073\|gb\|AAO46360.1\|; |
| \|37785070\|gb\|AAO46358.1\|; | \|37785067\|gb\|AAO46356.1\|; | \|37785064\|gb\|AAO46354.1\|; |

| M1 proteins |||
|---|---|---|
| \|37785061\|gb\|AAO46352.1\|; | \|37785058\|gb\|AAO46350.1\|; | \|37785055\|gb\|AAO46348.1\|; |
| \|37785053\|gb\|AAO46347.1\|; | \|37785049\|gb\|AAO46344.1\|; | \|37785046\|gb\|AAO46342.1\|; |
| \|13925107\|gb\|AAK49251.1\|AF255374__1\|; | \|324383\|gb\|AAA43336.1\|; | \|324322\|gb\|AAA43294.1\|; |
| \|325068\|gb\|AAA43674.1\|; | \|324395\|gb\|AAA43344.1\|; | \|324371\|gb\|AAA43316.1\|; \|324334\|gb\|AAA43302.1\|; |
| \|324316\|gb\|AAA43290.1\|; | \|324310\|gb\|AAA43286.1\|; | \|324299\|gb\|AAA43277.1\|; |
| \|11065886\|gb\|AAG28376.1\|AF188004__1\|; | | \|11065883\|gb\|AAG28374.1\|AF188003__1\|; |
| \|483855\|gb\|AAC79577.1\|; | \|2833661\|gb\|AAC34265.1\|; | \|73665375\|gb\|AAZ79394.1\|; |
| \|30025987\|gb\|AAP04510.1\|; | \|66734259\|gb\|AAY53536.1\|; | \|37785148\|gb\|AAO46410.1\|; |
| \|7429156\|pir.parallel.PN0086\|; | \|58618460\|gb\|AAW80728.1\|; | \|58618458\|gb\|AAW80727.1\|; |
| \|13925103\|gb\|AAK49249.1\|AF255373__1\|; | | \|50365716\|gb\|AAT76159.1\|; |
| \|18140844\|gb\|AAL60445.1\|AF398876__1\|; | \|20065772\|gb\|AAM09298.1\|; | \|20065769\|gb\|AAM09296.1\|; |
| \|324406\|gb\|AAA43351.1\|; | \|324398\|gb\|AAA43347.1\|; \|324392\|gb\|AAA43342.1\|; | \|324389\|gb\|AAA43340.1\|; |
| \|324386\|gb\|AAA43338.1\|; | \|324380\|gb\|AAA43334.1\|; \|324377\|gb\|AAA43332.1\|; | \|324374\|gb\|AAA43318.1\|; |
| \|324344\|gb\|AAA43307.1\|; | \|324331\|gb\|AAA43300.1\|; \|324328\|gb\|AAA43298.1\|; | \|324319\|gb\|AAA43292.1\|; |
| \|324313\|gb\|AAA43288.1\|; | \|324307\|gb\|AAA43282.1\|; | \|324304\|gb\|AAA43280.1\|; |
| \|27596998\|ref\|NP__775536.1\|; | \|61612084\|gb\|AAX47287.1\|; | \|63054907\|gb\|AAY28990.1\|; |
| \|60473\|emb\|CAA30892.1\|; | \|60470\|emb\|CAA30890.1\|; | \|60467\|emb\|CAA30888.1\|; |
| \|60464\|emb\|CAA30886.1\|; | \|60461\|emb\|CAA30884.1\|; | \|60458\|emb\|CAA30882.1\|; |
| \|45124752\|emb\|CAF33014.1\|; | \|94145\|pir.parallel.JN0392\|; | \|75117\|pir.parallel.MFIV1K\|; |
| \|7444522\|pir.parallel.T09279\|; | \|77195\|pir.parallel.S04050\|; | \|77193\|pir.parallel.S04052\|; |
| \|77191\|pir.parallel.S04058\|; | \|77189\|pir.parallel.S04056\|; | \|56548894\|gb\|AAV97612.1\|; |
| \|56548892\|gb\|AAV97611.1\|; | \|56548890\|gb\|AAV97610.1\|; | \|56548888\|gb\|AAV97609.1\|; |
| \|58618456\|gb\|AAW80726.1\|; | \|51094108\|gb\|AAS89185.2\|; | \|51859837\|gb\|AAU11202.1\|; |
| \|51859834\|gb\|AAU11200.1\|; | \|51859831\|gb\|AAU11198.1\|; | \|51859825\|gb\|AAU11194.1\|; |
| \|51859822\|gb\|AAU11192.1\|; | \|51859819\|gb\|AAU11190.1\|; | \|51859816\|gb\|AAU11188.1\|; |
| \|51859813\|gb\|AAU11186.1\|; | \|51859810\|gb\|AAU11184.1\|; | \|51859807\|gb\|AAU11182.1\|; |
| \|51859804\|gb\|AAU11180.1\|; | \|51859801\|gb\|AAU11178.1\|; | \|51859798\|gb\|AAU11176.1\|; |
| \|51859792\|gb\|AAU11172.1\|; | \|51859789\|gb\|AAU11170.1\|; | \|51859786\|gb\|AAU11168.1\|; |
| \|51859783\|gb\|AAU11166.1\|; | | \|33318239\|gb\|AAQ04993.1\|AF508704__1\|; |
| \|33318237\|gb\|AAQ04992.1\|AF508703__1\|; | | \|33318235\|gb\|AAQ04991.1\|AF508702__1\|; |
| \|33318233\|gb\|AAQ04990.1\|AF508701__1\|; | | \|33318231\|gb\|AAQ04989.1\|AF508700__1\|; |
| \|33318229\|gb\|AAQ04988.1\|AF508699__1\|; | | \|33318227\|gb\|AAQ04987.1\|AF508698__1\|; |
| \|33318225\|gb\|AAQ04986.1\|AF508697__1\|; | | \|33318223\|gb\|AAQ04985.1\|AF508696__1\|; |
| \|33318221\|gb\|AAQ04984.1\|AF508695__1\|; | | \|33318219\|gb\|AAQ04983.1\|AF508694__1\|; |
| \|33318217\|gb\|AAQ04982.1\|AF508693__1\|; | | \|33318215\|gb\|AAQ04981.1\|AF508692__1\|; |
| \|33318213\|gb\|AAQ04980.1\|AF508691__1\|; | | \|33318207\|gb\|AAQ04977.1\|AF508688__1\|; |
| \|33318205\|gb\|AAQ04976.1\|AF508687__1\|; | | \|33318199\|gb\|AAQ04973.1\|AF508684__1\|; |
| \|41207456\|gb\|AAR99627.1\|; | | \|29539573\|gb\|AAO88261.1\|AF342818__1\|; |
| \|14587042\|gb\|AAK70447.1\|AF386772__1\|; | | \|14587039\|gb\|AAK70445.1\|AF386771__1\|; |
| \|14587036\|gb\|AAK70443.1\|AF386770__1\|; | | \|14587033\|gb\|AAK70441.1\|AF386769__1\|; |
| \|14587030\|gb\|AAK70439.1\|AF386768__1\|; | | \|14587027\|gb\|AAK70437.1\|AF386767__1\|; |
| \|14587024\|gb\|AAK70435.1\|AF386766__1\|; | | \|14587021\|gb\|AAK70433.1\|AF386765__1\|; |
| \|27462132\|gb\|AAO15336.1\|AF225529__1\|; | | \|27462129\|gb\|AAO15334.1\|AF225528__1\|; |
| \|27462126\|gb\|AAO15332.1\|AF225527__1\|; | | \|27462123\|gb\|AAO15330.1\|AF225526__1\|; |
| \|21693175\|gb\|AAM75161.1\|AF389121__1\|; | \|14009743\|gb\|AAK51748.1\|; | \|14009740\|gb\|AAK51746.1\|; |
| \|14009737\|gb\|AAK51744.1\|; | \|14009734\|gb\|AAK51742.1\|; | \|14009731\|gb\|AAK51740.1\|; |
| \|14009728\|gb\|AAK51738.1\|; | \|14009725\|gb\|AAK51736.1\|; | \|14009722\|gb\|AAK51734.1\|; |
| \|14009719\|gb\|AAK51732.1\|; | \|14009716\|gb\|AAK51730.1\|; | \|4097640\|gb\|AAD00149.1\|; |
| \|4097637\|gb\|AAD00147.1\|; | \|4097634\|gb\|AAD00145.1\|; | \|4097631\|gb\|AAD00143.1\|; |
| \|4097628\|gb\|AAD00141.1\|; | \|4097625\|gb\|AAD00139.1\|; | \|4097622\|gb\|AAD00137.1\|; |
| \|4097619\|gb\|AAD00135.1\|; | \|4097616\|gb\|AAD00133.1\|; | \|4097613\|gb\|AAD00131.1\|; |
| \|4097610\|gb\|AAD00129.1\|; | \|3929612\|gb\|AAC80167.1\|; | \|3929609\|gb\|AAC80165.1\|; |
| \|3929606\|gb\|AAC80163.1\|; | \|3929603\|gb\|AAC80161.1\|; | \|3929600\|gb\|AAC80159.1\|; |
| \|3929597\|gb\|AAC80157.1\|; | \|3929594\|gb\|AAC80155.1\|; | \|3722202\|gb\| AAC63485.1\|; |
| \|3722199\|gb\|AAC63483.1\|; | \|3722196\|gb\|AAC63481.1\|; | \|3722193\|gb\|AAC63479.1\|; |
| \|3414662\|gb\|AAC31296.1\|; | \|3414659\|gb\|AAC31294.1\|; | \|3414653\|gb\|AAC31290.1\|; |
| \|3414650\|gb\|AAC31288.1\|; | \|3414647\|gb\|AAC31286.1\|; | \|3414635\|gb\|AAC31278.1\|; |
| \|3414629\|gb\|AAC31274.1\|; | \|3414626\|gb\|AAC31272.1\|; | \|60818\|emb\|CAA41928.1\|; |
| \|75118\|pir.parallel.MFIV1F\|; | \|235419\|gb\|AAB19773.1\|; | \|138819\|sp\|P05777\|VMT1__IAWIL\|; |
| \|138817\|sp\|P03485\|VMT1__IAPUE\|; | \|324260\|gb\|AAA43252.1\|; | \|324258\|gb\|AAA431251.1\|; |
| \|138812\|sp\|P05775\|VMT1__IAFPW\|; | \|1912412\|gb\|AAB50992.1\|; | \|1912409\|gb\|AAB50990.1\|; |
| \|1912406\|gb\|AAB50988.1\|; | \|1912403\|gb\|AAB50986.1\|; | \|1912400\|gb\|AAB50984.1\|; |
| \|407933\|gb\|AAB39915.1\|; | \|406039\|gb\|AAA67337.1\|; \|325082\|gb\|AAA43682.1\|; | \|324364\|gb\|AAA43313.1\|; |
| \|324266\|gb\|AAA43256.1\|; | \|323978\|gb\|AAA43092.1\|; | \|62901345\|sp\|Q77Y95\|VMT1__IAHO3\|; |
| \|60416244\|sp\|P69276\|VMT1__IASIN\|; | | \|60416243\|sp\|P69275\|VMT1__IAFOW\|; |
| \|54039855\|sp\|P63234\|VMT1__IAPOC\|; | | \|549378\|sp\|P35937\|VMT1__IAUSS\|; |
| \|549377\|sp\|P36347\|VMT1__IACKB\|; | | \|138820\|sp\|P05776\|VMT1__IAZI1\|; |
| \|138815\|sp\|P08381\|VMT1__IAMAN\|; | | \|138808\|sp\|P03487\|VMT1__IABAN\|; |
| \|138807\|sp\|P21429\|VMT1__IAANN\|; | | \|138813\|sp\|P26127\|VMT1__IALE1\|; |
| \|54039857\|sp\|P67865\|VMT1__IALE3\|; | | \|54039856\|sp\|P67864\|VMT1__IALE2\|; |
| \|138811\|sp\|P03488\|VMT1__IAFPR\|; | \|414307\|gb\|AAA91325.1\|; | \|414304\|gb\|AAA91323.1\|; |
| \|13182927\|gb\|AAK14989.1\|AF231361__2\|; | | \|13182921\|gb\|AAK14985.1\|AF231359__2\|; |
| \|8307813\|gb\|AAF74336.1\|AF084284__1\|; | | \|8307810\|gb\|AAF74334.1\|AF084283__1\|; |
| \|8307807\|gb\|AAF74332.1\|AF084282__1\|; | | \|4584939\|gb\|AAD25211.1\|AF073200__1\|; |
| \|71013510\|dbj\|BAE07204.1\|; | \|9857035\|emb\|CAC04083.1\|; | \|9857038\|emb\|CAC04085.1\|; \|; |
| \|54299846\|gb\|AAV32646.1\|; | \|54299832\|gb\|AAV32638.1\|; | \|52078188\|gb\|AAU25869.1\|; |
| \|52078168\|gb\|AAU25858.1\|; | \|52078150\|gb\|AAU25848.1\|; | \|30522966\|gb\|AAO65611.1\|; |

| M1 proteins | | |
|---|---|---|
| \|8486123\|ref\|NP_040978.1\|; | \|58531182\|dbj\|BAD89349.1\|; | \|58531164\|dbj\|BAD89339.1\|; |
| \|58531146\|dbj\|BAD89329.1\|; | \|58531128\|dbj\|BAD89319.1\|; | \|58531096\|dbj\|BAD89309.1\|; |
| \|42521294\|gb\|AAS18237.1\|; | \|38524570\|dbj\|BAD02365.1\|; | \|38524552\|dbj\|BAD02355.1\|; |
| \|4584954\|gb\|AAD25221.1\|AF073205_1\|; | | \|4584951\|gb\|AAD25219.1\|AF073204_1\|; |
| \|4584948\|gb\|AAD25217.1\|AF073203_1\|; | | \|4584945\|gb\|AAD25215.1\|AF073202_1\|; |
| \|4584942\|gb\|AAD25213.1\|AF073201_1\|; | | \|4584936\|gb\|AAD25209.1\|AF073199_1\|; |
| \|4584933\|gb\|AAD25207.1\|AF073198_1\|; | | \|4584930\|gb\|AAD25205.1\|AF073197_1\|; |
| \|4584927\|gb\|AAD25203.1\|AF073196_1\|; | | \|4584924\|gb\|AAD25201.1\|AF073195_1\|; |
| \|4584921\|gb\|AAD25199.1\|AF073194_1\|; | | \|4584918\|gb\|AAD25197.1\|AF073193_1\|; |
| \|4584915\|gb\|AAD25195.1\|AF073192_1\|; | | \|4584912\|gb\|AAD25193.1\|AF073191_1\|; |
| \|4584909\|gb\|AAD25191.1\|AF073190_1\|; | \|4584906\|gb\|AAD25189.1\|AF073189_1\|; | |
| \|4584903\|gb\|AAD25187.1\|AF073188_1\|; | | \|4584900\|gb\|AAD25185.1\|AF073187_1\|; |
| \|4584897\|gb\|AAD25183.1\|AF073186_1\|; | | \|4584894\|gb\|AAD25181.1\|AF073185_1\|; |
| \|4584891\|gb\|AAD25179.1\|AF073184_1\|; | | \|4584888\|gb\|AAD25177.1\|AF073183_1\|; |
| \|4584885\|gb\|AAD25175.1\|AF073182_1\|; | | \|4584882\|gb\|AAD25173.1\|AF073181_1\|; |
| \|4584879\|gb\|AAD25171.1\|AF073180_1\|; | \|77917338\|gb\|ABB05217.1\|; | \|77917319\|gb\|ABB05206.1\|; |
| \|77917300\|gb\|ABB05195.1\|; | \|77869490\|gb\|ABB05184.1\|; | \|77863493\|gb\|ABB05006.1\|; |
| \|77863474\|gb\|ABB04995.1\|; | \|77863455\|gb\|ABB04984.1\|; | \|77863436\|gb\|ABB04973.1\|; |
| \|77863417\|gb\|ABB04962.1\|; | \|77863398\|gb\|ABB04951.1\|; | \|77863379\|gb\|ABB04940.1\|; |
| \|77863360\|gb\|ABB04929.1\|; | \|77863341\|gb\|ABB04918.1\|; | \|77863322\|gb\|ABB04907.1\|; |
| \|77861869\|gb\|ABB04372.1\|; | \|77861850\|gb\|ABB04361.1\|; | \|77861831\|gb\|ABB04350.1\|; |
| \|77861812\|gb\|ABB04339.1\|; | \|77861793\|gb\|ABB04328.1\|; | \|77861774\|gb\|ABB04317.1\|; |
| \|77861755\|gb\|ABB04306.1\|; | \|77861736\|gb\|ABB04295.1\|; | \|77861717\|gb\|ABB04284.1\|; |
| \|77747462\|gb\|ABB03146.1\|; | \|77747443\|gb\|ABB03135.1\|; | \|77747424\|gb\|ABB03124.1\|; |
| \|77747404\|gb\|ABB03113.1\|; | \|77747385\|gb\|ABB03102.1\|; | \|77747366\|gb\|ABB03091.1\|; |
| \|77747347\|gb\|ABB03080.1\|; | \|77747328\|gb\|ABB03069.1\|; | \|77747307\|gb\|ABB03058.1\|; |
| \|77747288\|gb\|ABB03047.1\|; | \|77747269\|gb\|ABB03036.1\|; | \|77747250\|gb\|ABB03025.1\|; |
| \|77747231\|gb\|ABB03014.1\|; | \|77747212\|gb\|ABB03003.1\|; | \|77747193\|gb\|ABB02992.1\|; |
| \|77747174\|gb\|ABB02981.1\|; | \|77747153\|gb\|ABB02970.1\|; | \|77747134\|gb\|ABB02959.1\|; |
| \|77747115\|gb\|ABB02948.1\|; | \|77747096\|gb\|ABB02937.1\|; | \|77747075\|gb\|ABB02925.1\|; |
| \|77747056\|gb\|ABB02914.1\|; | \|77747037\|gb\|ABB02903.1\|; | \|77746991\|gb\|ABB02892.1\|; |
| \|77746972\|gb\|ABB02881.1\|; | \|77746953\|gb\|ABB02870.1\|; | \|77746934\|gb\|ABB02859.1\|; |
| \|77746915\|gb\|ABB02848.1\|; | \|77746894\|gb\|ABB02837.1\|; | \|77746875\|gb\|ABB02826.1\|; |
| \|77746856\|gb\|ABB02815.1\|; | \|77746837\|gb\|ABB02804.1\|; | \|77746818\|gb\|ABB02793.1\|; |
| \|77746799\|gb\|ABB02782.1\|; | \|77543685\|gb\|ABA87254.1\|; | \|77543665\|gb\|ABA87243.1\|; |
| \|77543645\|gb\|ABA87232.1\|; | \|77543363\|gb\|ABA87092.1\|; | \|77543344\|gb\|ABA87081.1\|; |
| \|77543300\|gb\|ABA87058.1\|; | \|77543244\|gb\|ABA87046.1\|; | \|76464351\|gb\|ABA43337.1\|; |
| \|76453795\|gb\|ABA43201.1\|; | \|76446822\|gb\|ABA43190.1\|; | \|76446801\|gb\|ABA43179.1\|; |
| \|76446428\|gb\|ABA43168.1\|; | \|76446386\|gb\|ABA42979.1\|; | \|76446314\|gb\|ABA42940.1\|; |
| \|76446295\|gb\|ABA42929.1\|; | \|76443529\|gb\|ABA42576.1\|; | \|76443510\|gb\|ABA42565.1\|; |
| \|76443491\|gb\|ABA42554.1\|; | \|76443472\|gb\|ABA42543.1\|; | \|76443453\|gb\|ABA42532.1\|; |
| \|76443434\|gb\|ABA42521.1\|; | \|76443415\|gb\|ABA42510.1\|; | \|76443396\|gb\|ABA42499.1\|; |
| \|76443377\|gb\|ABA42488.1\|; | \|76443358\|gb\|ABA42477.1\|; | \|76443339\|gb\|ABA42466.1\|; |
| \|76443320\|gb\|ABA42455.1\|; | \|76443271\|gb\|ABA42444.1\|; | \|76443252\|gb\|ABA42413.1\|; |
| \|76443233\|gb\|ABA42402.1\|; | \|76443214\|gb\|ABA42391.1\|; | \|76443195\|gb\|ABA42380.1\|; |
| \|76443176\|gb\|ABA42369.1\|; | \|76440841\|gb\|ABA42358.1\|; | \|76426669\|gb\|ABA42347.1\|; |
| \|76418549\|gb\|ABA42336.1\|; | \|76411033\|gb\|ABA42325.1\|; | \|76410401\|gb\|ABA42314.1\|; |
| \|76403102\|gb\|ABA42303.1\|; | \|76381504\|gb\|ABA42292.1\|; | \|76374057\|gb\|ABA42281.1\|; |
| \|76366071\|gb\|ABA42270.1\|; | \|76366052\|gb\|ABA42259.1\|; | \|76366033\|gb\|ABA42248.1\|; |
| \|76366014\|gb\|ABA42237.1\|; | \|75750347\|gb\|ABA26800.1\|; | \|75750328\|gb\|ABA26789.1\|; |
| \|75750309\|gb\|ABA26778.1\|; | \|75750290\|gb\|ABA26767.1\|; | \|75750271\|gb\|ABA26756.1\|; |
| \|75750252\|gb\|ABA26745.1\|; | \|75750233\|gb\|ABA26734.1\|; | \|75750214\|gb\|ABA26723.1\|; |
| \|75750195\|gb\|ABA26712.1\|; | \|75750176\|gb\|ABA26701.1\|; | \|72623449\|gb\|AAZ74618.1\|; |
| \|75218743\|gb\|ABA18168.1\|; | \|75217099\|gb\|ABA18157.1\|; | \|75216125\|gb\|ABA18146.1\|; |
| \|75215940\|gb\|ABA18135.1\|; | \|75215199\|gb\|ABA18124.1\|; | \|75214317\|gb\|ABA18113.1\|; |
| \|75212621\|gb\|ABA18038.1\|; | \|75206495\|gb\|ABA18027.1\|; | \|75181140\|gb\|ABA12782.1\|; |
| \|75181097\|gb\|ABA12774.1\|; | \|75180915\|gb\|ABA12763.1\|; | \|75180819\|gb\|ABA12752.1\|; |
| \|75180514\|gb\|ABA12741.1\|; | \|75172966\|gb\|ABA12730.1\|; | \|75171345\|gb\|ABA12718.1\|; |
| \|75171062\|gb\|ABA12708.1\|; | \|75168355\|gb\|ABA12697.1\|; | \|74477288\|gb\|ABA08520.1\|; |
| \|74477269\|gb\|ABA08509.1\|; | \|74477248\|gb\|ABA08498.1\|; | \|74477229\|gb\|ABA08487.1\|; |
| \|74477210\|gb\|ABA08476.1\|; | \|74477191\|gb\|ABA08465.1\|; | \|74422755\|gb\|ABA06543.1\|; |
| \|74422586\|gb\|ABA06511.1\|; | \|73919152\|ref\|YP_308841.1\|; | \|32141423\|ref\|NP_859036.1\|; |
| \|73765595\|gb\|AAZ85127.1\|; | \|73763197\|gb\|AAZ83978.1\|; | \|73762504\|gb\|AAZ83689.1\|; |
| \|73762293\|gb\|AAZ83650.1\|; | \|73761787\|gb\|AAZ83383.1\|; | \|73761720\|gb\|AAZ83372.1\|; |
| \|73761598\|gb\|AAZ83324.1\|; | \|73761579\|gb\|AAZ83313.1\|; | \|73761560\|gb\|AAZ83300.1\|; |
| \|73761522\|gb\|AAZ83278.1\|; | \|73761499\|gb\|AAZ83267.1\|; | \|73761476\|gb\|AAZ83254.1\|; |
| \|73761457\|gb\|AAZ83243.1\|; | \|73666615\|gb\|AAZ80031.1\|; | \|73666596\|gb\|AAZ80019.1\|; |
| \|73666577\|gb\|AAZ80008.1\|; | \|73666558\|gb\|AAZ79997.1\|; | \|73666539\|gb\|AAZ79986.1\|; |
| \|73665974\|gb\|AAZ79975.1\|; | \|73665924\|gb\|AAZ79964.1\|; | \|73665876\|gb\|AAZ79946.1\|; |
| \|73665868\|gb\|AAZ79942.1\|; | \|73665830\|gb\|AAZ79630.1\|; | \|73665827\|gb\|AAZ79628.1\|; |
| \|73665806\|gb\|AAZ79616.1\|; | \|73665787\|gb\|AAZ79605.1\|; | \|73665768\|gb\|AAZ79594.1\|; |
| \|73665749\|gb\|AAZ79583.1\|; | \|73665730\|gb\|AAZ79572.1\|; | \|73665711\|gb\|AAZ79561.1\|; |
| \|73665692\|gb\|AAZ79550.1\|; | \|73665673\|gb\|AAZ79539.1\|; | \|73665654\|gb\|AAZ79528.1\|; |
| \|73665635\|gb\|AAZ79517.1\|; | \|73665612\|gb\|AAZ79506.1\|; | \|67644047\|gb\|AAY78940.1\|; |
| \|62198978\|gb\|AAX76734.1\|; | \|72602389\|gb\|AAZ74607.1\|; | \|72602370\|gb\|AAZ74596.1\|; |
| \|72602351\|gb\|AAZ74585.1\|; | \|72602238\|gb\|AAZ74574.1\|; | \|72598156\|gb\|AAZ74563.1\|; |
| \|72597908\|gb\|AAZ74552.1\|; | \|72582113\|gb\|AAZ74541.1\|; | \|72580904\|gb\|AAZ74530.1\|; |

| M1 proteins | | |
|---|---|---|
| \|72578614\|gb\|AAZ74519.1\|; | \|72572288\|gb\|AAZ74508.1\|; | \|72572210\|gb\|AAZ74497.1\|; |
| \|72568982\|gb\|AAZ74486.1\|; | \|72565898\|gb\|AAZ74475.1\|; | \|72562517\|gb\|AAZ74464.1\|; |
| \|72556623\|gb\|AAZ74453.1\|; | \|72554370\|gb\|AAZ74442.1\|; | \|72552876\|gb\|AAZ74431.1\|; |
| \|72552072\|gb\|AAZ74420.1\|; | \|72549571\|gb\|AAZ74409.1\|; | \|72545851\|gb\|AAZ74398.1\|; |
| \|72545117\|gb\|AAZ74387.1\|; | \|72542981\|gb\|AAZ74375.1\|; | \|72539892\|gb\|AAZ74364.1\|; |
| \|72539853\|gb\|AAZ74353.1\|; | \|71000195\|dbj\|BAE07159.1\|; | \|71842589\|gb\|AAZ43406.1\|; |
| \|71842570\|gb\|AAZ43395.1\|; | \|71842551\|gb\|AAZ43384.1\|; | \|71842528\|gb\|AAZ43371.1\|; |
| \|71571147\|gb\|AAZ38651.1\|; | \|71568545\|gb\|AAZ38639.1\|; | \|71564882\|gb\|AAZ38628.1\|; |
| \|71564863\|gb\|AAZ38617.1\|; | \|71564844\|gb\|AAZ38606.1\|; | \|71564825\|gb\|AAZ38595.1\|; |
| \|71564806\|gb\|AAZ38584.1\|; | \|71564787\|gb\|AAZ38573.1\|; | \|71564768\|gb\|AAZ38562.1\|; |
| \|71564749\|gb\|AAZ38551.1\|; | \|71564730\|gb\|AAZ38540.1\|; | \|71564711\|gb\|AAZ38529.1\|; |
| \|71564692\|gb\|AAZ38518.1\|; | \|71564673\|gb\|AAZ38507.1\|; | \|71564654\|gb\|AAZ38496.1\|; |
| \|71564635\|gb\|AAZ38485.1\|; | \|71564616\|gb\|AAZ38474.1\|; | \|71564597\|gb\|AAZ38463.1\|; |
| \|70907642\|gb\|AAX56531.2\|; | \|62198870\|gb\|AAX76674.1\|; | \|68525442\|gb\|AAY98771.1\|; |
| \|68510079\|gb\|AAY98407.1\|; | \|68510060\|gb\|AAY98397.1\|; | \|68510041\|gb\|AAY98387.1\|; |
| \|68510010\|gb\|AAY98377.1\|; | \|68509989\|gb\|AAY98367.1\|; | \|68509957\|gb\|AAY98357.1\|; |
| \|68509895\|gb\|AAY98340.1\|; | \|68509732\|gb\|AAY98330.1\|; | \|68509376\|gb\|AAY98320.1\|; |
| \|68509334\|gb\|AAY98248.1\|; | \|68509314\|gb\|AAY98238.1\|; | \|68509295\|gb\|AAY98228.1\|; |
| \|68509275\|gb\|AAY98218.1\|; | \|68509251\|gb\|AAY98208.1\|; | \|68509226\|gb\|AAY98197.1\|; |
| \|68509209\|gb\|AAY98188.1\|; | \|68509188\|gb\|AAY98178.1\|; | \|68509170\|gb\|AAY98168.1\|; |
| \|68509152\|gb\|AAY98158.1\|; | \|68509134\|gb\|AAY98148.1\|; | \|68509115\|gb\|AAY98138.1\|; |
| \|68509097\|gb\|AAY98128.1\|; | \|68509079\|gb\|AAY98118.1\|; | \|68509061\|gb\|AAY98108.1\|; |
| \|68509043\|gb\|AAY98098.1\|; | \|68509011\|gb\|AAY98088.1\|; | \|68508930\|gb\|AAY98078.1\|; |
| \|68508893\|gb\|AAY98068.1\|; | \|68508816\|gb\|AAY98058.1\|; | \|68508600\|gb\|AAY98048.1\|; |
| \|68508515\|gb\|AAY98038.1\|; | \|62199032\|gb\|AAX76764.1\|; | \|62198816\|gb\|AAX76644.1\|; |
| \|61970920\|gb\|AAX57935.1\|; | \|61970722\|gb\|AAX57825.1\|; | \|61927526\|gb\|AAX56471.1\|; |
| \|59896446\|gb\|AAX11576.1\|; | \|68161822\|emb\|CAJ01905.1\|; | \|67062583\|gb\|AAY64403.1\|; |
| \|67062042\|gb\|AAY64393.1\|; | \|67061886\|gb\|AAY64383.1\|; | \|67061090\|gb\|AAY64373.1\|; |
| \|67060408\|gb\|AAY64363.1\|; | \|67060167\|gb\|AAY64353.1\|; | \|67059535\|gb\|AAY64343.1\|; |
| \|67058967\|gb\|AAY64333.1\|; | \|67058904\|gb\|AAY64323.1\|; | \|67058349\|gb\|AAY64313.1\|; |
| \|67058331\|gb\|AAY64303.1\|; | \|67058313\|gb\|AAY64293.1\|; | \|67058295\|gb\|AAY64283.1\|; |
| \|67058277\|gb\|AAY64273.1\|; | \|67057698\|gb\|AAY64263.1\|; | \|67051336\|gb\|AAY64253.1\|; |
| \|67049849\|gb\|AAY64243.1\|; | \|67045888\|gb\|AAY64233.1\|; | \|67045467\|gb\|AAY64223.1\|; |
| \|67044510\|gb\|AAY64213.1\|; | \|67044334\|gb\|AAY64203.1\|; | \|67044258\|gb\|AAY64193.1\|; |
| \|67044158\|gb\|AAX57865.2\|; | \|66947416\|gb\|AAY59036.1\|; | \|66475120\|gb\|AAY47086.1\|; |
| \|66475102\|gb\|AAY47076.1\|; | \|66475058\|gb\|AAY47053.1\|; | \|66474990\|gb\|AAY47024.1\|; |
| \|66473597\|gb\|AAY46437.1\|; | \|66473579\|gb\|AAY46427.1\|; | \|66473561\|gb\|AAY46417.1\|; |
| \|66473491\|gb\|AAY46392.1\|; | \|66473469\|gb\|AAY46382.1\|; | \|66473449\|gb\|AAY46372.1\|; |
| \|66356017\|gb\|AAY45647.1\|; | \|66354526\|gb\|AAY44907.1\|; | \|66354508\|gb\|AAY44897.1\|; |
| \|66354010\|gb\|AAY44797.1\|; | \|66353990\|gb\|AAY44786.1\|; | \|66353972\|gb\|AAY44776.1\|; |
| \|66353872\|gb\|AAY44766.1\|; | \|66353854\|gb\|AAY44756.1\|; | \|66346631\|gb\|AAY44662.1\|; |
| \|66346001\|gb\|AAY44652.1\|; | \|66327419\|gb\|AAY44642.1\|; | \|66319001\|gb\|AAY44632.1\|; |
| \|66315204\|gb\|AAY44622.1\|; | \|66303354\|gb\|AAY44611.1\|; | \|3335425\|gb\|AAC32090.1\|; |
| \|3335407\|gb\|AAC32080.1\|; | \|63053665\|gb\|AAY28639.1\|; | \|63029987\|gb\|AAY27864.1\|; |
| \|63053683\|gb\|AAY28649.1\|; | \|63053647\|gb\|AAY28629.1\|; | \|63053629\|gb\|AAY28619.1\|; |
| \|63053611\|gb\|AAY28609.1\|; | \|63053528\|gb\|AAY28592.1\|; | \|63053496\|gb\|AAY28582.1\|; |
| \|63053478\|gb\|AAY28572.1\|; | \|63053459\|gb\|AAY28562.1\|; | \|63047644\|gb\|AAY28552.1\|; |
| \|63038347\|gb\|AAY28542.1\|; | \|63034457\|gb\|AAY28532.1\|; | \|63034439\|gb\|AAY28522.1\|; |
| \|63034224\|gb\|AAY28503.1\|; | \|63034195\|gb\|AAY28406.1\|; | \|63034177\|gb\|AAY28396.1\|; |
| \|63034158\|gb\|AAY28386.1\|; | \|63034140\|gb\|AAY28376.1\|; | \|63034120\|gb\|AAY28365.1\|; |
| \|63034104\|gb\|AAY28356.1\|; | \|63034086\|gb\|AAY28346.1\|; | \|63034068\|gb\|AAY28336.1\|; |
| \|63034050\|gb\|AAY28326.1\|; | \|63034032\|gb\|AAY28316.1\|; | \|63034014\|gb\|AAY28306.1\|; |
| \|63033973\|gb\|AAY28296.1\|; | \|63033955\|gb\|AAY28286.1\|; | \|63033937\|gb\|AAY28276.1\|; |
| \|63033917\|gb\|AAY28266.1\|; | \|63033414\|gb\|AAY28015.1\|; | \|63033396\|gb\|AAY28005.1\|; |
| \|63033377\|gb\|AAY27995.1\|; | \|63031460\|gb\|AAY27960.1\|; | \|63029969\|gb\|AAY27854.1\|; |
| \|63029949\|gb\|AAY27844.1\|; | \|62871285\|gb\|AAY18586.1\|; | \|62871262\|gb\|AAY18565.1\|; |
| \|62870083\|gb\|AAY18197.1\|; | \|62870065\|gb\|AAY18187.1\|; | \|62870047\|gb\|AAY18177.1\|; |
| \|62870029\|gb\|AAY18167.1\|; | \|62870011\|gb\|AAY18157.1\|; | \|62869993\|gb\|AAY18147.1\|; |
| \|62869975\|gb\|AAY18137.1\|; | \|62869957\|gb\|AAY18127.1\|; | \|62869939\|gb\|AAY18117.1\|; |
| \|62869921\|gb\|AAY18107.1\|; | \|62869903\|gb\|AAY18097.1\|; | \|62869884\|gb\|AAY18087.1\|; |
| \|62198924\|gb\|AAX76704.1\|; | \|62198798\|gb\|AAX76634.1\|; | \|62198780\|gb\|AAX76624.1\|; |
| \|61620943\|gb\|AAX47526.1\|; | \|62199014\|gb\|AAX76754.1\|; | |
| \|60683805\|gb\|AAX34062.1\|; | \|59940441\|gb\|AAX12762.1\|; | \|438072\|emb\|CAA81464.1\|; |
| \|40353079\|emb\|CAF02292.1\|; | \|39840728\|emb\|CAC95058.1\|; | \|22859490\|emb\|CAD30544.1\|; |
| \|22859486\|emb\|CAD30542.1\|; | \|22859483\|emb\|CAD30540.1\|; | \|22859480\|emb\|CAD30538.1\|; |
| \|22859477\|emb\|CAD30536.1\|; | \|20068129\|emb\|CAC87410.1\|; | \|20068120\|emb\|CAC87404.1\|; |
| \|20068108\|emb\|CAC87396.1\|; | \|20068105\|emb\|CAC87394.1\|; | \|20068099\|emb\|CAC87390.1\|; |
| \|20068093\|emb\|CAC87386.1\|; | \|19913218\|emb\|CAD20332.1\|; | \|19913212\|emb\|CAD20326.1\|; |
| \|14275729\|emb\|CAC40057.1\|; | \|14275702\|emb\|CAC40043.1\|; | \|12038900\|emb\|CAC19700.1\|; |
| \|9857032\|emb\|CAC04081.1\|; | \|62198996\|gb\|AAX76744.1\|; | \|62198960\|gb\|AAX76724.1\|; |
| \|62198942\|gb\|AAX76714.1\|; | \|62198906\|gb\|AAX76694.1\|; | \|62198888\|gb\|AAX76684.1\|; |
| \|62198852\|gb\|AAX76664.1\|; | \|62198834\|gb\|AAX76654.1\|; | \|61970938\|gb\|AAX57945.1\|; |
| \|61970884\|gb\|AAX57915.1\|; | \|61970866\|gb\|AAX57905.1\|; | \|61970848\|gb\|AAX57895.1\|; |
| \|61970830\|gb\|AAX57885.1\|; | \|61970812\|gb\|AAX57875.1\|; | \|61970776\|gb\|AAX57855.1\|; |
| \|61970758\|gb\|AAX57845.1\|; | \|61970740\|gb\|AAX57835.1\|; | \|61970704\|gb\|AAX57815.1\|; |
| \|61970686\|gb\|AAX57805.1\|; | \|61970668\|gb\|AAX57795.1\|; | \|61970650\|gb\|AAX57785.1\|; |
| \|61970632\|gb\|AAX57775.1\|; | \|61970614\|gb\|AAX57765.1\|; | \|61970596\|gb\|AAX57755.1\|; |

| M1 proteins |
|---|

|61970578|gb|AAX57745.1|; |61970560|gb|AAX57735.1|; |61970540|gb|AAX57724.1|; |61970524|gb|AAX57715.1|; |61970506|gb|AAX57705.1|; |61970488|gb|AAX57695.1|; |61970470|gb|AAX57685.1|; |61970452|gb|AAX57675.1|; |61970434|gb|AAX57665.1|; |61970416|gb|AAX57655.1|; |61970398|gb|AAX57645.1|; |61928202|gb|AAX56601.1|; |61928145|gb|AAX56591.1|; |61928094|gb|AAX56581.1|; |61928048|gb|AAX56571.1|; |61927990|gb|AAX56561.1|; |61927939|gb|AAX56551.1|; |61927891|gb|AAX56541.1|; |61927796|gb|AAX56521.1|; |61927744|gb|AAX56511.1|; |61927695|gb|AAX56501.1|; |61927633|gb|AAX56491.1|; |61927579|gb|AAX56481.1|; |61927471|gb|AAX56461.1|; |61927419|gb|AAX56451.1|; |61927367|gb|AAX56441.1|; |61927319|gb|AAX56431.1|; |61927272|gb|AAX56421.1|; |61927225|gb|AAX56411.1|; |61927170|gb|AAX56401.1|; |61927122|gb|AAX56391.1|; |61927073|gb|AAX56381.1|; |61620994|gb|AAX47536.1|; |61620910|gb|AAX47516.1|; |61104889|gb|AAX38238.1|; |60738750|gb|AAX35872.1|; |60738732|gb|AAX35862.1|; |60738714|gb|AAX35852.1|; |60738696|gb|AAX35842.1|; |60738678|gb|AAX35832.1|; |60738660|gb|AAX35822.1|; |59940533|gb|AAX12812.1|; |59940515|gb|AAX12802.1|; |59940497|gb|AAX12792.1|; |59940479|gb|AAX12782.1|; |59940459|gb|AAX12772.1|; |59940423|gb|AAX12752.1|; |59940405|gb|AAX12742.1|; |59940387|gb|AAX12732.1|; |59896554|gb|AAX11636.1|; |59896536|gb|AAX11626.1|; |59896518|gb|AAX11616.1|; |59896500|gb|AAX11606.1|; |59896482|gb|AAX11596.1|; |59896464|gb|AAX11586.1|; |59896428|gb|AAX11566.1|; |59896410|gb|AAX11556.1|; |59896392|gb|AAX11546.1|; |59896374|gb|AAX11536.1|; |59896356|gb|AAX11526.1|; |59896338|gb|AAX11516.1|; |59896320|gb|AAX11506.1|; |59896302|gb|AAX11496.1|; |59896284|gb|AAX11486.1|; |59896266|gb|AAX11476.1|; |59896248|gb|AAX11466.1|; |59896230|gb|AAX11456.1|; |61970902|gb|AAX57925.1|; |50659954|gb|AAT80681.1|; |55233223|gb|AAV48543.1|; |13383295|dbj|BAB39520.1|; |13383292|dbj|BAB39518.1|; |16076725|gb|AAL14093.1|AF222823_1|; |16076723|gb|AAL14092.1|AF222822_1|; |13182924|gb|AAK14987.1|AF231360_2|; |13182918|gb|AAK14983.1|AF231358_2|; |9887187|gb|AAG01788.1|AF251430_1|; |9887170|gb|AAG01779.1|AF251422_1|; |9887153|gb|AAG01770.1|AF251414_1|; |9887136|gb|AAG01761.1|AF251406_1|; |9887119|gb|AAG01752.1|AF251398_1|; |9887105|gb|AAG01745.1|AF251391_1|; |8452835|gb|AAF75113.1|AF115287_1|; |8452832|gb|AAF75111.1|AF115286_1|; |324357|gb|AAA19197.1|; |324354|gb|AAA19195.1|; |324351|gb|AAA19193.1|; |14278293|pdb|1EA3|; |14278292|pdb|1EA3|; |54039854|sp|P63233|VMT1_IAUDO|; |50234652|gb|AAT70535.1|; |54610025|gb|AAV35110.1|; |19422101|gb|AAL87877.1|AF455687_1|; |19422095|gb|AAL87874.1|AF455684_1|; |19422093|gb|AAL87873.1|AF455683_1|; |226440|prf.parallel.1512373A|; |50234772|gb|AAT70615.1|; |50234766|gb|AAT70611.1|; |50234763|gb|AAT70609.1|; |50234760|gb|AAT70607.1|; |50234757|gb|AAT70605.1|; |50234754|gb|AAT70603.1|; |50234751|gb|AAT70601.1|; |50234748|gb|AAT70599.1|; |50234745|gb|AAT70597.1|; |50234742|gb|AAT70595.1|; |50234739|gb|AAT70593.1|; |50234736|gb|AAT70591.1|; |50234733|gb|AAT70589.1|; |50234724|gb|AAT70583.1|; |50234721|gb|AAT70581.1|; |50234718|gb|AAT70579.1|; |50234715|gb|AAT70577.1|; |50234712|gb|AAT70575.1|; |50234709|gb|AAT70573.1|; |50234706|gb|AAT70571.1|; |50234700|gb|AAT70567.1|; |50234697|gb|AAT70565.1|; |50234688|gb|AAT70559.1|; |50234685|gb|AAT70557.1|; |50234682|gb|AAT70555.1|; |50234679|gb|AAT70553.1|; |50234673|gb|AAT70549.1|; |50234670|gb|AAT70547.1|; |50234667|gb|AAT70545.1|; |50234664|gb|AAT70543.1|; |50234661|gb|AAT70541.1|; |50234658|gb|AAT70539.1|; |50234655|gb|AAT70537.1|; |50234649|gb|AAT70533.1|; |50234646|gb|AAT70531.1|; |50234643|gb|AAT70529.1|; |50234640|gb|AAT70527.1|; |50234637|gb|AAT70525.1|; |50234634|gb|AAT70523.1|; |50234631|gb|AAT70521.1|; |50234628|gb|AAT70519.1|; |50234625|gb|AAT70517.1|; |50234622|gb|AAT70515.1|; |50234619|gb|AAT70513.1|; |50234616|gb|AAT70511.1|; |50234613|gb|AAT70509.1|; |50234610|gb|AAT70507.1|; |50234607|gb|AAT70505.1|; |50234604|gb|AAT70503.1|; |50234600|gb|AAT70500.1|; |34597767|gb|AAQ77440.1|; |34597764|gb|AAQ77438.1|; |34597761|gb|AAQ77436.1|; |34597758|gb|AAQ77434.1|; |34597755|gb|AAQ77432.1|; |21359672|gb|AAM49561.1|AF468843_1|; |21326689|gb|AAL75849.1|; |19422107|gb|AAL87880.1|AF455690_1|; |19422105|gb|AAL87879.1|AF455689_1|; |19422103|gb|AAL87878.1|AF455688_1|; |19422099|gb|AAL87876.1|AF455686_1|; |19422097|gb|AAL87875.1|AF455685_1|; |9863927|gb|AAG01222.1|AF216735_1|; |9863909|gb|AAG01212.1|AF216727_1|; |9863890|gb|AAG01202.1|AF216719_1|; |8515426|gb|AAF75995.1|AF250125_1|; |468299|gb|AAA62336.1|; |468294|gb|AAA62333.1|; |324337|gb|AAA43304.1|; |577471|gb|AAA56808.1|; |577468|gb|AAA56806.1|; |413856|gb|AAA43250.1|; |324408|gb|AAA43352.1|; |324290|gb|AAA43272.1|; |324287|gb|AAA43270.1|; |324284|gb|AAA43268.1|; |324281|gb|AAA43266.1|; |324278|gb|AAA43264.1|; |324275|gb|AAA43262.1|; |324272|gb|AAA43260.1|; |324269|gb|AAA43258.1

| M2 proteins |
|---|

|585311811|dbj|BAD89348.1|; |58531163|dbj|BAD89338.1|; |58531145|dbj|BAD89328.1|; |9049381|dbj|BAA99398.1|; |5764375|gb|AAD51270.1|AF153259_2|; |5764369|gb|AAD51266.1|AF153257_2|; |76443316|gb|ABA42442.1|; |76443313|gb|ABA42440.1|; |76443310|gb|ABA42438.1|; |76443307|gb|ABA42436.1|; |76443304|gb|ABA42434.1|; |21636456|gb|AAM70004.1|AF457712_2|; |21636451|gb|AAM70001.1|AF457710_2|; |21636435|gb|AAM69992.1|AF457703_2|; |21636417|gb|AAM69982.1|AF457695_2|; |21636399|gb|AAM69972.1|AF457687_2|; |21636379|gb|AAM69961.1|AF457678_2|; |9802292|gb|AAF99673.1|AF258523_2|; |9802289|gb|AAF99671.1|AF258522_2|; |5805290|gb|AAD51929.1|AF144306_2|; |5764372|gb|AAD51268.1|AF153258_2|;

| M2 proteins | | |
|---|---|---|
| |5764366|gb|AAD51264.1|AF153256_2|; | |71655385|gb|AAZ38741.1|; | |71655380|gb|AAZ38739.1|; |
| |71655372|gb|AAZ38737.1|; | |71655357|gb|AAZ38735.1|; | |71655346|gb|AAZ38733.1|; |
| |71655342|gb|AAZ38731.1|; | |71655321|gb|AAZ38729.1|; | |73852958|ref|YP_308670.1|; |
| |73912687|ref|YP_308853.1|; | | |5732421|gb|AAD49092.1|AF156470_1|; |
| |5732418|gb|AAD49090.1|AF156469_1|; | | |5732415|gb|AAD49088.1|AF156468_1|; |
| |28194355|gb|AAO33518.1|AF474058_2|; | | |28194352|gb|AAO33516.1|AF474057_2|; |
| |28194349|gb|AAO33514.1|AF474056_2|; | | |28194346|gb|AAO33512.1|AF474055_2|; |
| |28194343|gb|AAO33510.1|AF474054_2|; | | |28194340|gb|AAO33508.1|AF474053_2|; |
| |28194337|gb|AAO33506.1|AF474052_2|; | | |28194334|gb|AAO33504.1|AF474051_2|; |
| |28194331|gb|AAO33502.1|AF474050_2|; | | |28194328|gb|AAO33500.1|AF474049_2|; |
| |5732406|gb|AAD49082.1|AF156465_1|; | | |5732424|gb|AAD49094.1|AF156471_1|; |
| |5732412|gb|AAD49086.1|AF156467_1|; | | |5732409|gb|AAD49084.1|AF156466_1|; |
| |5732403|gb|AAD49080.1|AF156464_1|; | | |5732400|gb|AAD49078.1|AF156463_1|; |
| |5732397|gb|AAD49076.1|AF156462_1|; | | |5732394|gb|AAD49074.1|AF156461_1|; |
| |5732391|gb|AAD49072.1|AF156460_1|; | | |5732388|gb|AAD49070.1|AF156459_1|; |
| |5732385|gb|AAD49068.1|AF156458_1|; | |324262|gb|AAA43253.1|; | |37933078|gb|AAO46714.1|; |
| |37933075|gb|AAO46712.1|; | |37933072|gb|AAO46710.1|; | |37933069|gb|AAO46708.1|; |
| |37933066|gb|AAO46706.1|; | |37933063|gb|AAO46704.1|; | |37933060|gb|AAO46702.1|; |
| |37933057|gb|AAO46700.1|; | |37933054|gb|AAO46698.1|; | |37933051|gb|AAO46696.1|; |
| |37933048|gb|AAO46694.1|; | |37933045|gb|AAO46692.1|; | |37933042|gb|AAO46690.1|; |
| |37933039|gb|AAO46688.1|; | |37933036|gb|AAO46686.1|; | |37933033|gb|AAO46684.1|; |
| |37933030|gb|AAO46682.1|; | |37933027|gb|AAO46680.1|; | |37933024|gb|AAO46678.1|; |
| |37933021|gb|AAO46676.1|; | |37933018|gb|AAO46674.1|; | |37933015|gb|AAO46672.1|; |
| |37933012|gb|AAO46670.1|; | |37933009|gb|AAO46668.1|; | |37933006|gb|AAO46666.1|; |
| |37933003|gb|AAO46664.1|; | |37933000|gb|AAO46662.1|; | |37932997|gb|AAO46660.1|; |
| |37932994|gb|AAO46658.1|; | |37932991|gb|AAO46656.1|; | |37932988|gb|AAO46654.1|; |
| |37932985|gb|AAO46652.1|; | |37785164|gb|AAO46421.1|; | |37785161|gb|AAO46419.1|; |
| |37785158|gb|AAO46417.1|; | |37785155|gb|AAO46415.1|; | |37785152|gb|AAO46413.1|; |
| |37785146|gb|AAO46409.1|; | |37785143|gb|AAO46407.1|; | |37785140|gb|AAO46405.1|; |
| |37785137|gb|AAO46403.1|; | |37785134|gb|AAO46401.1|; | |37785131|gb|AAO46399.1|; |
| |37785128|gb|AAO46397.1|; | |37785125|gb|AAO46395.1|; | |37785122|gb|AAO46393.1|; |
| |37785119|gb|AAO46391.1|; | |37785116|gb|AAO46389.1|; | |37785113|gb|AAO46387.1|; |
| |37785110|gb|AAO46385.1|; | |37785107|gb|AAO46383.1|; | |37785104|gb|AAO46381.1|; |
| |37785101|gb|AAO46379.1|; | |37785098|gb|AAO46377.1|; | |37785095|gb|AAO46375.1|; |
| |37785092|gb|AAO46373.1|; | |37785089|gb|AAO46371.1|; | |37785086|gb|AAO46369.1|; |
| |37785083|gb|AAO46367.1|; | |37785080|gb|AAO46365.1|; | |37785077|gb|AAO46363.1|; |
| |37785074|gb|AAO46361.1|; | |37785071|gb|AAO46359.1|; | |37785068|gb|AAO46357.1|; |
| |37785065|gb|AAO46355.1|; | |37785062|gb|AAO46353.1|; | |37785059|gb|AAO46351.1|; |
| |37785056|gb|AAO46349.1|; | |37785052|gb|AAO46346.1|; | |37785050|gb|AAO46345.1|; |
| |37785047|gb|AAO46343.1|; | |13925108|gb|AAK49252.1|AF255374_2|; | |
| |13274621|gb|AAK18004.1|AF255370_2|; | |13274618|gb|AAK18002.1|AF255369_2|; | |
| |75125|pir.parallel.MMIV2|; | |324324|gb|AAA43295.1|; | |324382|gb|AAA43335.1|; |
| |324321|gb|AAA43293.11; |325067|gb|AAA43673.1|; |324394|gb|AAA43343.11; |324370|gb|AAA43315.1|; | | |
| |324333|gb|AAA43301.11; |324315|gb|AAA43289.1|; |324309|gb|AAA43285.11; |324298|gb|AAA43276.1|; | | |
| |483856|gb|AAC79578.1|; | |2833662|gb|AAC34266.1|; | |73665376|gb|AAZ79395.1|; |
| |30025988|gb|AAP04511.1|; | |37785149|gb|AAO46411.1|; | |47716780|gb|AAT37567.1|; |
| |7420157|pir.parallel.PN0087|; | |77204|pir||S04051|; | |13925128|gb|AAK49260.1|; |
| |13925121|gb|AAK49257.1|; | |13925114|gb|AAK49254.1|; | |13925104|gb|AAK49250.1|AF255373_2|; |
| |13925100|gb|AAK49248.1|AF255372_2|; | | |13925097|gb|AAK49246.1|AF255371_2|; |
| |13925093|gb|AAK49244.1|AF255368_2|; | | |13925089|gb|AAK49242.1|AF255367_2|; |
| |13925085|gb|AAK49240.1|AF255366_2|; | | |13925081|gb|AAK49238.1|AF255365_2|; |
| |13925077|gb|AAK49236.1|AF255364_2|; | | |13925073|gb|AAK49234.1|AF255363_2|; |
| |11065887|gb|AAG28377.1|; | | |3414657|gb|AAC31293.1|; |
| |3414645|gb|AAC31285.1|; | |3414642|gb|AAC31283.1|; | |3414639|gb|AAC31281.1|; |
| |3414633|gb|AAC31277.1|; | |94167|pir.parallel.S14617|; | |324400|gb|AAA43348.1|; |
| |50365715|gb|AAT76158.1|; |18140845|gb|AAL60446.1|AF398876_2|; | |20065773|gb|AAM09299.1|; | |
| |20065770|gb|AAM09297.1|; | |324405|gb|AAA43350.1|; | |324397|gb|AAA43346.1|; |
| |324391|gb|AAA43341.1|; |324388|gb|AAA43339.1|; |324385|gb|AAA43337.1|; |324379|gb|AAA43333.1|; | | |
| |324376|gb|AAA43331.1|; |324373|gb|AAA43317.1|; |324343|gb|AAA43306.1|; |324330|gb|AAA43299.1|; | | |
| |324327|gb|AAA43297.1|; |324318|gb|AAA43291.1|; |324312|gb|AAA43287.1|; |324306|gb|AAA43281.1|; | | |
| |324303|gb|AAA43279.1|; | |27596999|ref|NP_775535.1|; | |63054906|gb|AAY28989.1|; |
| |60474|emb|CAA30893.1|; | |60471|emb|CAA30891.1|; | |60468|emb|CAA30889.1|; |
| |60465|emb|CAA30887.1|; | |60462|emb|CAA30885.1|; | |60459|emb|CAA30883.1|; |
| |45124753|emb|CAF33015.1|; | |348621|pir.parallel.C45539|; | |112614|pir.parallel.PN0084|; |
| |94146|pir.parallel.JN0393|; | |75128|pir.parallel.MFIVPR|; | |75126|pir.parallel.MFIV62|; |
| |7444523|pir.parallel.T09280|; | |77201|pir.parallel.S04061|; | |77198|pir.parallel.S04057|; |
| |51094109|gb|AAS89186.2|; | |51859838|gb|AAU11203.1|; | |51859835|gb|AAU11201.1|; |
| |51859832|gb|AAU11199.1|; | |51859826|gb|AAU11195.1|; | |51859823|gb|AAU11193.1|; |
| |51859820|gb|AAU11191.1|; | |51859817|gb|AAU11189.1|; | |51859814|gb|AAU11187.1|; |
| |51859811|gb|AAU11185.1|; | |51859808|gb|AAU11183.1|; | |51859805|gb|AAU11181.1|; |
| |51859802|gb|AAU11179.1|; | |51859799|gb|AAU11177.1|; | |51859793|gb|AAU11173.1|; |
| |51859790|gb|AAU11171.1|; | |51859787|gb|AAU11169.1|; | |51859784|gb|AAU11167.1|; |
| |41207455|gb|AAR99626.1|; | |29539574|gb|AAO88262.1|AF342818_2|; | |
| |14587043|gb|AAK70448.1|AF386772_2|; | | |14587040|gb|AAK70446.1|AF386771_2|; |
| |14587037|gb|AAK70444.1|AF386770_2|; | | |14587034|gb|AAK70442.1|AF386769_2|; |
| |14587031|gb|AAK70440.1|AF386768_2|; | | |14587028|gb|AAK70438.1|AF386767_2|; |
| |14587025|gb|AAK70436.1|AF386766_2|; | | |14587022|gb|AAK70434.1|AF386765_2|; |

| M2 proteins | | |
|---|---|---|
| |27462133|gb|AAO15337.1|AF225529_2|; | |27462130|gb|AAO15335.1|AF225528_2|; | |
| |27462127|gb|AAO15333.1|AF225527_2|; | |27462124|gb|AAO15331.1|AF225526_2|; | |
| |21693176|gb|AAM75162.1|AF389121_2|; | |14009744|gb|AAK51749.1|; | |14009741|gb|AAK51747.1|; |
| |14009738|gb|AAK51745.1|; | |14009735|gb|AAK51743.1|; | |14009732|gb|AAK51741.1|; |
| |14009729|gb|AAK51739.1|; | |14009726|gb|AAK51737.1|; | |14009723|gb|AAK51735.1|; |
| |14009720|gb|AAK51733.1|; | |14009717|gb|AAK51731.1|; | |4097641|gb|AAD00150.1|; |
| |4097638|gb|AAD00148.1|; | |4097635|gb|AAD00146.1|; | |4097632|gb|AAD00144.1|; |
| |4097629|gb|AAD00142.1|; | |4097626|gb|AAD00140.1|; | |4097623|gb|AAD00138.1|; |
| |4097620|gb|AAD00136.1|; | |4097617|gb|AAD00134.1|; | |4097614|gb|AAD00132.1|; |
| |4097611|gb|AAD00130.1|; | |3929613|gb|AAC80168.1|; | |3929610|gb|AAC80166.1|; |
| |3929607|gb|AAC80164.1|; | |3929604|gb|AAC80162.1|; | |3929601|gb|AAC80160.1|; |
| |3929598|gb|AAC80158.1|; | |3929595|gb|AAC80156.1|; | |3722203|gb|AAC63486.1|; |
| |3722200|gb|AAC63484.1|; | |3722197|gb|AAC63482.1|; | |3722194|gb|AAC63480.1|; |
| |3414663|gb|AAC31297.1|; | |3414660|gb|AAC31295.1|; | |3414654|gb|AAC31291.1|; |
| |3414651|gb|AAC31289.1|; | |3414648|gb|AAC31287.1|; | |3414636|gb|AAC31279.1|; |
| |3414630|gb|AAC31275.1|; | |3414627|gb|AAC31273.1|; | |60819|emb|CAA41929.1|; |
| |395148|emb|CAA31779.1|; | |54039852|sp|P63231|VMT2_IAUDO|; | |138836|sp|P05780|VMT2_IAWIL|; |
| |235418|gb|AAB19772.1|; | |138828|sp|P03492|VMT2_IAFPR|; | |138829|sp|P05778|VMT2_IAFPW|; |
| |554653|gb|AAA43274.1|; | |324292|gb|AAA43273.1|; | |324289|gb|AAA43271.1|; |
| |324286|gb|AAA43269.1 |; | |324283|gb|AAA43267.1|; | |324280|gb|AAA43265.1|; | |324277|gb|AAA43263.1|; | |
| |324274|gb|AAA43261.1|; | |324271|gb|AAA43259.1|; | |324268|gb|AAA43257.1|; |
| |54036546|sp|O70632|VMT2_IAHO3|; | |1912411|gb|AAB50991.1|; | |1912408|gb|AAB50989.1|; |
| |1912405|gb|AAB50987.1|; | |1912402|gb|AAB50985.1|; | |1912399|gb|AAB50983.1|; |
| |407934|gb|AAB39916.1|; | |406040|gb|AAA67336.1|; | |325083|gb|AAA43683.1|; |
| |324888|gb|AAA43577.1|; | |324363|gb|AAA43312.1|; | |324265|gb|AAA43255.1|; | |323977|gb|AAA43091.1|; | |
| |138833|sp|P06821|VMT2_IAPUE|; | | |138825|sp|P21430|VMT2_IAANN|; |
| |54039853|sp|P63232|VMT2_IAPOC|; | | |549380|sp|P35938|VMT2_IAUSS|; |
| |549379|sp|P36348|VMT2_IACKB|; | |138837|sp|P05779|VMT2_IAZI1|; | |138834|sp|P10920|VMT2_IASIN|; |
| |138832|sp|P08382|VMT2_IAMAN|; | | |138827|sp|P10921|VMT2_IAFOW|; |
| |138826|sp|P03491|VMT2_IABAN|; | | |54039859|sp|P67867|VMT2_IALE3|; |
| |54039858|sp|P67866|VMT2_IALE2|; | | |138830|sp|P26129|VMT2_IALE1|; |
| |13182926|gb|AAK14988.1|AF231361_1|; | |13182920|gb|AAK14984.1|AF231359_1|; | |
| |8307814|gb|AAF74337.1|AF084284_2|; | |8307811|gb|AAF74335.1|AF084283_2|; | |
| |8307808|gb|AAF74333.1|AF084282_2|; | |4584940|gb|AAD25212.1|AF073200_2|; | |
| |9857034|emb|CAC04082.1|; | |9857037|emb|CAC04084.1|; | |54299847|gb|AAV32647.1|; |
| |54299833|gb|AAV32639.1|; | |52078189|gb|AAU25870.1|; | |52078169|gb|AAU25859.1|; |
| |52078151|gb|AAU25849.1|; | |56583270|ref|NP_040979.2|; | |58531127|dbj|BAD89318.1|; |
| |58531095|dbj|BAD89308.1|; | |50956634|gb|AAT90835.1|; | |38524569|dbj|BAD02364.1|; |
| |38524551|dbj|BAD02354.1|; | |4584955|gb|AAD25222.1|AF073205_2|; | |
| |4584952|gb|AAD25220.1|AF073204_2|; | |4584949|gb|AAD25218.1|AF073203_2|; | |
| |4584946|gb|AAD25216.1|AF073202_2|; | |4584943|gb|AAD25214.1|AF073201_2|; | |
| |4584937|gb|AAD25210.1|AF073199_2|; | |4584934|gb|AAD25208.1|AF073198_2|; | |
| |4584931|gb|AAD25206.1|AF073197_2|; | |4584928|gb|AAD25204.1|AF073196_2|; | |
| |4584925|gb|AAD25202.1|AF073195_2|; | |4584922|gb|AAD25200.1|AF073194_2|; | |
| |4584919|gb|AAD25198.1|AF073193_2|; | |4584916|gb|AAD25196.1|AF073192_2|; | |
| |4584913|gb|AAD25194.1|AF073191_2|; | |4584910|gb|AAD25192.1|AF073190_2|; | |
| |4584907|gb|AAD25190.1|AF073189_2|; | |4584904|gb|AAD25188.1|AF073188_2|; | |
| |4584901|gb|AAD25186.1|AF073187_2|; | |4584898|gb|AAD25184.1|AF073186_2|; | |
| |4584895|gb|AAD25182.1|AF073185_2|; | |4584892|gb|AAD25180.1|AF073184_2|; | |
| |4584889|gb|AAD25178.1|AF073183_2|; | |4584886|gb|AAD25176.1|AF073182_2|; | |
| |4584883|gb|AAD25174.1|AF073181_2|; | |4584880|gb|AAD25172.1|AF073180_2|; | |
| |77917339|gb|ABB05218.1|; | |77917320|gb|ABB05207.1|; | |77917301|gb|ABB05196.1|; |
| |77869491|gb|ABB05185.1|; | |77863494|gb|ABB05007.1|; | |77863475|gb|ABB04996.1|; |
| |77863456|gb|ABB04985.1|; | |77863437|gb|ABB04974.1|; | |77863418|gb|ABB04963.1|; |
| |77863399|gb|ABB04952.1|; | |77863380|gb|ABB04941.1|; | |77863361|gb|ABB04930.1|; |
| |77863342|gb|ABB04919.1|; | |77863323|gb|ABB04908.1|; | |77861870|gb|ABB04373.1|; |
| |77861851|gb|ABB04362.1|; | |77861832|gb|ABB04351.1|; | |77861813|gb|ABB04340.1|; |
| |77861794|gb|ABB04329.1|; | |77861775|gb|ABB04318.1|; | |77861756|gb|ABB04307.1|; |
| |77861737|gb|ABB04296.1|; | |77861718|gb|ABB04285.1|; | |77747463|gb|ABB03147.1|; |
| |77747444|gb|ABB03136.1|; | |77747425|gb|ABB03125.1|; | |77747405|gb|ABB03114.1|; |
| |77747386|gb|ABB03103.1|; | |77747367|gb|ABB03092.1|; | |77747348|gb|ABB03081.1|; |
| |77747329|gb|ABB03070.1|; | |77747308|gb|ABB03059.1|; | |77747289|gb|ABB03048.1|; |
| |77747270|gb|ABB03037.1|; | |77747251|gb|ABB03026.1|; | |77747232|gb|ABB03015.1|; |
| |77747213|gb|ABB03004.1|; | |77747194|gb|ABB02993.1|; | |77747175|gb|ABB02982.1|; |
| |77747154|gb|ABB02971.1|; | |77747135|gb|ABB02960.1|; | |77747116|gb|ABB02949.1|; |
| |77747097|gb|ABB02938.1|; | |77747076|gb|ABB02926.1|; | |77747057|gb|ABB02915.1|; |
| |77747038|gb|ABB02904.1|; | |77746992|gb|ABB02893.1|; | |77746973|gb|ABB02882.1|; |
| |77746954|gb|ABB02871.1|; | |77746935|gb|ABB02860.1|; | |77746916|gb|ABB02849.1|; |
| |77746895|gb|ABB02838.1|; | |77746876|gb|ABB02827.1|; | |77746857|gb|ABB02816.1|; |
| |77746838|gb|ABB02805.1|; | |77746819|gb|ABB02794.1|; | |77746800|gb|ABB02783.1|; |
| |77543686|gb|ABA87255.1|; | |77543666|gb|ABA87244.1|; | |77543646|gb|ABA87233.1|; |
| |77543364|gb|ABA87093.1|; | |77543345|gb|ABA87082.1|; | |77543301|gb|ABA87059.1|; |
| |77543245|gb|ABA87047.1|; | |76464352|gb|ABA43338.1|; | |76453796|gb|ABA43202.1|; |
| |76446823|gb|ABA43191.1|; | |76446802|gb|ABA43180.1|; | |76446429|gb|ABA43169.1|; |
| |76446387|gb|ABA42980.1|; | |76446315|gb|ABA42941.1|; | |76446296|gb|ABA42930.1|; |
| |76443530|gb|ABA42577.1|; | |76443511|gb|ABA42566.1|; | |76443492|gb|ABA42555.1|; |
| |76443473|gb|ABA42544.1|; | |76443454|gb|ABA42533.1|; | |76443435|gb|ABA42522.1|; |

| M2 proteins | | |
|---|---|---|
| \|76443416\|gb\|ABA42511.1\|; | \|76443397\|gb\|ABA42500.1\|; | \|76443378\|gb\|ABA42489.1\|; |
| \|76443359\|gb\|ABA42478.1\|; | \|76443340\|gb\|ABA42467.1\|; | \|76443321\|gb\|ABA42456.1\|; |
| \|76443272\|gb\|ABA42445.1\|; | \|76443253\|gb\|ABA42414.1\|; | \|76443234\|gb\|ABA42403.1\|; |
| \|76443215\|gb\|ABA42392.1\|; | \|76443196\|gb\|ABA42381.1\|; | \|76443177\|gb\|ABA42370.1\|; |
| \|76440842\|gb\|ABA42359.1\|; | \|76426670\|gb\|ABA42348.1\|; | \|76418550\|gb\|ABA42337.1\|; |
| \|76411034\|gb\|ABA42326.1\|; | \|76410402\|gb\|ABA42315.1\|; | \|76403103\|gb\|ABA42304.1\|; |
| \|76381505\|gb\|ABA42293.1\|; | \|76374058\|gb\|ABA42282.1\|; | \|76366072\|gb\|ABA42271.1\|; |
| \|76366053\|gb\|ABA42260.1\|; | \|76366034\|gb\|ABA42249.1\|; | \|76366015\|gb\|ABA42238.1\|; |
| \|75750348\|gb\|ABA26801.1\|; | \|75750329\|gb\|ABA26790.1\|; | \|75750310\|gb\|ABA26779.1\|; |
| \|75750291\|gb\|ABA26768.1\|; | \|75750272\|gb\|ABA26757.1\|; | \|75750253\|gb\|ABA26746.1\|; |
| \|75750234\|gb\|ABA26735.1\|; | \|75750215\|gb\|ABA26724.1\|; | \|75750196\|gb\|ABA26713.1\|; |
| \|75750177\|gb\|ABA26702.1\|; | \|75180515\|gb\|ABA12742.1\|; | \|75172967\|gb\|ABA12731.1\|; |
| \|75171346\|gb\|ABA12719.1\|; | \|75171063\|gb\|ABA12709.1\|; | \|75168356\|gb\|ABA12698.1\|; |
| \|74477289\|gb\|ABA08521.1\|; | \|74477270\|gb\|ABA08510.1\|; | \|74477249\|gb\|ABA08499.1\|; |
| \|74477230\|gb\|ABA08488.1\|; | \|74477211\|gb\|ABA08477.1\|; | \|74477192\|gb\|ABA08466.1\|; |
| \|74422756\|gb\|ABA06544.1\|; | \|74422587\|gb\|ABA06512.1\|; | \|73919153\|ref\|YP_308840.1\|; |
| \|32141422\|ref\|NP_859035.1\|; | \|73765596\|gb\|AAZ85128.1\|; | \|73763198\|gb\|AAZ83979.1\|; |
| \|73762505\|gb\|AAZ83690.1\|; | \|73762294\|gb\|AAZ83651.1\|; | \|73761788\|gb\|AAZ83384.1\|; |
| \|73761721\|gb\|AAZ83373.1\|; | \|73761599\|gb\|AAZ83325.1\|; | \|73761580\|gb\|AAZ83314.1\|; |
| \|73761561\|gb\|AAZ83301.1\|; | \|73761523\|gb\|AAZ83279.1\|; | \|73761500\|gb\|AAZ83268.1\|; |
| \|73761477\|gb\|AAZ83255.1\|; | \|73761458\|gb\|AAZ83244.1\|; | \|73666616\|gb\|AAZ80032.1\|; |
| \|73666597\|gb\|AAZ80020.1\|; | \|73666578\|gb\|AAZ80009.1\|; | \|73666559\|gb\|AAZ79998.1\|; |
| \|73666540\|gb\|AAZ79987.1\|; | \|73665975\|gb\|AAZ79976.1\|; | \|73665925\|gb\|AAZ79965.1\|; |
| \|73665877\|gb\|AAZ79947.1\|; | \|73665869\|gb\|AAZ79943.1\|; | \|73665831\|gb\|AAZ79631.1\|; |
| \|73665828\|gb\|AAZ79629.1\|; | \|73665807\|gb\|AAZ79617.1\|; | \|73665788\|gb\|AAZ79606.1\|; |
| \|73665769\|gb\|AAZ79595.1\|; | \|73665750\|gb\|AAZ79584.1\|; | \|73665731\|gb\|AAZ79573.1\|; |
| \|73665712\|gb\|AAZ79562.1\|; | \|73665693\|gb\|AAZ79551.1\|; | \|73665674\|gb\|AAZ79540.1\|; |
| \|73665655\|gb\|AAZ79529.1\|; | \|73665636\|gb\|AAZ79518.1\|; | \|73665613\|gb\|AAZ79507.1\|; |
| \|67644048\|gb\|AAY78941.1\|; | \|62198979\|gb\|AAX76735.1\|; | \|72602390\|gb\|AAZ74608.1\|; |
| \|72602371\|gb\|AAZ74597.1\|; | \|72602352\|gb\|AAZ74586.1\|; | \|72602239\|gb\|AAZ74575.1\|; |
| \|72598157\|gb\|AAZ74564.1\|; | \|72597909\|gb\|AAZ74553.1\|; | \|72582114\|gb\|AAZ74542.1\|; |
| \|72580905\|gb\|AAZ74531.1\|; | \|72578615\|gb\|AAZ74520.1\|; | \|72572289\|gb\|AAZ74509.1\|; |
| \|72572211\|gb\|AAZ74498.1\|; | \|72568983\|gb\|AAZ74487.1\|; | \|72565899\|gb\|AAZ74476.1\|; |
| \|72562518\|gb\|AAZ74465.1\|; | \|72556624\|gb\|AAZ74454.1\|; | \|72554371\|gb\|AAZ74443.1\|; |
| \|72552877\|gb\|AAZ74432.1\|; | \|72552073\|gb\|AAZ74421.1\|; | \|72549572\|gb\|AAZ74410.1\|; |
| \|72545852\|gb\|AAZ74399.1\|; | \|72545118\|gb\|AAZ74388.1\|; | \|72542982\|gb\|AAZ74376.1\|; |
| \|72539893\|gb\|AAZ74365.1\|; | \|72539854\|gb\|AAZ74354.1\|; | \|71000194\|dbj\|BAE07158.1\|; |
| \|71842590\|gb\|AAZ43407.1\|; | \|71842571\|gb\|AAZ43396.1\|; | \|71842552\|gb\|AAZ43385.1\|; |
| \|71842529\|gb\|AAZ43372.1\|; | \|71571148\|gb\|AAZ38652.1\|; | \|71568546\|gb\|AAZ38640.1\|; |
| \|71564883\|gb\|AAZ38629.1\|; | \|71564864\|gb\|AAZ38618.1\|; | \|71564845\|gb\|AAZ38607.1\|; |
| \|71564826\|gb\|AAZ38596.1\|; | \|71564807\|gb\|AAZ38585.1\|; | \|71564788\|gb\|AAZ38574.1\|; |
| \|71564769\|gb\|AAZ38563.1\|; | \|71564750\|gb\|AAZ38552.1\|; | \|71564731\|gb\|AAZ38541.1\|; |
| \|71564712\|gb\|AAZ38530.1\|; | \|71564693\|gb\|AAZ38519.1\|; | \|71564674\|gb\|AAZ38508.1\|; |
| \|71564655\|gb\|AAZ38497.1\|; | \|71564636\|gb\|AAZ38486.1\|; | \|71564617\|gb\|AAZ38475.1\|; |
| \|71564598\|gb\|AAZ38464.1\|; | \|70907643\|gb\|AAX56532.2\|; | \|62198871\|gb\|AAX76675.1\|; |
| \|68525443\|gb\|AAY98772.1\|; | \|68510080\|gb\|AAY98408.1\|; | \|68510061\|gb\|AAY98398.1\|; |
| \|68510042\|gb\|AAY98388.1\|; | \|68510011\|gb\|AAY98378.1\|; | \|68509990\|gb\|AAY98368.1\|; |
| \|68509958\|gb\|AAY98358.1\|; | \|68509896\|gb\|AAY98341.1\|; | \|68509733\|gb\|AAY98331.1\|; |
| \|68509377\|gb\|AAY98321.1\|; | \|68509335\|gb\|AAY98249.1\|; | \|68509315\|gb\|AAY98239.1\|; |
| \|68509296\|gb\|AAY98229.1\|; | \|68509276\|gb\|AAY98219.1\|; | \|68509252\|gb\|AAY98209.1\|; |
| \|68509227\|gb\|AAY98198.1\|; | \|68509210\|gb\|AAY98189.1\|; | \|68509189\|gb\|AAY98179.1\|; |
| \|68509171\|gb\|AAY98169.1\|; | \|68509153\|gb\|AAY98159.1\|; | \|68509135\|gb\|AAY98149.1\|; |
| \|68509116\|gb\|AAY98139.1\|; | \|68509098\|gb\|AAY98129.1\|; | \|68509080\|gb\|AAY98119.1\|; |
| \|68509062\|gb\|AAY98109.1\|; | \|68509044\|gb\|AAY98099.1\|; | \|68509012\|gb\|AAY98089.1\|; |
| \|68508931\|gb\|AAY98079.1\|; | \|68508894\|gb\|AAY98069.1\|; | \|68508817\|gb\|AAY98059.1\|; |
| \|68508601\|gb\|AAY98049.1\|; | \|68508516\|gb\|AAY98039.1\|; | \|62199033\|gb\|AAX76765.1\|; |
| \|62198817\|gb\|AAX76645.1\|; | \|61970921\|gb\|AAX57936.1\|; | \|61970723\|gb\|AAX57826.1\|; |
| \|61927527\|gb\|AAX56472.1\|; | \|59896447\|gb\|AAX11577.1\|; | \|67062584\|gb\|AAY64404.1\|; |
| \|67062043\|gb\|AAY64394.1\|; | \|67061887\|gb\|AAY64384.1\|; | \|67061091\|gb\|AAY64374.1\|; |
| \|67060409\|gb\|AAY64364.1\|; | \|67060168\|gb\|AAY64354.1\|; | \|67059536\|gb\|AAY64344.1\|; |
| \|67058968\|gb\|AAY64334.1\|; | \|67058905\|gb\|AAY64324.1\|; | \|67058350\|gb\|AAY64314.1\|; |
| \|67058332\|gb\|AAY64304.1\|; | \|67058314\|gb\|AAY64294.1\|; | \|67058296\|gb\|AAY64284.1\|; |
| \|67058278\|gb\|AAY64274.1\|; | \|67057699\|gb\|AAY64264.1\|; | \|67051337\|gb\|AAY64254.1\|; |
| \|67049850\|gb\|AAY64244.1\|; | \|67045889\|gb\|AAY64234.1\|; | \|67045468\|gb\|AAY64224.1\|; |
| \|67044511\|gb\|AAY64214.1\|; | \|67044335\|gb\|AAY64204.1\|; | \|67044259\|gb\|AAY64194.1\|; |
| \|67044159\|gb\|AAX57866.2\|; | \|66947417\|gb\|AAY59037.1\|; | \|66475121\|gb\|AAY47087.1\|; |
| \|66475103\|gb\|AAY47077.1\|; | \|66475059\|gb\|AAY47054.1\|; | \|66474991\|gb\|AAY47025.1\|; |
| \|66473598\|gb\|AAY46438.1\|; | \|66473580\|gb\|AAY46428.1\|; | \|66473562\|gb\|AAY46418.1\|; |
| \|66473492\|gb\|AAY46393.1\|; | \|66473470\|gb\|AAY46383.1\|; | \|66473450\|gb\|AAY46373.1\|; |
| \|66356018\|gb\|AAY45648.1\|; | \|66354527\|gb\|AAY44908.1\|; | \|66354509\|gb\|AAY44898.1\|; |
| \|66354011\|gb\|AAY44798.1\|; | \|66353991\|gb\|AAY44787.1\|; | \|66353973\|gb\|AAY44777.1\|; |
| \|66353873\|gb\|AAY44767.1\|; | \|66353855\|gb\|AAY44757.1\|; | \|66346632\|gb\|AAY44663.1\|; |
| \|66346002\|gb\|AAY44653.1\|; | \|66327420\|gb\|AAY44643.1\|; | \|66319002\|gb\|AAY44633.1\|; |
| \|66315205\|gb\|AAY44623.1\|; | \|66303355\|gb\|AAY44612.1\|; | \|3335426\|gb\|AAC32091.1\|; |
| \|3335408\|gb\|AAC32081.1\|; | \|63053666\|gb\|AAY28640.1\|; | \|63029988\|gb\|AAY27865.1\|; |
| \|63053684\|gb\|AAY28650.1\|; | \|63053648\|gb\|AAY28630.1\|; | \|63053630\|gb\|AAY28620.1\|; |
| \|63053612\|gb\|AAY28610.1\|; | \|63053529\|gb\|AAY28593.1\|; | \|63053497\|gb\|AAY28583.1\|; |

M2 proteins

|63053479|gb|AAY28573.1|; |63053460|gb|AAY28563.1|; |63047645|gb|AAY28553.1|;
|63038348|gb|AAY28543.1|; |63034458|gb|AAY28533.1|; |63034440|gb|AAY28523.1|;
|63034225|gb|AAY28504.1|; |63034196|gb|AAY28407.1|; |63034178|gb|AAY28397.1|;
|63034159|gb|AAY28387.1|; |63034141|gb|AAY28377.1|; |63034121|gb|AAY28366.1|;
|63034105|gb|AAY28357.1|; |63034087|gb|AAY28347.1|; |63034069|gb|AAY28337.1|;
|63034051|gb|AAY28327.1|; |63034033|gb|AAY28317.1|; |63034015|gb|AAY28307.1|;
|63033974|gb|AAY28297.1|; |63033956|gb|AAY28287.1|; |63033938|gb|AAY28277.1|;
|63033918|gb|AAY28267.1|; |63033415|gb|AAY28016.1|; |63033397|gb|AAY28006.1|;
|63033378|gb|AAY27996.1|; |63031461|gb|AAY27961.1|; |63029970|gb|AAY27855.1|;
|63029950|gb|AAY27845.1|; |62871286|gb|AAY18587.1|; |62871263|gb|AAY18566.1|;
|62870084|gb|AAY18198.1|; |62870066|gb|AAY18188.1|; |62870048|gb|AAY18178.1|;
|62870030|gb|AAY18168.1|; |62870012|gb|AAY18158.1|; |62869994|gb|AAY18148.1|;
|62869976|gb|AAY18138.1|; |62869958|gb|AAY18128.1|; |62869940|gb|AAY18118.1|;
|62869922|gb|AAY18108.1|; |62869904|gb|AAY18098.1|; |62869885|gb|AAY18088.1|;
|62198925|gb|AAX76705.1|; |62198799|gb|AAX76635.1|; |62198781|gb|AAX76625.1|;
|61620944|gb|AAX47527.1|; |62199015|gb|AAX76755.1|; |60683806|gb|AAX34063.1|;
|59940442|gb|AAX12763.1|; |438084|emb|CAA81472.1|; |438081|emb|CAA81470.1|;
|438078|emb|CAA81468.1|; |438075|emb|CAA81466.1|; |438071|emb|CAA81463.1|;
|22859489|emb|CAD30543.1|; |22859487|emb|CAD30541.1|; |22859484|emb|CAD30539.1|;
|22859481|emb|CAD30537.1|; |22859478|emb|CAD30535.1|; |20068130|emb|CAC87411.1|;
|20068121|emb|CAC87405.1|; |20068109|emb|CAC87397.1|; |20068106|emb|CAC87395.1|;
|20068100|emb|CAC87391.1|; |20068094|emb|CAC87387.1|; |14275728|emb|CAC40056.1|;
|14275701|emb|CAC40042.1|; |12038901|emb|CAC19701.1|; |9857031|emb|CAC04080.1|;
|62198997|gb|AAX76745.1|; |62198961|gb|AAX76725.1|; |62198943|gb|AAX76715.1|;
|62198907|gb|AAX76695.1|; |62198889|gb|AAX76685.1|; |62198853|gb|AAX76665.1|;
|62198835|gb|AAX76655.1|; |61970939|gb|AAX57946.1|; |61970885|gb|AAX57916.1|;
|61970867|gb|AAX57906.1|; |61970849|gb|AAX57896.1|; |61970831|gb|AAX57886.1|;
|61970813|gb|AAX57876.1|; |61970777|gb|AAX57856.1|; |61970759|gb|AAX57846.1|;
|61970741|gb|AAX57836.1|; |61970705|gb|AAX57816.1|; |61970687|gb|AAX57806.1|;
|61970669|gb|AAX57796.1|; |61970651|gb|AAX57786.1|; |61970633|gb|AAX57776.1|;
|61970615|gb|AAX57766.1|; |61970597|gb|AAX57756.1|; |61970579|gb|AAX57746.1|;
|61970561|gb|AAX57736.1|; |61970541|gb|AAX57725.1|; |61970525|gb|AAX57716.1|;
|61970507|gb|AAX57706.1|; |61970489|gb|AAX57696.1|; |61970471|gb|AAX57686.1|;
|61970453|gb|AAX57676.1|; |61970435|gb|AAX57666.1|; |61970417|gb|AAX57656.1|;
|61970399|gb|AAX57646.1|; |61928203|gb|AAX56602.1|; |61928146|gb|AAX56592.1|;
|61928095|gb|AAX56582.1|; |61928049|gb|AAX56572.1|; |61927991|gb|AAX56562.1|;
|61927940|gb|AAX56552.1|; |61927892|gb|AAX56542.1|; |61927797|gb|AAX56522.1|;
|61927745|gb|AAX56512.1|; |61927696|gb|AAX56502.1|; |61927634|gb|AAX56492.1|;
|61927580|gb|AAX56482.1|; |61927472|gb|AAX56462.1|; |61927420|gb|AAX56452.1|;
|61927368|gb|AAX56442.1|; |61927320|gb|AAX56432.1|; |61927273|gb|AAX56422.1|;
|61927226|gb|AAX56412.1|; |61927171|gb|AAX56402.1|; |61927123|gb|AAX56392.1|;
|61927074|gb|AAX56382.1|; |61620995|gb|AAX47537.1|; |61620911|gb|AAX47517.1|;
|61104890|gb|AAX38239.1|; |60738751|gb|AAX35873.1|; |60738733|gb|AAX35863.1|;
|60738715|gb|AAX35853.1|; |60738697|gb|AAX35843.1|; |60738679|gb|AAX35833.1|;
|60738661|gb|AAX35823.1|; |59940534|gb|AAX12813.1|; |59940516|gb|AAX12803.1|;
|59940498|gb|AAX12793.1|; |59940480|gb|AAX12783.1|; |59940460|gb|AAX12773.1|;
|59940424|gb|AAX12753.1|; |59940406|gb|AAX12743.1|; |59940388|gb|AAX12733.1|;
|59896555|gb|AAX11637.1|; |59896537|gb|AAX11627.1|; |59896519|gb|AAX11617.1|;
|59896501|gb|AAX11607.1|; |59896483|gb|AAX11597.1|; |59896465|gb|AAX11587.1|;
|59896429|gb|AAX11567.1|; |59896411|gb|AAX11557.1|; |59896393|gb|AAX11547.1|;
|59896375|gb|AAX11537.1|; |59896357|gb|AAX11527.1|; |59896339|gb|AAX11517.1|;
|59896321|gb|AAX11507.1|; |59896303|gb|AAX11497.1|; |59896285|gb|AAX11487.1|;
|59896267|gb|AAX11477.1|; |59896249|gb|AAX11467.1|; |59896231|gb|AAX11457.1|;
|61970903|gb|AAX57926.1|; |55233224|gb|AAV48544.1|; |13383294|dbj|BAB39519.1|;
|13383291|dbj|BAB39517.1|; |13182923|gb|AAK14986.1|AF231360_1|;
|13182917|gb|AAK14982.1|AF231358_1|; |8452836|gb|AAF75114.1|AF115287_2|;
|8452833|gb|AAF75112.1|AF115286_2|; |414306|gb|AAA91324.1|; |414303|gb|AAA91322.1|;
|577472|gb|AAA56809.1|; |577469|gb|AAA56807.1|; |577466|gb|AAA56805.1|; |324356|gb|AAA19196.1|;
|324353|gb|AAA19194.1|; |324350|gb|AAA19192.1|; |55139145|gb|AAV41246.1|;
|55139143|gb|AAV41245.1|; |50234651|gb|AAT70534.1|; |54610026|gb|AAV35111.1|;
|14579589|gb|AAK69310.1|AF385297_1|; |14579585|gb|AAK69309.1|AF385295_1|;
|21632613|gb|AAL32486.1|; |226441|prf.parallel.1512373B|; |57916088|gb|AAW59411.1|;
|57916040|gb|AAW59401.1|; |57916001|gb|AAW59394.1|; |50234771|gb|AAT70614.1|;
|50234765|gb|AAT70610.1|; |50234762|gb|AAT70608.1|; |50234759|gb|AAT70606.1|;
|50234756|gb|AAT70604.1|; |50234753|gb|AAT70602.1|; |50234750|gb|AAT70600.1|;
|50234747|gb|AAT70598.1|; |50234744|gb|AAT70596.1|; |50234741|gb|AAT70594.1|;
|50234738|gb|AAT70592.1|; |50234735|gb|AAT70590.1|; |50234732|gb|AAT70588.1|;
|50234723|gb|AAT70582.1|; |50234720|gb|AAT70580.1|; |50234717|gb|AAT70578.1|;
|50234714|gb|AAT70576.1|; |50234711|gb|AAT70574.1|; |50234708|gb|AAT70572.1|;
|50234705|gb|AAT70570.1|; |50234702|gb|AAT70568.1|; |50234699|gb|AAT70566.1|;
|50234696|gb|AAT70564.1|; |50234687|gb|AAT70558.1|; |50234684|gb|AAT70556.1|;
|50234681|gb|AAT70554.1|; |50234678|gb|AAT70552.1|; |50234672|gb|AAT70548.1|;
|50234669|gb|AAT70546.1|; |50234666|gb|AAT70544.1|; |50234663|gb|AAT70542.1|;
|50234660|gb|AAT70540.1|; |50234657|gb|AAT70538.1|; |50234654|gb|AAT70536.1|;
|50234648|gb|AAT70532.1|; |50234645|gb|AAT70530.1|; |50234642|gb|AAT70528.1|;
|50234639|gb|AAT70526.1|; |50234636|gb|AAT70524.1|; |50234633|gb|AAT70522.1|;
|50234630|gb|AAT70520.1|; |50234627|gb|AAT70518.1|; |50234624|gb|AAT70516.1|;

M2 proteins

|50234621|gb|AAT70514.1|; |50234618|gb|AAT70512.1|; |50234615|gb|AAT70510.1|;
|50234612|gb|AAT70508.1|; |50234609|gb|AAT70506.1|; |50234606|gb|AAT70504.1|;
|50234603|gb|AAT70502.1|; |50234601|gb|AAT70501.1|; |34597771|gb|AAQ77443.1|;
|34597768|gb|AAQ77441.1|; |34597765|gb|AAQ77439.1|; |34597759|gb|AAQ77435.1|;
|34597756|gb|AAQ77433.1|; |21359673|gb|AAM49562.1|AF468843_2|; |21326690|gb|AAL75850.1|;
|15193277|gb|AAK91757.1|; |9994775|emb|CAC07367.1|; |9863928|gb|AAG01223.1|AF216735_2|;
|9863910|gb|AAG01213.1|AF216727_2|; |9863891|gb|AAG01203.1|AF216719_2|;
|7861793|gb|AAF70407.1|AF203788_2|; |468300|gb|AAA62337.1|; |468295|gb|AAA62334.1|;
|324336|gb|AAA43303.1|; |413855|gb|AAA43249.|1

NP proteins

|60476|emb|CAA32437.1|; |30466237|ref|NP_848686.1|; |30349245|gb|AAP22118.1|;
|30466222|ref|NP_848678.1|; |30349230|gb|AAP22110.1|; |4760951|gb|AAD29162.1|AF100364_1|;
|4760969|gb|AAD29171.1|AF100373_1|; |4760967|gb|AAD29170.1|AF100372_1|;
|4760965|gb|AAD29169.1|AF100371_1|; |4760963|gb|AAD29168.1|AF100370_1|;
|4760961|gb|AAD29167.1|AF100369_1|; |4760959|gb|AAD29166.1|AF100368_1|;
|4760957|gb|AAD29165.1|AF100367_1|; |4760955|gb|AAD29164.1|AF100366_1|;
|4760953|gb|AAD29163.1|AF100365_1|; |4760949|gb|AAD29161.1|AF100363_1|;
|4760947|gb|AAD29160.1|AF100362_1|; |4760945|gb|AAD29159.1|AF100361_1|;
|4760943|gb|AAD29158.1|AF100360_1|; |4760941|gb|AAD29157.1|AF100359_1|;
|4760939|gb|AAD29156.1|AF100358_1|; |4760937|gb|AAD29155.1|AF100357_1|;
|9622313|gb|AAF89732.1|AF170569_1|; |53829851|gb|AAU94830.1|; |53829849|gb|AAU94829.1|;
|53829847|gb|AAU94828.1|; |53829845|gb|AAU94827.1|; |53829843|gb|AAU94826.1|;
|53829841|gb|AAU94825.1|; |53829839|gb|AAU94824.1|; |53829837|gb|AAU94823.1|;
|53829835|gb|AAU94822.1|; |53829833|gb|AAU94821.1|; |53829831|gb|AAU94820.1|;
|53829829|gb|AAU94819.1|; |53829827|gb|AAU94818.1|; |20126592|gb|AAK95899.1|;
|12862815|dbj|OAB32618.1|; |12862813|dbj|BAB32617.1|; |12862811|dbj|BAB32616.1|;
|51340783|gb|AAU01000.1|; |50059414|gb|AAT69437.1|; |50059395|gb|AAT69426.1|;
|50059433|gb|AAT69448.1|; |39119|sp|P04665|VNUC_INBLE|; |6647904|sp|O36433|VNUC_INBP9|;
|139120|sp|P04666|VNUC_INBSI|; |139118|sp|P13885|VNUC_INBAD|;
|139117|sp|P13884|VNUC_INBAC|; |139116|sp|P11102|VNUC_INBAA|; |325245|gb|AAA43750.1|;
|75750295|gb|ABA26770.1|; |75750276|gb|ABA26759.1|; |75750257|gb|ABA26748.1|;
|75750238|gb|ABA26737.1|; |75750219|gb|ABA26726.1|; |75750200|gb|ABA26715.1|;
|75750181|gb|ABA26704.1|; |72623471|gb|AAZ74621.1|; |75218754|gb|ABA18171.1|;
|75217117|gb|ABA18160.1|; |75216184|gb|ABA18149.1|; |75215962|gb|ABA18138.1|;
|75215227|gb|ABA18127.1|; |75214330|gb|ABA18116.1|; |75213014|gb|ABA18041.1|;
|75206503|gb|ABA18030.1|; |75200474|gb|ABA16396.1|; |75181199|gb|ABA12788.1|;
|75181110|gb|ABA12777.1|; |75180930|gb|ABA12766.1|; |75180833|gb|ABA12755.1|;
|75180535|gb|ABA12744.1|; |75172977|gb|ABA12733.1|; |75171378|gb|ABA12722.1|;
|75171140|gb|ABA12711.1|; |75168380|gb|ABA12700.1|; |74477293|gb|ABA08523.1|;
|74477274|gb|ABA08512.1|; |74477253|gb|ABA08501.1|; |74477234|gb|ABA08490.1|;
|74477215|gb|ABA08479.1|; |74477196|gb|ABA08468.1|; |74422760|gb|ABA06546.1|;
|74422592|gb|ABA06514.1|; |73919147|ref|YP_308843.1|; |73765600|gb|AAZ85130.1|;
|73763202|gb|AAZ83981.1|; |73762509|gb|AAZ83692.1|; |73762316|gb|AAZ83653.1|;
|73761792|gb|AAZ83386.1|; |73761727|gb|AAZ83375.1|; |73761603|gb|AAZ83327.1|;
|73761584|gb|AAZ83316.1|; |73761565|gb|AAZ83303.1|; |73761546|gb|AAZ83292.1|;
|73761527|gb|AAZ83281.1|; |73761504|gb|AAZ83270.1|; |73761481|gb|AAZ83257.1|;
|73761462|gb|AAZ83246.1|; |73666620|gb|AAZ80034.1|; |73666601|gb|AAZ80022.1|;
|73666582|gb|AAZ80011.1|; |73666563|gb|AAZ80000.1|; |73666544|gb|AAZ79989.1|;
|73665979|gb|AAZ79978.1|; |73665929|gb|AAZ79967.1|; |73665886|gb|AAZ79952.1|;
|73665879|gb|AAZ79948.1|; |73665839|gb|AAZ79635.1|; |73665837|gb|AAZ79634.1|;
|73665811|gb|AAZ79619.1|; |73665792|gb|AAZ79608.1|; |73665773|gb|AAZ79597.1|;
|73665754|gb|AAZ79586.1|; |73665735|gb|AAZ79575.1|; |73665716|gb|AAZ79564.1|;
|73665697|gb|AAZ79553.1|; |73665678|gb|AAZ79542.1|; |73665659|gb|AAZ79531.1|;
|73665640|gb|AAZ79520.1|; |73665617|gb|AAZ79509.1|; |73665569|gb|AAX76737.2|;
|67644052|gb|AAY78943.1|; |61612074|gb|AAX47285.1|; |61612071|gb|AAX47284.1|;
|72602394|gb|AAZ74610.1|; |72602375|gb|AAZ74599.1|; |72602356|gb|AAZ74588.1|;
|72602280|gb|AAZ74577.1|; |72598222|gb|AAZ74566.1|; |72597929|gb|AAZ74555.1|;
|72582136|gb|AAZ74544.1|; |72580950|gb|AAZ74533.1|; |72578666|gb|AAZ74522.1|;
|72572309|gb|AAZ74511.1|; |72572215|gb|AAZ74500.1|; |72569024|gb|AAZ74489.1|;
|72565916|gb|AAZ74478.1|; |72562585|gb|AAZ74467.1|; |72556658|gb|AAZ74456.1|;
|72554392|gb|AAZ74445.1|; |72552890|gb|AAZ74434.1|; |72552088|gb|AAZ74423.1|;
|72549649|gb|AAZ74412.1|; |72545874|gb|AAZ74401.1|; |72545212|gb|AAZ74390.1|;
|72543007|gb|AAZ74378.1|; |72539897|gb|AAZ74367.1|; |72539859|gb|AAZ74356.1|;
|71000188|dbj|BAE07156.1|; |71842594|gb|AAZ43409.1|; |71842575|gb|AAZ43398.1|;
|71842556|gb|AAZ43387.1|; |71842533|gb|AAZ43374.1|; |71571156|gb|AAZ38654.1|;
|71568550|gb|AAZ38642.1|; |71564887|gb|AAZ38631.1|; |71564868|gb|AAZ38620.1|;
|71564849|gb|AAZ38609.1|; |71564830|gb|AAZ38598.1|; |71564811|gb|AAZ38587.1|;
|71564792|gb|AAZ38576.1|; |71564773|gb|AAZ38565.1|; |71564754|gb|AAZ38554.1|;
|71564735|gb|AAZ38543.1|; |71564716|gb|AAZ38532.1|; |71564697|gb|AAZ38521.1|;
|71564678|gb|AAZ38510.1|; |71564659|gb|AAZ38499.1|; |71564640|gb|AAZ38488.1|;
|71564621|gb|AAZ38477.1|; |71564602|gb|AAZ38466.1|; |70955500|gb|AAZ16302.1|;
|70955498|gb|AAZ16301.1|; |70955496|gb|AAZ16300.1|; |70955494|gb|AAZ16299.1|;

-continued

| NP proteins | | |
|---|---|---|
| \|70955492\|gb\|AAZ16298.1\|; | \|70955490\|gb\|AAZ16297.1\|; | \|70955488\|gb\|AAZ16296.1\|; |
| \|70955486\|gb\|AAZ16295.1\|; | \|70955483\|gb\|AAZ16294.1\|; | \|70955481\|gb\|AAZ16293.1\|; |
| \|70955479\|gb\|AAZ16292.1\|; | \|70907647\|gb\|AAX56534.2\|; | \|62198875\|gb\|AAX76677.1\|; |
| \|68525447\|gb\|AAY98774.1\|; | \|68510084\|gb\|AAY98410.1\|; | \|68510066\|gb\|AAY98400.1\|; |
| \|68510046\|gb\|AAY98390.1\|; | \|68510015\|gb\|AAY98380.1\|; | \|68509994\|gb\|AAY98370.1\|; |
| \|68509965\|gb\|AAY98360.1\|; | \|68509900\|gb\|AAY98343.1\|; | \|68509874\|gb\|AAY98333.1\|; |
| \|68509381\|gb\|AAY98323.1\|; | \|68509342\|gb\|AAY98251.1\|; | \|68509319\|gb\|AAY98241.1\|; |
| \|68509300\|gb\|AAY98231.1\|; | \|68509280\|gb\|AAY98221.1\|; | \|68509256\|gb\|AAY98211.1\|; |
| \|68509233\|gb\|AAY98201.1\|; | \|68509214\|gb\|AAY98191.1\|; | \|68509193\|gb\|AAY98181.1\|; |
| \|68509175\|gb\|AAY98171.1\|; | \|68509157\|gb\|AAY98161.1\|; | \|68509139\|gb\|AAY98151.1\|; |
| \|68509120\|gb\|AAY98141.1\|; | \|68509102\|gb\|AAY98131.1\|; | \|68509084\|gb\|AAY98121.1\|; |
| \|68509066\|gb\|AAY98111.1\|; | \|68509048\|gb\|AAY98101.1\|; | \|68509018\|gb\|AAY98091.1\|; |
| \|68508938\|gb\|AAY98081.1\|; | \|68508901\|gb\|AAY98071.1\|; | \|68508822\|gb\|AAY98061.1\|; |
| \|68508607\|gb\|AAY98051.1\|; | \|68508523\|gb\|AAY98041.1\|; | \|62198821\|gb\|AAX76647.1\|; |
| \|61970925\|gb\|AAX57938.1\|; | \|61970727\|gb\|AAX57828.1\|; | \|59896451\|gb\|AAX11579.1\|; |
| \|67527208\|gb\|AAY68365.1\|; | \|8894685\|emb\|CAB95838.1\|; | \|8894683\|emb\|CAB95837.1\|; |
| \|67062593\|gb\|AAY64406.1\|; | \|67062065\|gb\|AAY64396.1\|; | \|67061897\|gb\|AAY64386.1\|; |
| \|67061102\|gb\|AAY64376.1\|; | \|67060418\|gb\|AAY64366.1\|; | \|67060182\|gb\|AAY64356.1\|; |
| \|67059548\|gb\|AAY64346.1\|; | \|67058984\|gb\|AAY64336.1\|; | \|67058924\|gb\|AAY64326.1\|; |
| \|67058354\|gb\|AAY64316.1\|; | \|67058336\|gb\|AAY64306.1\|; | \|67058318\|gb\|AAY64296.1\|; |
| \|67058300\|gb\|AAY64286.1\|; | \|67058282\|gb\|AAY64276.1\|; | \|67057743\|gb\|AAY64266.1\|; |
| \|67051372\|gb\|AAY64256.1\|; | \|67050025\|gb\|AAY64246.1\|; | \|67045893\|gb\|AAY64236.1\|; |
| \|67045474\|gb\|AAY64226.1\|; | \|67044521\|gb\|AAY64216.1\|; | \|67044350\|gb\|AAY64206.1\|; |
| \|67044263\|gb\|AAY64196.1\|; | \|67044163\|gb\|AAX57868.2\|; | \|66947421\|gb\|AAY59039.1\|; |
| \|9187997\|emb\|CAB95839.2\|; | \|54635080\|gb\|AAV36516.1\|; | \|54635078\|gb\|AAV36515.1\|; |
| \|54635076\|gb\|AAV36514.1\|; | \|54635074\|gb\|AAV36513.1\|; | \|66475125\|gb\|AAY47089.1\|; |
| \|66475107\|gb\|AAY47079.1\|; | \|66475063\|gb\|AAY47056.1\|; | \|66474995\|gb\|AAY47027.1\|; |
| \|66474977\|gb\|AAY47017.1\|; | \|66473602\|gb\|AAY46440.1\|; | \|66473584\|gb\|AAY46430.1\|; |
| \|66473566\|gb\|AAY46420.1\|; | \|66473496\|gb\|AAY46395.1\|; | \|66473474\|gb\|AAY46385.1\|; |
| \|66473454\|gb\|AAY46375.1\|; | \|66356022\|gb\|AAY45650.1\|; | \|66354531\|gb\|AAY44910.1\|; |
| \|66354513\|gb\|AAY44900.1\|; | \|66354413\|gb\|AAY44890.1\|; | \|66354015\|gb\|AAY44800.1\|; |
| \|66353995\|gb\|AAY44789.1\|; | \|66353977\|gb\|AAY44779.1\|; | \|66353877\|gb\|AAY44769.1\|; |
| \|66353859\|gb\|AAY44759.1\|; | \|66346636\|gb\|AAY44665.1\|; | \|66346024\|gb\|AAY44655.1\|; |
| \|66327442\|gb\|AAY44645.1\|; | \|66319022\|gb\|AAY44635.1\|; | \|66315226\|gb\|AAY44625.1\|; |
| \|66303368\|gb\|AAY44614.1\|; | \|63054909\|gb\|AAY28991.1\|; | \|63053670\|gb\|AAY28642.1\|; |
| \|63029992\|gb\|AAY27867.1\|; | \|63053688\|gb\|AAY28652.1\|; | \|63053652\|gb\|AAY28632.1\|; |
| \|63053634\|gb\|AAY28622.1\|; | \|63053616\|gb\|AAY28612.1\|; | \|63053533\|gb\|AAY28595.1\|; |
| \|63053501\|gb\|AAY28585.1\|; | \|63053483\|gb\|AAY28575.1\|; | \|63053464\|gb\|AAY28565.1\|; |
| \|63047668\|gb\|AAY28555.1\|; | \|63038371\|gb\|AAY28545.1\|; | \|63034462\|gb\|AAY28535.1\|; |
| \|63034444\|gb\|AAY28525.1\|; | \|63034229\|gb\|AAY28506.1\|; | \|63034200\|gb\|AAY28409.1\|; |
| \|63034182\|gb\|AAY28399.1\|; | \|63034163\|gb\|AAY28389.1\|; | \|63034145\|gb\|AAY28379.1\|; |
| \|63034127\|gb\|AAY28369.1\|; | \|63034109\|gb\|AAY28359.1\|; | \|63034091\|gb\|AAY28349.1\|; |
| \|63034073\|gb\|AAY28339.1\|; | \|63034055\|gb\|AAY28329.1\|; | \|63034037\|gb\|AAY28319.1\|; |
| \|63034019\|gb\|AAY28309.1\|; | \|63033978\|gb\|AAY28299.1\|; | \|63033960\|gb\|AAY28289.1\|; |
| \|63033942\|gb\|AAY28279.1\|; | \|63033922\|gb\|AAY28269.1\|; | \|63033419\|gb\|AAY28018.1\|; |
| \|63033401\|gb\|AAY28008.1\|; | \|63033382\|gb\|AAY27998.1\|; | \|63033337\|gb\|AAY27963.1\|; |
| \|63029974\|gb\|AAY27857.1\|; | \|63029954\|gb\|AAY27847.1\|; | \|62871486\|gb\|AAY18615.1\|; |
| \|62871292\|gb\|AAY18589.1\|; | \|62871267\|gb\|AAY18571.1\|; | \|62870088\|gb\|AAY18200.1\|; |
| \|62870070\|gb\|AAY18190.1\|; | \|62870052\|gb\|AAY18180.1\|; | \|62870034\|gb\|AAY18170.1\|; |
| \|62870016\|gb\|AAY18160.1\|; | \|62869998\|gb\|AAY18150.1\|; | \|62869980\|gb\|AAY18140.1\|; |
| \|62869962\|gb\|AAY18130.1\|; | \|62869944\|gb\|AAY18120.1\|; | \|62869926\|gb\|AAY18110.1\|; |
| \|62869908\|gb\|AAY18100.1\|; | \|62869889\|gb\|AAY18090.1\|; | \|62198929\|gb\|AAX76707.1\|; |
| \|62198785\|gb\|AAX76627.1\|; | \|61620951\|gb\|AAX47529.1\|; | \|60683810\|gb\|AAX34065.1\|; |
| \|59940446\|gb\|AAX12765.1\|; | \|56311406\|emb\|CA129280.1\|; | \|56291614\|emb\|CAE48277.1\|; |
| \|62199037\|gb\|AAX76767.1\|; | \|62199019\|gb\|AAX76757.1\|; | \|62199001\|gb\|AAX76747.1\|; |
| \|62198965\|gb\|AAX76727.1\|; | \|62198947\|gb\|AAX76717.1\|; | \|62198911\|gb\|AAX76697.1\|; |
| \|62198893\|gb\|AAX76687.1\|; | \|62198857\|gb\|AAX76667.1\|; | \|62198839\|gb\|AAX76657.1\|; |
| \|62198803\|gb\|AAX76637.1\|; | \|61970943\|gb\|AAX57948.1\|; | \|61970889\|gb\|AAX57918.1\|; |
| \|61970871\|gb\|AAX57908.1\|; | \|61970853\|gb\|AAX57898.1\|; | \|61970835\|gb\|AAX57888.1\|; |
| \|61970817\|gb\|AAX57878.1\|; | \|61970781\|gb\|AAX57858.1\|; | \|61970763\|gb\|AAX57848.1\|; |
| \|61970745\|gb\|AAX57838.1\|; | \|61970709\|gb\|AAX57818.1\|; | \|61970691\|gb\|AAX57808.1\|; |
| \|61970673\|gb\|AAX57798.1\|; | \|61970655\|gb\|AAX57788.1\|; | \|61970637\|gb\|AAX57778.1\|; |
| \|61970619\|gb\|AAX57768.1\|; | \|61970601\|gb\|AAX57758.1\|; | \|61970583\|gb\|AAX57748.1\|; |
| \|61970565\|gb\|AAX57738.1\|; | \|61970545\|gb\|AAX57727.1\|; | \|61970529\|gb\|AAX57718.1\|; |
| \|61970511\|gb\|AAX57708.1\|; | \|61970493\|gb\|AAX57698.1\|; | \|61970475\|gb\|AAX57688.1\|; |
| \|61970457\|gb\|AAX57678.1\|; | \|61970439\|gb\|AAX57668.1\|; | \|61970421\|gb\|AAX57658.1\|; |
| \|61970412\|gb\|AAX57653.1\|; | \|61928216\|gb\|AAX56604.1\|; | \|61928159\|gb\|AAX56594.1\|; |
| \|61928104\|gb\|AAX56584.1\|; | \|61928059\|gb\|AAX56574.1\|; | \|61928002\|gb\|AAX56564.1\|; |
| \|61927951\|gb\|AAX56554.1\|; | \|61927903\|gb\|AAX56544.1\|; | \|61927806\|gb\|AAX56524.1\|; |
| \|61927757\|gb\|AAX56514.1\|; | \|61927708\|gb\|AAX56504.1\|; | \|61927649\|gb\|AAX56494.1\|; |
| \|61927595\|gb\|AAX56484.1\|; | \|61927538\|gb\|AAX56474.1\|; | \|61927484\|gb\|AAX56464.1\|; |
| \|61927432\|gb\|AAX56454.1\|; | \|61927380\|gb\|AAX56444.1\|; | \|61927331\|gb\|AAX56434.1\|; |
| \|61927285\|gb\|AAX56424.1\|; | \|61927238\|gb\|AAX56414.1\|; | \|61927182\|gb\|AAX56404.1\|; |
| \|61927135\|gb\|AAX56394.1\|; | \|61927085\|gb\|AAX56384.1\|; | \|61621003\|gb\|AAX47539.1\|; |
| \|61620918\|gb\|AAX47519.1\|; | \|61104894\|gb\|AAX38241.1\|; | \|60738755\|gb\|AAX35875.1\|; |
| \|60738737\|gb\|AAX35865.1\|; | \|60738719\|gb\|AAX35855.1\|; | \|60738701\|gb\|AAX35845.1\|; |
| \|60738683\|gb\|AAX35835.1\|; | \|60738665\|gb\|AAX35825.1\|; | \|59940538\|gb\|AAX12815.1\|; |

| NP proteins | | |
|---|---|---|
| |59940520|gb|AAX12805.1|; | |59940502|gb|AAX12795.1|; | |59940484|gb|AAX12785.1|; |
| |59940464|gb|AAX12775.1|; | |59940428|gb|AAX12755.1|; | |59940410|gb|AAX12745.1|; |
| |59940392|gb|AAX12735.1|; | |59896559|gb|AAX11639.1|; | |59896541|gb|AAX11629.1|; |
| |59896523|gb|AAX11619.1|; | |59896505|gb|AAX11609.1|; | |59896487|gb|AAX11599.1|; |
| |59896469|gb|AAX11589.1|; | |59896433|gb|AAX11569.1|; | |59896415|gb|AAX11559.1|; |
| |59896397|gb|AAX11549.1|; | |59896379|gb|AAX11539.1|; | |59896361|gb|AAX11529.1|; |
| |59896343|gb|AAX11519.1|; | |59896325|gb|AAX11509.1|; | |59896307|gb|AAX11499.1|; |
| |59896289|gb|AAX11489.1|; | |59896271|gb|AAX11479.1|; | |59896253|gb|AAX11469.1|; |
| |59896235|gb|AAX11459.1|; | |61970907|gb|AAX57928.1|; | |56548910|gb|AAV97620.1|; |
| |56548908|gb|AAV97619.1|; | |56548906|gb|AAV97618.1|; | |56548904|gb|AAV97617.1|; |
| |56425053|gb|AAV91225.1|; | |56425051|gb|AAV91224.1|; | |56425049|gb|AAV91223.1|; |
| |56425047|gb|AAV91222.1|; | |58429781|gb|AAW78295.1|; | |16076707|gb|AAL14084.1|AF222814_1|; |
| |13785215|emb|CAC37326.1|; | |12038908|emb|CAC19705.1|; | |12038906|emb|CAC19704.11 |
| |12038892|emb|CAC19696.1|; | | |8163867|gb|AAF73888.1|AF222778_1|; |
| |8163865|gb|AAF73887.1|AF222777_1|; | | |8163863|gb|AAF73886.1|AF222776_1|; |
| |8163861|gb|AAF73885.1|AF222775_1|; | | |8163859|gb|AAF73884.1|AF222774_1|; |
| |8163857|gb|AAF73883.1|AF222773_1|; | | |8163855|gb|AAF73882.1|AF222772_1|; |
| |8163853|gb|AAF73881.1|AF222771_1|; | | |8163851|gb|AAF73880.1|AF222770_1|; |
| |8163849|gb|AAF73879.1|AF222769_1|; | | |8163847|gb|AAF73878.1|AF222768_1|; |
| |10442686|gb|AAG17432.1|AF285888_1|; | | |9887189|gb|AAG01789.1|AF251431_1|; |
| |9887172|gb|AAG01780.1|AF251423_1|; | | |9887155|gb|AAG01771.1|AF251415_1|; |
| |9887138|gb|AAG01762.1|AF25|407_1|; | | |9887107|gb|AAG01746.1|AF251392_1|; |
| |9954391|gb|AAG09040.1|; | | |9437966|gb|AAF87508.1|AF250480_1|; |
| |9437956|gb|AAF87503.1|AF250475_1|; | | |9437954|gb|AAF87502.1|AF250474_1|; |
| |9437952|gb|AAF87501.1|AF250473_1|; | | |9437950|gb|AAF87500.1|AF250472_1|; |
| |9437948|gb|AAF87499.1|AF250471_1|; | | |9437946|gb|AAF87498.1|AF250470_1|; |
| |8515430|gb|AAF75997.1|AF250127_1|; | | |5732295|gb|AAD49023.1|AF156413_1|; |
| |5732289|gb|AAD49020.1|AF156410_1|; | | |5732299|gb|AAD49025.1|AF156415_1|; |
| |6048942|gb|AAF02407.1|AF098627_1|; | | |6048938|gb|AAF02405.1|AF098625_1|; |
| |6048936|gb|AAF02404.1|AF098624_1|; | | |6048934|gb|AAF02403.1|AF098623_1|; |
| |6048932|gb|AAF02402.1|AF098622_1|; | | |6048930|gb|AAF02401.1|AF098621_1|; |
| |6048928|gb|AAF02400.1|AF098620_1|; | | |6048926|gb|AAF02399.1|AF098619_1|; |
| |6048924|gb|AAF02398.1|AF098618_1|; | | |6048922|gb|AAF02397.1|AF098617_1|; |
| |5732287|gb|AAD49019.1|AF156409_1|; | | |5732285|gb|AAD49018.1|AF156408_1|; |
| |5732283|gb|AAD49017.1|AF156407_1|; | | |5732281|gb|AAD49016.1|AF156406_1|; |
| |5732277|gb|AAD49014.1|AF156404_1|; | | |5732275|gb|AAD49013.1|AF156403_1|; |
| |5732273|gb|AAD49012.1|AF156402_1|; | |3722169|gb|AAC63467.1|; | |3722167|gb|AAC63466.1|; |
| |3722165|gb|AAC63465.1|; | |3722163|gb|AAC63464.1|; | |3722161|gb|AAC63463.1|; |
| |3722159|gb|AAC63462.1|; | |3721982|gb|AAC63428.1|; | |3721980|gb|AAC63427.1|; |
| |3721978|gb|AAC63426.1|; | |3721976|gb|AAC63425.1|; | |50083251|gb|AAT70220.1|; |
| |221296|dbj|BAA00035.1|; | |1835738|gb|AAC57416.1|; | |221294|dbj|BAA00034.1|; |
| |50261909|gb|AAT72507.1|; | |325104|gb|AAA73112.1|; | |325097|gb|AAA73111.1|; |;
| >gi|325095|gb|AAA73105.1|; | |325089|gb|AAA73110.1|; | |325087|gb|AAA73109.1|; |
| |324890|gb|AAA73104.1|; |324584|gb|AAA73108.1|; |324582|gb|AAA73107.1|; |324256|gb|AAA73106.1|; | | |
| |61197036|gb|AAX39501.1|; | |61197032|gb|AAX39499.1|; | |175093|pir.parallel.VHIV8H|; |
| |50083235|gb|AAT70212.1|; | |37813190|gb|AAR04371.1|; | |37813188|gb|AAR04370.1|; |
| |37813192|gb|AAR04372.1|; | |60478|emb|CAA33899.1|; | |324031|gb|AAB59744.1|; |
| |16589037|gb|AAL26994.1|AF397199_1|; | | |16589034|gb|AAL26993.1|AF397198_1|; |
| |279784|pir.parallel.VHIVAK|; | |279783|pir.parallel.VHIVXL|; | |34597775|gb|AAQ77445.1|; |
| |34597773|gb|AAQ77444.1|; | |29539576|gb|AAO88263.1|AF342819_1|; | |61197034|gb|AAX39500.1|; |
| |90493384|dbj|BAA99400.1|; | |71084275|gb|AAZ23583.1|; | |71084269|gb|AAZ23580.1|; |
| |71084267|gb|AAZ23579.1|; | |55925904|gb|AAV68025.1|; | |58374190|gb|AAW72231.1|; |
| |58618448|gb|AAW80721.1|; | |58618446|gb|AAW80721.1|; | |27596994|ref|NP_775533.1|; |
| |58618444|gb|AAW80720.1|; | |21693171|gb|AAM75159.1|AF389119_1|; | |75108|pir.parallel.VHIVN8|; |
| |75107|pir.parallel.VHIVX1|; | |75104|pir.parallel.VHIVN1|; | |75103|pir.parallel.VHIVN2|; |
| |75102|pir.parallel.VHIVN3|; | |75101|pir.parallel.VHIVN6|; | |75100|pir.parallel.VHIVN9|; |
| |75094|pir.parallel.VHIVN7|; | |320344|pir.parallel.A60028|; | |320033|pir.parallel.VHIVM1|; |
| |320032|pir.parallel.VHIVC1|; | |75099|pir.parallel.VHIVX6|; | |75095|pir.parallel.VHIVX2|; |
| |66733741|gb|AAY52631.1|; | |66733739|gb|AAY52630.1|; | |66733737|gb|AAY52629.1|; |
| |66733735|gb|AAY52628.1|; | |66733733|gb|AAY52627.1|; | |66733731|gb|AAY52626.1|; |
| |66733729|gb|AAY52625.1|; | |66733727|gb|AAY52624.1|; | |66733725|gb|AAY52623.1|; |
| |66733723|gb|AAY52622.1|; | |66733721|gb|AAY52621.1|; | |66733719|gb|AAY52620.1|; |
| |66733717|gb|AAY52619.1|; | |66733715|gb|AAY52618.1|; | |66733713|gb|AAY52617.1|; |
| |66733711|gb|AAY52616.1|; | |66733709|gb|AAY52615.1|; | |66733707|gb|AAY52614.1|; |
| |66733705|gb|AAY52613.1|; | |66733703|gb|AAY52612.1|; | |66733701|gb|AAY52611.1|; |
| |66733699|gb|AAY52610.1|; | |66733697|gb|AAY52609.1|; | |66733695|gb|AAY52608.1|; |
| |66733693|gb|AAY52607.1|; | |66733691|gb|AAY52606.1|; | |66733689|gb|AAY52605.1|; |
| |66733687|gb|AAY52604.1|; | |73921307|ref|YP_308871.1|; | |37785430|gb|AAO46552.1|; |
| |37785428|gb|AAO46551.1|; | |37785426|gb|AAO46550.1|; | |37785424|gb|AAO46549.1|; |
| |37785422|gb|AAO46548.1|; | |37785420|gb|AAO46547.1|; | |37785418|gb|AAO46546.1|; |
| |37785416|gb|AAO46545.1|; | |37785414|gb|AAO46544.1|; | |37785412|gb|AAO46543.1|; |
| |37785410|gb|AAO46542.1|; | |37785408|gb|AAO46541.1|; | |37785406|gb|AAO46540.1|; |
| |37785404|gb|AAO46539.1|; | |37785402|gb|AAO46538.1|; | |37785400|gb|AAO46537.1|; |
| |37785398|gb|AAO46536.1|; | |37785396|gb|AAO46535.1|; | |37785394|gb|AAO46534.1|; |
| |37785392|gb|AAO46533.1|; | |37785390|gb|AAO46532.1|; | |37785388|gb|AAO46531.1|; |
| |37785386|gb|AAO46530.1|; | |37785384|gb|AAO46529.1|; | |37785382|gb|AAO46528.1|; |
| |37785380|gb|AAO46527.1|; | |37785378|gb|AAO46526.1|; | |37785376|gb|AAO46525.1|; |

NP proteins

|37785374|gb|AAO46524.1|; |37785372|gb|AAO46523.1|; |37785370|gb|AAO46522.1|;
|37785368|gb|AAO46521.1|; |37785244|gb|AAO46460.1|; |37785242|gb|AAO46459.1|;
|37785240|gb|AAO46458.1|; |37785238|gb|AAO46457.1|; |37785236|gb|AAO46456.1|;
|37785234|gb|AAO46455.1|; |37785232|gb|AAO46454.1|; |37785230|gb|AAO46453.1|;
|37785228|gb|AAO46452.1|; |37785226|gb|AAO46451.1|; |37785224|gb|AAO46450.1|;
|37785222|gb|AAO46449.1|; |37785220|gb|AAO46448.1|; |37785218|gb|AAO46447.1|;
|37785216|gb|AAO46446.1|; |37785214|gb|AAO46445.1|; |37785212|gb|AAO46444.1|;
|37785210|gb|AAO46443.1|; |37785208|gb|AAO46442.1|; |37785206|gb|AAO46441.1|;
|37785204|gb|AAO46440.1|; |37785202|gb|AAO46439.1|; |37785200|gb|AAO46438.1|;
|37785198|gb|AAO46437.1|; |37785196|gb|AAO46436.1|; |37785194|gb|AAO46435.1|;
|37785192|gb|AAO46434.1|; |37785190|gb|AAO46433.1|; |37785188|gb|AAO46432.1|;
|37785186|gb|AAO46431.1|; |37785184|gb|AAO46430.1|; |37785182|gb|AAO46429.1|;
|37785180|gb|AAO46428.1|; |37785178|gb|AAO46427.1|; |37785176|gb|AAO46426.1|;
|37785174|gb|AAO46425.1|; |37785172|gb|AAO46424.1|; |37785170|gb|AAO46423.1|;
|37785168|gb|AAO46422.1|; |13925172|gb|AAK49279.1|AF255753_1|;
|13274625|gb|AAK18006.1|AF255749_1|; |13274623|gb|AAK18005.1|AF255748_1|;
|31339496|gb|AAP49080.1|; |31339492|gb|AAP49078.1|; |66775627|gb|AAY56368.1|;
|42661500|emb|CAF31360.1|; |54126502|gb|AAV30830.1|; |50234808|gb|AAT70633.1|;
|18092172|gb|AAL59145.1|AF398420_1|; |18092170|gb|AAL59144.1|AF398419_1|;
|8307799|gb|AAF74328.1|AF084278_1|; |8307797|gb|AAF74327.1|AF084277_1|;
|8307795|gb|AAF74326.1|AF084276_1|; |2833664|gb|AAC34267.1|; |54126537|gb|AAV30838.1|;
|73852953|ref|YP_308667.1|; |32140159|ref|NP_859032.1|; |30025978|gb|AAP04508.1|;
|71013502|dbj|BAE07202.1|; |62466165|gb|AAX83408.1|; |62466157|gb|AAX83404.1|;
|54610028|gb|AAV35112.1|; |54299852|gb|AAV32650.1|; |54299838|gb|AAV32642.1|;
|52078184|gb|AAU25867.1|; |52078171|gb|AAU25860.1|; |52078148|gb|AAU25847.1|;
|47834203|gb|AAT38823.1|; |49357240|gb|AAT65380.1|; |49357234|gb|AAT65377.1|;
|49357232|gb|AAT65376.1|; |49357224|gb|AAT65372.1|; |49357216|gb|AAT65368.1|;
|49357212|gb|AAT65366.1|; |49357208|gb|AAT65364.1|; |49357196|gb|AAT65358.1|;
|49357186|gb|AAT65353.1|; |49357184|gb|AAT65352.1|; |13925169|gb|AAK49278.1|AF255752_1|;
|13925167|gb|AAK49277.1|AF255751_1|; |13925164|gb|AAK49276.1|AF255750_1|;
|13925161|gb|AAK49275.1|AF255747_1|; |13925159|gb|AAK49274.1|AF255746_1|;
|13925156|gb|AAK49273.1|AF255745_1|; |13925153|gb|AAK49272.1|AF255744_1|;
|13925151|gb|AAK49271.1|AF255743_1|; |13925148|gb|AAK49270.1|AF255742_1|;
|38154862|gb|AAR12367.1|; |38154860|gb|AAR12366.1|; |38154858|gb|AAR12365.1|;
|38154856|gb|AAR12364.1|; |38154854|gb|AAR12363.1|; |38154852|gb|AAR12362.1|;
|38154850|gb|AAR12361.1|; |38154848|gb|AAR12360.1|; |38154846|gb|AAR12359.1|;
|38154844|gb|AAR12358.1|; |38154842|gb|AAR12357.1|; |38154840|gb|AAR12356.1|;
|38154838|gb|AAR12355.1|; |38154836|gb|AAR12354.1|; |38154834|gb|AAR12353.1|;
|38154832|gb|AAR12352.1|; |38154830|gb|AAR12351.1|; |38154828|gb|AAR12350.1|;
|47156435|gb|AAT12105.1|; |47156433|gb|AAT12104.1|; |47156431|gb|AAT12103.1|;
|47156429|gb|AAT12102.1|; |47156427|gb|AAT12101.1|; |47156425|gb|AAT12100.1|;
|47156423|gb|AAT12099.1|; |47156421|gb|AAT12098.1|; |47156419|gb|AAT12097.1|;
|47156417|gb|AAT12096.1|; |47156415|gb|AAT12095.1|; |47156413|gb|AAT12094.1|;
|47156411|gb|AAT12093.1|; |47156409|gb|AAT12092.1|; |47156407|gb|AAT12091.1|;
|47156405|gb|AAT12090.1|; |47156403|gb|AAT12089.1|; |47156401|gb|AAT12088.1|;
|47156399|gb|AAT12087.1|; |47156397|gb|AAT12086.1|; |47156395|gb|AAT12085.1|;
|30522970|gb|AAO65613.1|; |28849563|gb|AAO52964.1|AF509121_1|;
|19422133|gb|AAL87893.1|AF455703_1|; |19422127|gb|AAL87890.1|AF455700_1|;
|19422125|gb|AAL87889.1|AF455699_1|; |290762|gb|AAA51501.1|;
|9802278|gb|AAF99666.1|AF258516_1|; |5732297|gb|AAD49024.1|AF156414_1|;
|5732293|gb|AAD49022.1|AF156412_1|; |5732291|gb|AAD49021.1|AF156411_1|;
|6048944|gb|AAF02408.1|AF098628_1|; |6048940|gb|AAF02406.1|AF098626_1|;
|5805283|gb|AAD51925.1|AF144303_1|; |59803332|gb|AAX07774.1|;
|57916081|gb|AAW59409.1|; |57916035|gb|AAW59399.1|; |57915988|gb|AAW59391.1|;
|47716775|gb|AAT37564.1|; |42661498|emb|CAF31359.1|; |60823|emb|CAA36505.1|;
|60821|emb|CAA36234.1|; |58531177|dbj|BAD89346.1|; |58531159|dbj|BAD89336.1|;
|58531141|dbj|BAD89326.1|; |58531123|dbj|BAD89316.1|; |58531091|dbj|BAD89306.1|;
|50956630|gb|AAT90833.1|; |50234860|gb|AAT70659.1|; |50234830|gb|AAT70644.1|;
|50234828|gb|AAT70643.1|; |50234826|gb|AAT70642.1|; |50234824|gb|AAT70641.1|;
|50234822|gb|AAT70640.11|; |50234820|gb|AAT70639.1|; |50234818|gb|AAT70638.1|;
|50234816|gb|AAT70637.1|; |50234814|gb|AAT70636.1|; |50234812|gb|AAT70635.1|;
|50234810|gb|AAT70634.1|; |50234806|gb|AAT70632.1|; |50234804|gb|AAT70631.1|;
|50234802|gb|AAT70630.1|; |50234800|gb|AAT70629.1|; |50234798|gb|AAT70628.1|;
|50234796|gb|AAT70627.1|; |50234794|gb|AAT70626.1|; |50234792|gb|AAT70625.1|;
|50234790|gb|AAT70624.1|; |50234778|gb|AAT70618.1|; |50234776|gb|AAT70617.1|;
|50234774|gb|AAT70616.1|; |42521292|gb|AAS18236.1|; |38524558|dbj|BAD02358.1|;
|38524540|dbj|BAD02348.1|; |6177890|dbj|BAA86069.1|; |6177888|dbj|BAA86068.1|;
|6177886|dbj|BAA86067.1|; |6177884|dbj|BAA86066.1|; |28194391|gb|AAO33540.1|AF474070_1|;
|28194387|gb|AAO33539.1|AF474069_1|; |24286070|gb|AAN46830.1|;
|14579581|gb|AAK69308.1|AF385293_1|; |18140826|gb|AAL60436.1|AF398867_1|;
|18074925|emb|CAC84253.1|; |18074923|emb|CAC84252.1|; |18074921|emb|CAC84251.1|;
|18074919|emb|CAC84250.1|; |18074917|emb|CAC84249.1|; |18074915|emb|CAC84248.1|;
|18074913|emb|CAC84247.1|; |18074911|emb|CAC84246.1|; |18074909|emb|CAC84245.1|;
|8452830|gb|AAF75110.1|AF115285_1|; |8452828|gb|AAF75109.1|AF115284_1|;
|77917343|gb|ABB05220.1|; |77917324|gb|ABB05209.1|; |77917305|gb|ABB05198.1|;
|77869495|gb|ABB05187.1|; |77863498|gb|ABB05009.1|; |77863479|gb|ABB04998.1|;
|77863460|gb|ABB04987.1|; |77863441|gb|ABB04976.1|; |77863422|gb|ABB04965.1|;

| NP proteins | | |
|---|---|---|
| |77863403|gb|ABB04954.1|; | |77863384|gb|ABB04943.1|; | |77863365|gb|ABB04932.1|; |
| |77863346|gb|ABB04921.1|; | |77863327|gb|ABB04910.1|; | |77861874|gb|ABB04375.1|; |
| |77861855|gb|ABB04364.1|; | |77861836|gb|ABB04353.1|; | |77861817|gb|ABB04342.1|; |
| |77861798|gb|ABB04331.1|; | |77861779|gb|ABB04320.1|; | |77861760|gb|ABB04309.1|; |
| |77861741|gb|ABB04298.1|; | |77861722|gb|ABB04287.1|; | |77747467|gb|ABB03149.1|; |
| |77747448|gb|ABB03138.1|; | |77747429|gb|ABB03127.1|; | |77747409|gb|ABB03116.1|; |
| |77747390|gb|ABB03105.1|; | |77747371|gb|ABB03094.1|; | |77747352|gb|ABB03083.1|; |
| |77747333|gb|ABB03072.1|; | |77747312|gb|ABB03061.1|; | |77747293|gb|ABB03050.1|; |
| |77747274|gb|ABB03039.1|; | |77747255|gb|ABB03028.1|; | |77747236|gb|ABB03017.1|; |
| |77747217|gb|ABB03006.1|; | |77747198|gb|ABB02995.1|; | |77747179|gb|ABB02984.1|; |
| |77747158|gb|ABB02973.1|; | |77747139|gb|ABB02962.1|; | |77747120|gb|ABB02951.1|; |
| |77747101|gb|ABB02940.1|; | |77747080|gb|ABB02928.1|; | |77747061|gb|ABB02917.1|; |
| |77747042|gb|ABB02906.1|; | |77746996|gb|ABB02895.1|; | |77746977|gb|ABB02884.1|; |
| |77746958|gb|ABB02873.1|; | |77746939|gb|ABB02862.1|; | |77746920|gb|ABB02851.1|; |
| |77746899|gb|ABB02840.1|; | |77746880|gb|ABB02829.1|; | |77746861|gb|ABB02818.1|; |
| |77746842|gb|ABB02807.1|; | |77746823|gb|ABB02796.1|; | |77746804|gb|ABB02785.1|; |
| |77543690|gb|ABA87257.1|; | |77543670|gb|ABA87246.1|; | |77543650|gb|ABA87235.1|; |
| |77543368|gb|ABA87095.1|; | |77543349|gb|ABA87084.1|; | |77543305|gb|ABA87061.1|; |
| |77543249|gb|ABA87049.1|; | |76464403|gb|ABA43340.1|; | |76454181|gb|ABA43204.1|; |
| |76446827|gb|ABA43193.1|; | |76446806|gb|ABA43182.1|; | |76446435|gb|ABA43171.1|; |
| |76446410|gb|ABA42993.1|; | |76446391|gb|ABA42982.1|; | |76446319|gb|ABA42943.1|; |
| |76446300|gb|ABA42932.1|; | |76443534|gb|ABA42579.1|; | |76443515|gb|ABA42568.1|; |
| |76443496|gb|ABA42557.1|; | |76443477|gb|ABA42546.1|; | |76443458|gb|ABA42535.1|; |
| |76443439|gb|ABA42524.1|; | |76443420|gb|ABA42513.1|; | |76443401|gb|ABA42502.1|; |
| |76443382|gb|ABA42491.1|; | |76443363|gb|ABA42480.1|; | |76443344|gb|ABA42469.1|; |
| |76443325|gb|ABA42458.1|; | |76443276|gb|ABA42447.1|; | |76443257|gb|ABA42416.1|; |
| |76443238|gb|ABA42405.1|; | |76443219|gb|ABA42394.1|; | |76443200|gb|ABA42383.1|; |
| |76443181|gb|ABA42372.1|; | |76440953|gb|ABA42361.1|; | |76426705|gb|ABA42350.1|; |
| |76418682|gb|ABA42339.1|; | |76411109|gb|ABA42328.1|; | |76410460|gb|ABA42317.1|; |
| |76403227|gb|ABA42306.1|; | |76381543|gb|ABA42295.1|; | |76374097|gb|ABA42284.1|; |
| |76366076|gb|ABA42273.1|; | |76366057|gb|ABA42262.1|; | |76366038|gb|ABA42251.1|; |
| |76366019|gb|ABA42240.1|; | |75750352|gb|ABA26803.1|; | |75750333|gb|ABA26792.1|; |
| |75750314|gb|ABA26781.1|; | |58429773|gb|AAW78291.1|; | |58429761|gb|AAW78285.1|; |
| |58429759|gb|AAW78284.1|; | |50542643|gb|AAT78586.1|; | |50083045|gb|AAT70174.1|; |
| |50059188|gb|AAT69352.1|; | |55273941|gb|AAV48837.1|; | |55233233|gb|AAV48549.1|; |
| |53765727|gb|AAU93405.1|; | |51094113|gb|AAS89187.2|; | |51859870|gb|AAU11219.1|; |
| |51859868|gb|AAU11218.1|; | |51859866|gb|AAU11217.1|; | |51859864|gb|AAU11216.1|; |
| |51859862|gb|AAU11215.1|; | |51859860|gb|AAU11214.1|; | |51859858|gb|AAU11213.1|; |
| |51859856|gb|AAU11212.1|; | |51859854|gb|AAU11211.1|; | |51859852|gb|AAU11210.1|; |
| |51859850|gb|AAU11209.1|; | |51859848|gb|AAU11208.1|; | |51859846|gb|AAU11207.1|; |
| |51859844|gb|AAU11206.1|; | |51859842|gb|AAU11205.1|; | |51859840|gb|AAU11204.1|; |
| |50365720|gb|AAT76161.1|; | |47834948|gb|AAT39109.1|; | |47834946|gb|AAT39108.1|; |
| |47834944|gb|AAT39107.1|; | |47834934|gb|AAT39102.1|; | |47834932|gb|AAT39101.1|; |
| |33867359|gb|AAQ55062.1|; | |45124766|emb|CAF33022.1|; | |45124750|emb|CAF33013.1|; |
| |45124746|emb|CAF33011.1|; | | |33318065|gb|AAQ04906.1|AF508617_1|; |
| |33318063|gb|AAQ04905.1|AF508618_1|; | | |33318059|gb|AAQ04903.1|AF508614_1|; |
| |33318055|gb|AAQ04901.1|AF508612_1|; | | |33318053|gb|AAQ04900.1|AF508611|; |
| |33318049|gb|AAQ04898.1|AF508609_1|; | | |33318045|gb|AAQ04896.1|AF508607_1|; |
| |33318043|gb|AAQ04895.1|AF508608_1|; | | |33318041|gb|AAQ04894.1|AF508605_1|; |
| |41207477|gb|AAR99630.1|; | |40732903|emb|CAF04486.1|; | |14275699|emb|CAC40041.1|; |
| |21902318|gb|AAM78513.1|AF483604_1|; | |13383285|dbj|BAB39514.1|; | |13383283|dbj|BAB39513.1|; |
| |5531266|emb|CAB50887.1|; | | |30043924|gb|AAG01753.2|AF251399_1|; |
| |28849599|gb|AAO52982.1|AF509139_1|; | | |28849561|gb|AAO52963.1|AF509120_1|; |
| |28849559|gb|AAO52962.1|AF509119_1|; | | |28849557|gb|AAO52961.1|AF509118_1|; |
| |28849555|gb|AAO52960.1|AF509117_1|; | |28820286|gb|AAO46832.1|; | |28820284|gb|AAO46831.1|; |
| |28820282|gb|AAO46830.1|; | |28820280|gb|AAO46829.1|; | |28820278|gb|AAO46828.1|; |
| |28820276|gb|AAO46827.1|; | |28820047|gb|AAO46826.1|; | |28819610|gb|AAO46825.1|; |
| |28818981|gb|AAO46824.1|; | |18496110|emb|CAD20329.1|; | |27462153|gb|AAO15349.1|AF225537_1|; |
| |27462151|gb|AAO15348.1|AF225538_1|; | | |27462149|gb|AAO15347.1|AF225535_1|; |
| |27462147|gb|AAO15346.1|AF225534_1|; | |22859439|emb|CAD30201.1|; | |22859437|emb|CAD30200.1|; |
| |21359670|gb|AAM49560.1|AF468842_1|; | |20068061|emb|CAC85241.1|; | |20068055|emb|CAC85238.1|; |
| |20068051|emb|CAC85236.1|; | |20068049|emb|CAC85235.1|; | |20068037|emb|CAC85229.1|; |
| |19913216|emb|CAD20330.1|; | |19913210|emb|CAD20324.1|; | |19697806|gb|AAL31404.1|; |
| |19697804|gb|AA131403.1|; | |19697802|gb|AAL31402.1|; | |19697800|gb|AAL31401.1|; |
| |19697798|gb|AA131400.1|; | |19697796|gb|AAL31399.1|; | |19697794|gb|AA131398.1|; |
| |19422139|gb|AAL87896.1|AF455708_1|; | | |19422137|gb|AAL87895.1|AF455705_1|; |
| |19422135|gb|AAL87894.1|AF455704_1|; | | |19422131|gb|AAL87892.1|AF455702_1|; |
| |19422129|gb|AAL87891.1|AF455701_1|; | |16076709|gb|AAL14085.1|AF222815_1| | |

| PB1 proteins | | |
|---|---|---|
| |53829905|gb|AAU94857.1|; | |53829903|gb|AAU94856.1|; | |53829901|gb|AAU94855.1|; |
| |53829899|gb|AAU94854.1|; | |53829897|gb|AAU94853.1|; | |53829895|gb|AAU94852.1|; |
| |53829893|gb|AAU94851.1|; | |53829891|gb|AAU94850.1|; | |53829889|gb|AAU94849.1|; |

| PB1 proteins | | |
|---|---|---|
| |53829887|gb|AAU94848.1|; | |53829885|gb|AAU94847.1|; | |53829883|gb|AAU94846.1|; |
| |53829881|gb|AAU94845.1|; | |9622317|gb|AAF89734.1|AF170571_1|; | |558512|dbj|BAAO0002.1|; |
| |8486165|ref|NP_056657.1|; | | | |30466214|ref|NP_848674.1|; |
| |30349237|gb|AAP22114.1|; |30349222|gb|AAP22106.1|; | |325276|gb|AAA43767.1|; |67090|pir|P1IVBL|; | |
| |50059427|gb|AAT69445.1|; | |50059408|gb|AAT69434.1|; | |50059389|gb|AAT69423.1|; |
| |6318399|gb|AAF06876.1|AF102007_1|; | | |6318397|gb|AAF06875.1|AF102006_1|; |
| |6318395|gb|AAF06874.1|AF102005_1|; | | |6318393|gb|AAF06873.1|AF102004_1|; |
| |6318391|gb|AAF06872.1|AF102003_1|; | | |6318389|gb|AAF06871.1|AF102002_1|; |
| |6318387|gb|AAF06870.1|AF102001_1|; | | |6318385|gb|AAF06869.1|AF102000_1|; |
| |6318383|gb|AAF06868.1|AF101999_1|; | | |6318381|gb|AAF06867.1|AF101998_1|; |
| |6318379|gb|AAF06866.1|AF101997_1|; | | |6318377|gb|AAF06865.1|AF101996_1|; |
| |6318375|gb|AAF06864.1|AF101995_1|; | | |6318373|gb|AAF06863.1|AF101994_1|; |
| |6318371|gb|AAF06862.1|AF101993_1|; | | |6318369|gb|AAF06861.1|AF101992_1|; |
| |6318367|gb|AAF06860.1|AF101991_1|; | |68655094|emb|CAG96510.1|; | |20126603|gb|AAK95906.1|; |
| |51340771|gb|AAU00993.1|;    |133529|sp|P13872|RRP1_INBAD|; | | |133530|sp|P07832|RRP1_INBLE|; |
| |6647764|sp|O36430|RRP1_INBP9|; | |133528|sp|P13871|RRP1_INBAC|; | |8486151|ref|NP_056659.1|; |
| |6318433|gb|AAF06893.1|AF102024_1|; | | |6318431|gb|AAF06892.1|AF102023_1|; |
| |6318429|gb|AAF06891.1|AF102022_1|; | | |6318427|gb|AAF06890.1|AF102021_1|; |
| |6318425|gb|AAF06889.1|AF102020_1|; | | |6318423|gb|AAF06888.1|AF102019_1|; |
| |6318421|gb|AAF06887.1|AF102018_1|; | | |6318419|gb|AAF06886.1|AF102017_1|; |
| |6318417|gb|AAF06885.1|AF102016_1|; | | |6318415|gb|AAF06884.1|AF102015_1|; |
| |6318413|gb|AAF06883.1|AF102014_1|; | | |6318411|gb|AAF06882.1|AF102013_1|; |
| |6318409|gb|AAF06881.1|AF102012_1|; | | |6318407|gb|AAF06880.1|AF102011_1|; |
| |6318405|gb|AAF06879.1|AF102010_1|; | | |6318403|gb|AAF06878.1|AF102009_1|; |
| |6318401|gb|AAF06877.1|AF102008_1|; | |325278|gb|AAA43768.1|; | |2463656|gb|AAB72043.1|; |
| |18140834|gb|AAL60440.1|AF398871_1|; | | |18140822|gb|AAL60434.1|AF398865_1|; |
| |9437960|gb|AAF87505.1|AF250477_1|; | |324940|gb|AAA43631.1|; | |9049388|dbj|BAA99402.1|; |
| |71084265|gb|AAZ23578.1|; | |71084263|gb|AAZ23577.1|; | |71084261|gb|AAZ23576.1|; |
| |71084259|gb|AAZ23575.1|; | |71084257|gb|AAZ23574.1|; | |71084255|gb|AAZ23573.1|; |
| |71084253|gb|AAZ23572.1|; | |71084251|gb|AAZ23571.1|; | |73665386|gb|AAZ79400.1|; |
| |55925912|gb|AAV68029.1|; | |55925878|gb|AAV68012.1|; | |55925862|gb|AAV68004.1|; |
| |55925850|gb|AAV67998.1|;    |55925834|gb|AAV67990.1|; | |9802300|gb|AAF99677.1|AF258527_1|; | |
| |9802298|gb|AAF99676.1|AF258526_1|; | | |58374186|gb|AAW72229.1|; |
| |29539584|gb|AAO88267.1|AF342823_1|; | |37785460|gb|AAO46566.1|; | |37785458|gb|AAO46565.1|; |
| |37785456|gb|AAO46564.1|; | |37785454|gb|AAO46563.1|; | |37785452|gb|AAO46562.1|; |
| |37785450|gb|AAO46561.1|; | |37785448|gb|AAO46560.1|; | |37785446|gb|AAO46559.1|; |
| |37785444|gb|AAO46558.1|; | |37785442|gb|AAO46557.1|; | |37785440|gb|AAO46556.1|; |
| |37785438|gb|AAO46555.1|; | |37785436|gb|AAO46554.1|; | |37785434|gb|AAO46553.1|; |
| |37785044|gb|AAO46341.1|; | |37785042|gb|AAO46340.1|; | |37785040|gb|AAO46339.1|; |
| |37785038|gb|AAO46338.1|; | |37785036|gb|AAO46337.1|; | |37785034|gb|AAO46336.1|; |
| |37785032|gb|AAO46335.1|; | |37785030|gb|AAO46334.1|; | |37785028|gb|AAO46333.1|; |
| |37785026|gb|AAO46332.1|; | |37785024|gb|AAO46331.1|; | |37785022|gb|AAO46330.1|; |
| |37785020|gb|AAO46329.1|; | |37785018|gb|AAO46328.1|; | |37785016|gb|AAO46327.1|; |
| |37785014|gb|AAO46326.1|; | |37785012|gb|AAO46325.1|; | |37785010|gb|AAO46324.1|; |
| |3523119|gb|AAC34271.1|; | |54126556|gb|AAV30842.1|; | |52078177|gb|AAU25863.1|; |
| |52078159|gb|AAU25853.1|; | |52078141|gb|AAU25843.1|; | |47834373|gb|AAT38884.1|; |
| |54126513|gb|AAV30834.1|; | |31442137|emb|CAD92258.1|; | |30522957|gb|AAO65606.1|; |
| |5732325|gb|AAD49038.1|AF156428_1|; | | |5732323|gb|AAD49037.1|AF156427_1|; |
| |5732321|gb|AAD49036.1|AF156426_1|; | |73912683|ref|YP_308851.1|; | |18074831|emb|CAC84862.1|; |
| |18074829|emb|CAC84861.1|; | |18074827|emb|CAC84913.1|; | |18074825|emb|CAC84912.1|; |
| |18074823|emb|CAC84911.1|; | |18074821|emb|CAC84910.1|; | |18074819|emb|CAC84909.1|; |
| |18074817|emb|CAC84908.1|; | |77543697|gb|ABA87261.1|; | |77543677|gb|ABA87250.1|; |
| |77543657|gb|ABA87239.1|; | |77543377|gb|ABA87099.1|; | |77543356|gb|ABA87088.1|; |
| |77543312|gb|ABA87065.1|; | |77543256|gb|ABA87053.1|; | |76786707|gb|ABA55039.1|; |
| |76464433|gb|ABA43344.1|; | |76454573|gb|ABA43208.1|; | |76446442|gb|ABA43175.1|; |
| |76446417|gb|ABA42997.1|; | |76446398|gb|ABA42986.1|; | |76446326|gb|ABA42947.1|; |
| |76446307|gb|ABA42936.1|; | |76443541|gb|ABA42583.1|; | |76443522|gb|ABA42572.1|; |
| |76443503|gb|ABA42561.1|; | |76443484|gb|ABA42550.1|; | |76443465|gb|ABA42539.1|; |
| |76443446|gb|ABA42528.1|; | |76443427|gb|ABA42517.1|; | |76443408|gb|ABA42506.1|; |
| |76443389|gb|ABA42495.1|; | |76443370|gb|ABA42484.1|; | |76443351|gb|ABA42473.1|; |
| |76443332|gb|ABA42462.1|; | |76443283|gb|ABA42451.1|; | |76443264|gb|ABA42420.1|; |
| |76443245|gb|ABA42409.1|; | |76443226|gb|ABA42398.1|; | |76443207|gb|ABA42387.1|; |
| |76443188|gb|ABA42376.1|; | |76441125|gb|ABA42365.1|; | |76426762|gb|ABA42354.1|; |
| |76418836|gb|ABA42343.1|; | |76411281|gb|ABA42332.1|; | |76410537|gb|ABA42321.1|; |
| |76403298|gb|ABA42310.1|; | |76381630|gb|ABA42299.1|; | |76366083|gb|ABA42277.1|; |
| |76366064|gb|ABA42266.1|; | |76366045|gb|ABA42255.1|; | |76366026|gb|ABA42244.1|; |
| |75750359|gb|ABA26807.1|; | |75750340|gb|ABA26796.1|; | |75750321|gb|ABA26785.1|; |
| |75750302|gb|ABA26774.1|; | |75750283|gb|ABA26763.1|; | |75750264|gb|ABA26752.1|; |
| |75750245|gb|ABA26741.1|; | |75750226|gb|ABA26730.1|; | |75750207|gb|ABA26719.1|; |
| |75750188|gb|ABA26708.1|; | |72623485|gb|AAZ74625.1|; | |75218844|gb|ABA18175.1|; |
| |75217161|gb|ABA18164.1|; | |75216235|gb|ABA18153.1|; | |75215980|gb|ABA18142.1|; |
| |75215317|gb|ABA18131.1|; | |75214459|gb|ABA18120.1|; | |75213056|gb|ABA18045.1|; |
| |75206531|gb|ABA18034.1|; | |75200787|gb|ABA16472.1|; | |75181281|gb|ABA12792.1|; |
| |75181143|gb|ABA12784.1|; | |75180947|gb|ABA12770.1|; | |75180861|gb|ABA12759.1|; |
| |75180593|gb|ABA12748.1|; | |75173041|gb|ABA12737.1|; | |75171464|gb|ABA12726.1|; |
| |75171319|gb|ABA12716.1|; | |75168429|gb|ABA12704.1|; | |74477300|gb|ABA08527.1|; |
| |74477260|gb|ABA08505.1|; | |74477241|gb|ABA08494.1|; | |74477222|gb|ABA08483.1|; |

-continued

| PB1 proteins | | |
|---|---|---|
| \|74477203\|gb\|ABA08472.1\|; | \|74422768\|gb\|ABA06550.1\|; | \|74422600\|gb\|ABA06518.1\|; |
| \|73919149\|ref\|YP_308847.1\|; | \|32140170\|ref\|NP_859040.1\|; | \|73765607\|gb\|AAZ85134.1\|; |
| \|73763209\|gb\|AAZ83985.1\|; | \|73762516\|gb\|AAZ83696.1\|; | \|73762335\|gb\|AAZ83657.1\|; |
| \|73761799\|gb\|AAZ83390.1\|; | \|73761738\|gb\|AAZ83379.1\|; | \|73761610\|gb\|AAZ83331.1\|; |
| \|73761591\|gb\|AAZ83320.1\|; | \|73761572\|gb\|AAZ83307.1\|; | \|73761553\|gb\|AAZ83296.1\|; |
| \|73761534\|gb\|AAZ83285.1\|; | \|73761511\|gb\|AAZ83274.1\|; | \|73761488\|gb\|AAZ83261.1\|; |
| \|73761469\|gb\|AAZ83250.1\|; | \|73666629\|gb\|AAZ80038.1\|; | \|73666608\|gb\|AAZ80026.1\|; |
| \|73666589\|gb\|AAZ80015.1\|; | \|73666570\|gb\|AAZ80004.1\|; | \|73666551\|gb\|AAZ79993.1\|; |
| \|73665986\|gb\|AAZ79982.1\|; | \|73665938\|gb\|AAZ79971.1\|; | \|73665901\|gb\|AAZ79960.1\|; |
| \|73665893\|gb\|AAZ79956.1\|; | \|73665854\|gb\|AAZ79644.1\|; | \|73665851\|gb\|AAZ79642.1\|; |
| \|73665818\|gb\|AAZ79623.1\|; | \|73665799\|gb\|AAZ79612.1\|; | \|73665780\|gb\|AAZ79601.1\|; |
| \|73665761\|gb\|AAZ79590.1\|; | \|73665742\|gb\|AAZ79579.1\|; | \|73665723\|gb\|AAZ79568.1\|; |
| \|73665704\|gb\|AAZ79557.1\|; | \|73665685\|gb\|AAZ79546.1\|; | \|73665666\|gb\|AAZ79535.1\|; |
| \|73665647\|gb\|AAZ79524.1\|; | \|73665624\|gb\|AAZ79513.1\|; | \|67644059\|gb\|AAY78947.1\|; |
| \|62198990\|gb\|AAX76741.1\|; | \|72602401\|gb\|AAZ74614.1\|; | \|72602382\|gb\|AAZ74603.1\|; |
| \|72602363\|gb\|AAZ74592.1\|; | \|72602312\|gb\|AAZ74581.1\|; | \|72598259\|gb\|AAZ74570.1\|; |
| \|72597976\|gb\|AAZ74559.1\|; | \|72582199\|gb\|AAZ74548.1\|; | \|72581028\|gb\|AAZ74537.1\|; |
| \|72578717\|gb\|AAZ74526.1\|; | \|72572343\|gb\|AAZ74515.1\|; | \|72572222\|gb\|AAZ74504.1\|; |
| \|72569084\|gb\|AAZ74493.1\|; | \|72565969\|gb\|AAZ74482.1\|; | \|72562651\|gb\|AAZ74471.1\|; |
| \|72556693\|gb\|AAZ74460.1\|; | \|72554416\|gb\|AAZ74449.1\|; | \|72552919\|gb\|AAZ74438.1\|; |
| \|72552104\|gb\|AAZ74427.1\|; | \|72549761\|gb\|AAZ74416.1\|; | \|72545910\|gb\|AAZ74405.1\|; |
| \|72545373\|gb\|AAZ74394.1\|; | \|72543055\|gb\|AAZ74382.1\|; | \|72539904\|gb\|AAZ74371.1\|; |
| \|72539866\|gb\|AAZ74360.1\|; | \|71842601\|gb\|AAZ43413.1\|; | \|71842582\|gb\|AAZ43402.1\|; |
| \|71842563\|gb\|AAZ43391.1\|; | \|71842540\|gb\|AAZ43378.1\|; | \|71571169\|gb\|AAZ38658.1\|; |
| \|71568557\|gb\|AAZ38646.1\|; | \|71564894\|gb\|AAZ38635.1\|; | \|71564875\|gb\|AAZ38624.1\|; |
| \|71564856\|gb\|AAZ38613.1\|; | \|71564837\|gb\|AAZ38602.1\|; | \|71564818\|gb\|AAZ38591.1\|; |
| \|71564799\|gb\|AAZ38580.1\|; | \|71564780\|gb\|AAZ38569.1\|; | \|71564761\|gb\|AAZ38558.1\|; |
| \|71564742\|gb\|AAZ38547.1\|; | \|71564723\|gb\|AAZ38536.1\|; | \|71564704\|gb\|AAZ38525.1\|; |
| \|71564685\|gb\|AAZ38514.1\|; | \|71564666\|gb\|AAZ38503.1\|; | \|71564647\|gb\|AAZ38492.1\|; |
| \|71564628\|gb\|AAZ38481.1\|; | \|71564609\|gb\|AAZ38470.1\|; | \|62198882\|gb\|AAX76681.1\|; |
| \|68525456\|gb\|AAY98778.1\|; | \|68510091\|gb\|AAY98414.1\|; | \|68510073\|gb\|AAY98404.1\|; |
| \|68510053\|gb\|AAY98394.1\|; | \|68510022\|gb\|AAY98374.1\|; | \|68510001\|gb\|AAY98347.1\|; |
| \|68509974\|gb\|AAY98364.1\|; | \|68509908\|gb\|AAY98347.1\|; | \|68509883\|gb\|AAY98337.1\|; |
| \|68509389\|gb\|AAY98327.1\|; | \|68509351\|gb\|AAY98255.1\|; | \|68509326\|gb\|AAY98245.1\|; |
| \|68509307\|gb\|AAY98235.1\|; | \|68509287\|gb\|AAY98225.1\|; | \|68509263\|gb\|AAY98215.1\|; |
| \|68509240\|gb\|AAY98205.1\|; | \|68509224\|gb\|AAY98196.1\|; | \|68509201\|gb\|AAY98185.1\|; |
| \|68509182\|gb\|AAY98175.1\|; | \|68509164\|gb\|AAY98165.1\|; | \|68509146\|gb\|AAY98155.1\|; |
| \|68509127\|gb\|AAY98145.1\|; | \|68509109\|gb\|AAY98135.1\|; | \|68509091\|gb\|AAY98125.1\|; |
| \|68509073\|gb\|AAY98115.1\|; | \|68509055\|gb\|AAY98105.1\|; | \|68509028\|gb\|AAY98095.1\|; |
| \|68508949\|gb\|AAY98085.1\|; | \|68508910\|gb\|AAY98075.1\|; | \|68508833\|gb\|AAY98065.1\|; |
| \|68508618\|gb\|AAY98055.1\|; | \|68508532\|gb\|AAY98045.1\|; | \|67062609\|gb\|AAY64410.1\|; |
| \|67062088\|gb\|AAY64400.1\|; | \|67061918\|gb\|AAY64390.1\|; | \|67061126\|gb\|AAY64380.1\|; |
| \|67060437\|gb\|AAY64370.1\|; | \|67060204\|gb\|AAY64360.1\|; | \|67059004\|gb\|AAY64340.1\|; |
| \|67058941\|gb\|AAY64330.1\|; | \|67058361\|gb\|AAY64320.1\|; | \|67058343\|gb\|AAY64310.1\|; |
| \|67058325\|gb\|AAY64300.1\|; | \|67058307\|gb\|AAY64290.1\|; | \|67058289\|gb\|AAY64280.1\|; |
| \|67057788\|gb\|AAY64270.1\|; | \|67051428\|gb\|AAY64260.1\|; | \|67050142\|gb\|AAY64250.1\|; |
| \|67045900\|gb\|AAY64240.1\|; | \|67045484\|gb\|AAY64230.1\|; | \|67044535\|gb\|AAY64220.1\|; |
| \|67044368\|gb\|AAY64210.1\|; | \|67044270\|gb\|AAY64200.1\|; | \|67044170\|gb\|AAX57872.2\|; |
| \|66947428\|gb\|AAY59043.1\|; | \|66475132\|gb\|AAY47093.1\|; | \|66475070\|gb\|AAY47060.1\|; |
| \|66474984\|gb\|AAY47021.1\|; | \|66473609\|gb\|AAY46444.1\|; | \|66473591\|gb\|AAY46434.1\|; |
| \|66473573\|gb\|AAY46424.1\|; | \|66473503\|gb\|AAY46399.1\|; | \|66473481\|gb\|AAY46389.1\|; |
| \|66473461\|gb\|AAY46379.1\|; | \|66356029\|gb\|AAY45654.1\|; | \|66354538\|gb\|AAY44914.1\|; |
| \|66354520\|gb\|AAY44904.1\|; | \|66354426\|gb\|AAY44894.1\|; | \|66354022\|gb\|AAY44804.1\|; |
| \|66354002\|gb\|AAY44793.1\|; | \|66353984\|gb\|AAY44783.1\|; | \|66353884\|gb\|AAY44773.1\|; |
| \|66353866\|gb\|AAY44763.1\|; | \|66346643\|gb\|AAY44669.1\|; | \|66346057\|gb\|AAY44659.1\|; |
| \|66327477\|gb\|AAY44649.1\|; | \|66319071\|gb\|AAY44639.1\|; | \|66315260\|gb\|AAY44629.1\|; |
| \|66303399\|gb\|AAY44618.1\|; | \|63053695\|gb\|AAY28656.1\|; | \|63053677\|gb\|AAY28646.1\|; |
| \|63053659\|gb\|AAY28636.1\|; | \|63053641\|gb\|AAY28626.1\|; | \|63053623\|gb\|AAY28616.1\|; |
| \|63053540\|gb\|AAY28599.1\|; | \|63053508\|gb\|AAY28589.1\|; | \|63053490\|gb\|AAY28579.1\|; |
| \|63053471\|gb\|AAY28569.1\|; | \|63047712\|gb\|AAY28559.1\|; | \|63038408\|gb\|AAY28549.1\|; |
| \|63034469\|gb\|AAY28539.1\|; | \|63034451\|gb\|AAY28529.1\|; | \|63034238\|gb\|AAY28510.1\|; |
| \|63034207\|gb\|AAY28413.1\|; | \|63034189\|gb\|AAY28403.1\|; | \|63034170\|gb\|AAY28393.1\|; |
| \|63034134\|gb\|AAY28373.1\|; | \|63034118\|gb\|AAY28364.1\|; | \|63034098\|gb\|AAY28353.1\|; |
| \|63034080\|gb\|AAY28343.1\|; | \|63034062\|gb\|AAY28333.1\|; | \|63034044\|gb\|AAY28323.1\|; |
| \|63034026\|gb\|AAY28313.1\|; | \|63033985\|gb\|AAY28303.1\|; | \|63033967\|gb\|AAY28293.1\|; |
| \|63033949\|gb\|AAY28283.1\|; | \|63033929\|gb\|AAY28273.1\|; | \|63033426\|gb\|AAY28022.1\|; |
| \|63033408\|gb\|AAY28012.1\|; | \|63033389\|gb\|AAY28002.1\|; | \|63033344\|gb\|AAY27967.1\|; |
| \|63029999\|gb\|AAY27871.1\|; | \|63029981\|gb\|AAY27861.1\|; | \|63029961\|gb\|AAY27851.1\|; |
| \|62871493\|gb\|AAY18619.1\|; | \|62871301\|gb\|AAY18596.1\|; | \|62871275\|gb\|AAY18578.1\|; |
| \|62870095\|gb\|AAY18204.1\|; | \|62870077\|gb\|AAY18194.1\|; | \|62870059\|gb\|AAY18184.1\|; |
| \|62870041\|gb\|AAY18174.1\|; | \|62870023\|gb\|AAY18164.1\|; | \|62870005\|gb\|AAY18154.1\|; |
| \|62869987\|gb\|AAY18144.1\|; | \|62869969\|gb\|AAY18134.1\|; | \|62869951\|gb\|AAY18124.1\|; |
| \|62869933\|gb\|AAY18114.1\|; | \|62869915\|gb\|AAY18104.1\|; | \|62869896\|gb\|AAY18094.1\|; |
| \|62199044\|gb\|AAX76771.1\|; | \|62199026\|gb\|AAX76761.1\|; | \|62198972\|gb\|AAX76731.1\|; |
| \|62198954\|gb\|AAX76721.1\|; | \|62198918\|gb\|AAX76701.1\|; | \|62198900\|gb\|AAX76691.1\|; |
| \|62198864\|gb\|AAX76671.1\|; | \|62198846\|gb\|AAX76661.1\|; | \|62198828\|gb\|AAX76651.1\|; |
| \|62198792\|gb\|AAX76631.1\|; | \|61970950\|gb\|AAX57952.1\|; | \|61970932\|gb\|AAX57942.1\|; |

| PB1 proteins | | |
|---|---|---|
| |61970914|gb|AAX57932.1|; | |61970896|gb|AAX57922.1|; | |61970878|gb|AAX57912.1|; |
| |61970860|gb|AAX57902.1|; | |61970842|gb|AAX57892.1|; | |61970824|gb|AAX57882.1|; |
| |61970788|gb|AAX57862.1|; | |61970770|gb|AAX57852.1|; | |61970752|gb|AAX57842.1|; |
| |61970734|gb|AAX57832.1|; | |61970716|gb|AAX57822.1|; | |61970698|gb|AAX57812.1|; |
| |61970680|gb|AAX57802.1|; | |61970662|gb|AAX57792.1|; | |61970644|gb|AAX57782.1|; |
| |61970626|gb|AAX57772.1|; | |61970608|gb|AAX57762.1|; | |61970590|gb|AAX57752.1|; |
| |61970572|gb|AAX57742.1|; | |61970552|gb|AAX57731.1|; | |61970536|gb|AAX57722.1|; |
| |61970518|gb|AAX57712.1|; | |61970500|gb|AAX57702.1|; | |61970482|gb|AAX57692.1|; |
| |61970464|gb|AAX57682.1|; | |61970446|gb|AAX57672.1|; | |61970428|gb|AAX57662.1|; |
| |61970408|gb|AAX57651.1|; | |61928240|gb|AAX56608.1|; | |61928182|gb|AAX56598.1|; |
| |61928120|gb|AAX56588.1|; | |61928076|gb|AAX56578.1|; | |61928032|gb|AAX56568.1|; |
| |61927970|gb|AAX56558.1|; | |61927920|gb|AAX56548.1|; | |61927828|gb|AAX56528.1|; |
| |61927777|gb|AAX56518.1|; | |61927726|gb|AAX56508.1|; | |61927673|gb|AAX56498.1|; |
| |61927614|gb|AAX56488.1|; | |61927556|gb|AAX56478.1|; | |61927508|gb|AAX56468.1|; |
| |61927454|gb|AAX56458.1|; | |61927398|gb|AAX56448.1|; | |61927350|gb|AAX56438.1|; |
| |61927302|gb|AAX56428.1|; | |61927256|gb|AAX56418.1|; | |61927208|gb|AAX56408.1|; |
| |61927153|gb|AAX56398.1|; | |61927104|gb|AAX56388.1|; | |61621015|gb|AAX47543.1|; |
| |61620963|gb|AAX47533.1|; | |61620931|gb|AAX47523.1|; | |61104901|gb|AAX38245.1|; |
| |60738762|gb|AAX35879.1|; | |60738744|gb|AAX35869.1|; | |60738726|gb|AAX35859.1|; |
| |60738708|gb|AAX35849.1|; | |60738690|gb|AAX35839.1|; | |60738672|gb|AAX35829.1|; |
| |60683819|gb|AAX34070.1|; | |59940545|gb|AAX12819.1|; | |59940527|gb|AAX12809.1|; |
| |59940509|gb|AAX12799.1|; | |59940491|gb|AAX12789.1|; | |59940473|gb|AAX12779.1|; |
| |59940453|gb|AAX12769.1|; | |59940435|gb|AAX12759.1|; | |59940417|gb|AAX12749.1|; |
| |59940399|gb|AAX12739.1|; | |59896566|gb|AAX11643.1|; | |59896548|gb|AAX11633.1|; |
| |59896530|gb|AAX11623.1|; | |59896512|gb|AAX11613.1|; | |59896494|gb|AAX11603.1|; |
| |59896476|gb|AAX11593.1|; | |59896458|gb|AAX11583.1|; | |59896440|gb|AAX11573.1|; |
| |59896422|gb|AAX11563.1|; | |59896404|gb|AAX11553.1|; | |59896386|gb|AAX11543.1|; |
| |59896368|gb|AAX11533.1|; | |59896350|gb|AAX11523.1|; | |59896332|gb|AAX11513.1|; |
| |59896314|gb|AAX11503.1|; | |59896296|gb|AAX11493.1|; | |59896278|gb|AAX11483.1|; |
| |59896260|gb|AAX11473.1|; | |59896242|gb|AAX11463.1|; | |70907654|gb|AAX56539.2|; |
| |67059564|gb|AAY64350.1|; | |66475114|gb|AAY47083.1|; | |5732303|gb|AAD49027.1|AF156417_1|; |
| |62199008|gb|AAX76751.1|; | |50235443|gb|AAT70825.1|; | |50083052|gb|AAT70175.1|; |
| |51512158|gb|AAU05322.1|; | | |33318109|gb|AAQ04928.1|AF508639_1|; |
| |33318107|gb|AAQ04927.1|AF508635_1|; | | |33318105|gb|AAQ04926.1|AF508637_1|; |
| |33318103|gb|AAQ04925.1|AF508636_1|; | | |33318097|gb|AAQ04922.1|AF508633_1|; |
| |33318095|gb|AAQ04921.1|AF508632_1|; | | |33318091|gb|AAQ04919.1|AF508630_1|; |
| |33318089|gb|AAQ04918.1|AF508629_1|; | | |33318085|gb|AAQ04916.1|AF508627_1|; |
| |41207493|gb|AAR99632.1|; | |21902311|gb|AAM78509.1|AF483601_1|; | |18496104|emb|CAD20323.1|; |
| |12038896|emb|CAC19695.1|; | | |10442693|gb|AAG17436.1|AF285891_1|; |
| |9557185|gb|AAG01787.1|AF251429_1|; | | |9557168|gb|AAG01778.1|AF251421_1|; |
| |9557151|gb|AAG01769.1|AF251413_1|; | | |9557134|gb|AAG01760.1|AF251405_1|; |
| |9557117|gb|AAG01751.1|AF251397_1|; | | |9557103|gb|AAG01744.1|AF251390_1|; |
| |8894712|emb|CAB95865.1|; | |8894710|emb|CAB95864.1|; | |8894708|emb|CAB95863.1|; |
| |5515437|gb|AAF76001.1|AF250130_1|; | | |5732317|gb|AAD49034.1|AF156424_1|; |
| |5732327|gb|AAD49039.1|AF156429_1|; | | |5732319|gb|AAD49035.1|AF156425_1|; |
| |5732315|gb|AAD49033.1|AF156423_1|; | | |5732313|gb|AAD49032.1|AF156422_1|; |
| |5732311|gb|AAD49031.1|AF156421_1|; | | |5732309|gb|AAD49030.1|AF156420_1|; |
| |5732307|gb|AAD49029.1|AF156419_1|; | | |5732305|gb|AAD49028.1|AF156415_1|; |
| |5732301|gb|AAD49026.1|AF156416_1|; | |3722129|gb|AAC63454.1|; | |3722127|gb|AAC63453.1|; |
| |3722125|gb|AAC63452.1|; | |3722123|gb|AAC63451.1|; | |3722121|gb|AAC63450.1|; |
| |3722119|gb|AAC63449.1|; | |3721950|gb|AAC63412.1|; | |3721948|gb|AAC63411.1|; |
| |3721946|gb|AAC63410.1|; | |3721944|gb|AAC63409.1|; | |324978|gb|AAA19212.1|; |
| |324976|gb|AAA19211.1|; | |324974|gb|AAA19210.1|; | |58618430|gb|AAW80713.1|; |
| |58618428|gb|AAW80712.1|; | | |21636441|gb|AAM69995.1|AF457706_1|; |
| |21636405|gb|AAM69975.1|AF457690_1|; | | |21636387|gb|AAM69965.1|AF457682_1|; |
| |21636367|gb|AAM69954.1|AF457673_1|; | | |21636363|gb|AAM69952.1|AF457671_1|; |
| |324966|gb|AAA43644.1|; | |27596988|ref|NP_775530.1|; | |63054913|gb|AAY28993.1|; |
| |60547103|gb|AAX23573.1|; | |58618426|gb|AAW80711.1|; | |21693165|gb|AAM75156.1|AF389116_1|; |
| |14009686|gb|AAK51715.1|; | |14009684|gb|AAK51714.1|; | |9954393|gb|AAG09041.1|; |
| |324968|gb|AAA43645.1|; |324964|gb|AAA43643.1|; |324962|gb|AAA43642.1|; |324960|gb|AAA43641.1|; | | |
| |324958|gb|AAA43640.1|; |324956|gb|AAA43639.1|; |324954|gb|AAA43638.1|; |324952|gb|AAA43637.1|; | | |
| |324950|gb|AAA43636.1|; |324948|gb|AAA43635.1|; |324946|gb|AAA43634.1|; |324944|gb|AAA43633.1|; | | |
| |324942|gb|AAA43632.1|; |133503|sp|P27153|RRP1_DHVI1|; |279899|pir|A600081; |279898|pir|B60011|; | | |
| |67089|pir|P1IV61|; | |77917350|gb|ABB05224.1|; | |77917331|gb|ABB05213.1|; |
| |77917312|gb|ABB05202.1|; | |77869502|gb|ABB05191.1|; | |77863505|gb|ABB05013.1|; |
| |77863486|gb|ABB05002.1|; | |77863467|gb|ABB04991.1|; | |77863448|gb|ABB04980.1|; |
| |77863429|gb|ABB04969.1|; | |77863410|gb|ABB04958.1|; | |77863391|gb|ABB04947.1|; |
| |77863372|gb|ABB04936.1|; | |77863353|gb|ABB04925.1|; | |77863334|gb|ABB04914.1|; |
| |77861881|gb|ABB04379.1|; | |77861862|gb|ABB04368.1|; | |77861843|gb|ABB04357.1|; |
| |77861824|gb|ABB04346.1|; | |77861805|gb|ABB04335.1|; | |77861786|gb|ABB04324.1|; |
| |77861767|gb|ABB04313.1|; | |77861748|gb|ABB04302.1|; | |77861729|gb|ABB04291.1|; |
| |77747474|gb|ABB03153.1|; | |77747455|gb|ABB03142.1|; | |77747436|gb|ABB03131.1|; |
| |77747416|gb|ABB03120.1|; | |77747397|gb|ABB03109.1|; | |77747378|gb|ABB03098.1|; |
| |77747359|gb|ABB03087.1|; | |77747340|gb|ABB03076.1|; | |77747319|gb|ABB03065.1|; |
| |77747300|gb|ABB03054.1|; | |77747281|gb|ABB03043.1|; | |77747262|gb|ABB03032.1|; |
| |77747243|gb|ABB03021.1|; | |77747224|gb|ABB03010.1|; | |77747205|gb|ABB02999.1|; |
| |77747186|gb|ABB02988.1|; | |77747165|gb|ABB02977.1|; | |77747146|gb|ABB02966.1|; |

| PB1 proteins |||
|---|---|---|
| \|77747127\|gb\|ABB02955.1\|; | \|77747108\|gb\|ABB02944.1\|; | \|77747087\|gb\|ABB02932.1\|; |
| \|77747068\|gb\|ABB02921.1\|; | \|77747049\|gb\|ABB02910.1\|; | \|77747003\|gb\|ABB02899.1\|; |
| \|77746984\|gb\|ABB02888.1\|; | \|77746965\|gb\|ABB02877.1\|; | \|77746946\|gb\|ABB02866.1\|; |
| \|77746927\|gb\|ABB02855.1\|; | \|77746906\|gb\|ABB02844.1\|; | \|77746887\|gb\|ABB02833.1\|; |
| \|77746868\|gb\|ABB02822.1\|; | \|77746849\|gb\|ABB02811.1\|; | \|77746830\|gb\|ABB02800.1\|; |
| \|77746811\|gb\|ABB02789.1\|; | \|66733937\|gb\|AAY52743.1\|; | \|66733935\|gb\|AAY52742.1\|; |
| \|66733933\|gb\|AAY52741.1\|; | \|66733931\|gb\|AAY52740.1\|; | \|66733929\|gb\|AAY52739.1\|; |
| \|66733927\|gb\|AAY52738.1\|; | \|66733925\|gb\|AAY52737.1\|; | \|66733923\|gb\|AAY52736.1\|; |
| \|66733921\|gb\|AAY52735.1\|; | \|66733919\|gb\|AAY52734.1\|; | \|66733917\|gb\|AAY52733.1\|; |
| \|66733915\|gb\|AAY52732.1\|; | \|66733913\|gb\|AAY52731.1\|; | \|66733911\|gb\|AAY52730.1\|; |
| \|66733909\|gb\|AAY52729.1\|; | \|66733907\|gb\|AAY52728.1\|; | \|66733905\|gb\|AAY52727.1\|; |
| \|66733903\|gb\|AAY52726.1\|; | \|66733901\|gb\|AAY52725.1\|; | \|66733899\|gb\|AAY52724.1\|; |
| \|66733897\|gb\|AAY52723.1\|; | \|66733895\|gb\|AAY52722.1\|; | \|66733893\|gb\|AAY52721.1\|; |
| \|66733891\|gb\|AAY52720.1\|; | \|66733889\|gb\|AAY52719.1\|; | \|66733887\|gb\|AAY52718.1\|; |
| \|66733885\|gb\|AAY52717.1\|; | \|66733883\|gb\|AAY52716.1\|; | \|13925401\|gb\|AAK49363.1\|AF258827_1\|; |
| \|13274640\|gb\|AAK18014.1\|AF258823_1\|; | | \|13274638\|gb\|AAK18013.1\|AF258822_1\|; |
| \|50296446\|gb\|AAT73499.1\|; | | \|8307775\|gb\|AAF74316.1\|AF084266_1\|; |
| \|8307773\|gb\|AAF74315.1\|AF084265_1\|; | | \|8307771\|gb\|AAF74314.1\|AF084264_1\|; |
| \|73852949\|ref\|YP_308665.1\|; | \|71013490\|dbj\|BAE07199.1\|; | \|54610035\|gb\|AAV35116.1\|; |
| \|54299856\|gb\|AAV32652.1\|; | \|54299842\|gb\|AAV32644.1\|; | \|13925398\|gb\|AAK49362.1\|AF258826_1\|; |
| \|13925395\|gb\|AAK49361.1\|AF258825_1\|; | | \|13925392\|gb\|AAK49360.1\|AF258824_1\|; |
| \|13925389\|gb\|AAK49359.1\|AF258821_1\|; | | \|13925386\|gb\|AAK49358.1\|AF258820_1\|; |
| \|13925383\|gb\|AAK49357.1\|AF258819_1\|; | | \|13925380\|gb\|AAK49356.1\|AF258818_1\|; |
| \|13925377\|gb\|AAK49355.1\|AF258817_1\|; | | \|13925374\|gb\|AAK49354.1\|AF258816_1\|; |
| \|47156561\|gb\|AAT12168.1\|; | \|47156559\|gb\|AAT12167.1\|; | \|47156557\|gb\|AAT12166.1\|; |
| \|47156555\|gb\|AAT12165.1\|; | \|47156553\|gb\|AAT12164.1\|; | \|47156551\|gb\|AAT12163.1\|; |
| \|47156549\|gb\|AAT12162.1\|; | \|47156547\|gb\|AAT12161.1\|; | \|47156545\|gb\|AAT12160.1\|; |
| \|47156543\|gb\|AAT12159.1\|; | \|47156541\|gb\|AAT12158.1\|; | \|47156539\|gb\|AAT12157.1\|; |
| \|47156537\|gb\|AAT12156.1\|; | \|47156535\|gb\|AAT12155.1\|; | \|47156533\|gb\|AAT12154.1\|; |
| \|47156531\|gb\|AAT12153.1\|; | \|47156529\|gb\|AAT12152.1\|; | \|47156527\|gb\|AAT12151.1\|; |
| \|47156525\|gb\|AAT12150.1\|; | \|47156523\|gb\|AAT12149.1\|; | \|47156521\|gb\|AAT12148.1\|; |
| \|1430831\|emb\|CAA67498.1\|; | | \|19422189\|gb\|AAL87925.1\|AF455727_1\|; |
| \|19422183\|gb\|AAL87922.1\|AF455724_1\|; | | \|19422181\|gb\|AAL87921.1\|AF455723_1\|; |
| \|14532423\|gb\|AAK64188.1\|; | \|13661046\|emb\|CAC37002.1\|; | \|5805279\|gb\|AAD51923.1\|; |
| \|57916067\|gb\|AAW59406.1\|; | \|57916013\|gb\|AAW59396.1\|; | \|57915966\|gb\|AAW59388.1\|; |
| \|47716769\|gb\|AAT37561.1\|; | \|58531173\|dbj\|BAD89344.1\|; | \|58531153\|dbj\|BAD89333.1\|; |
| \|58531135\|db\|BAD89323.1\|; | \|58531117\|d\|BAD89313.1\|; | \|58531085\|db\|BAD89303.1\|; |
| \|50956624\|gb\|AAT90830.1\|; | \|50296498\|gb\|AAT73525.1\|; | \|50296468\|gb\|AAT73510.1\|; |
| \|50296462\|gb\|AAT73507.1\|; | \|50296458\|gb\|AAT73505.1\|; | \|50296456\|gb\|AAT73504.1\|; |
| \|50296454\|gb\|AAT73503.1\|; | \|50296452\|gb\|AAT73502.1\|; | \|50296450\|gb\|AAT73501.1\|; |
| \|50296448\|gb\|AAT73500.1\|; | \|50296444\|gb\|AAT73498.1\|; | \|50296440\|gb\|AAT73496.1\|; |
| \|50296438\|gb\|AAT73495.1\|; | \|50296436\|gb\|AAT73494.1\|; | \|50296432\|gb\|AAT73492.1\|; |
| \|50296430\|gb\|AAT73491.1\|; | \|50296428\|gb\|AAT73490.1\|; | \|50296416\|gb\|AAT73484.1\|; |
| \|50296414\|gb\|AAT73483.1\|; | \|50296412\|gb\|AAT73482.1\|; | \|37963694\|gb\|AAR05984.1\|; |
| \|37963692\|gb\|AAR05983.1\|; | \|37963696\|gb\|AAR05985.1\|; | \|38524562\|dbj\|BAD02360.1\|; |
| \|38524542\|dbj\|BAD02349.1\|; | \|24286097\|gb\|AAN46833.1\|; | \|61612044\|gb\|AAX47280.1\|; |
| \|61612038\|gb\|AAX47279.1\|; | \|71000178\|db\|BAE07153.1\|; | \|30025725\|gb\|AAP04506.1\|; |
| \|70905275\|gb\|AAZ14161.1\|; | \|70905273\|gb\|AAZ14160.1\|; | \|70905271\|gb\|AAZ14159.1\|; |
| \|70905269\|gb\|AAZ14158.1\|; | \|70905267\|gb\|AAZ14157.1\|; | \|70905265\|gb\|AAZ14156.1\|; |
| \|70905263\|gb\|AAZ14155.1\|; | \|70905261\|gb\|AAZ14154.1\|; | \|70905259\|gb\|AAZ14153.1\|; |
| \|70905257\|gb\|AAZ14152.1\|; | \|70905255\|gb\|AAZ14151.1\|; | \|70905253\|gb\|AAZ14150.1\|; |
| \|3335435\|gb\|AAC32096.1\|; | \|3335415\|gb\|AAC32085.1\|; | \|56548870\|gb\|AAV97600.1\|; |
| \|56548868\|gb\|AAV97599.1\|; | \|56548866\|gb\|AAV97598.1\|; | \|56548864\|gb\|AAV97597.1\|; |
| \|56424948\|gb\|AAV91207.1\|; | \|56424946\|gb\|AAV91206.1\|; | \|56424942\|gb\|AAV91204.1\|; |
| \|50542650\|gb\|AAT78590.1\|; | \|50365727\|gb\|AAT76165.1\|; | \|47834828\|gb\|AAT39049.1\|; |
| \|47834824\|gb\|AAT39047.1\|; | \|47834822\|gb\|AAT39046.1\|; | \|47834814\|gb\|AAT39042.1\|; |
| \|47834812\|gb\|AAT39041.1\|; | \|40732896\|emb\|CAF04464.1\|; | \|14275693\|emb\|CAC40038.1\|; |
| \|13383273\|dbj\|BAB39508.1\|; | \|13383271\|dbj\|BAB39507.1\|; | \|13661044\|emb\|CAC37001.1\|; |
| \|28823019\|gb\|AAO46889.1\|; | \|28822828\|gb\|AAO46888.1\|; | \|28822609\|gb\|AAO46887.1\|; |
| \|28822076\|gb\|AAO46886.1\|; | \|28821871\|gb\|AAO46888.1\|; | \|28821644\|gb\|AAO46884.1\|; |
| \|28821462\|gb\|AAO46883.1\|; | \|28821280\|gb\|AAO46882.1\|; | \|28821223\|gb\|AAO46881.1\|; |
| \|27462113\|gb\|AAO15325.1\|AF225521_1\|; | | \|27462111\|gb\|AAO15324.1\|AF225520_1\|; |
| \|27462109\|gb\|AAO15323.1\|AF225519_1\|; | | \|27462107\|gb\|AAO15322.1\|AF225518_1\|; |
| \|21359664\|gb\|AAM49557.1\|AF468839_1\|; | \|20068025\|emb\|CAC84758.1\|; | \|20068023\|emb\|CAC84686.1\|; |
| \|20068021\|emb\|CAC84787.1\|; | \|20068019\|emb\|CAC84786.1\|; | \|20068017\|emb\|CAC84788.1\|; |
| \|20068015\|emb\|CAC84784.1\|; | \|20068007\|emb\|CAC84780.1\|; | \|19697848\|gb\|AAL31428.1\|; |
| \|19697846\|gb\|AAL31424.1\|; | \|19697836\|gb\|AAL31419.1\|; | \|19422195\|gb\|AAL87928.1\|AF455730_1\|; |
| \|19422193\|gb\|AAL87927.1\|AF455729_1\|; | | \|19422191\|gb\|AAL87926.1\|AF455728_1\|; |
| \|19422187\|gb\|AAL87924.1\|AF455726_1\|; | | \|19422185\|gb\|AAL87923.1\|AF455728_1\|; |
| \|16076717\|gb\|AAL14089.1\|AF222819_1\|; | | \|16076715\|gb\|AAL14088.1\|AF222818_1\|; |
| \|13661048\|emb\|CAC37003.1\|; | | \|8482850\|gb\|AAF75122.1\|AF115293_1\|; |
| \|8452848\|gb\|AAF75121.1\|AF115292_1\|; | \|323669\|gb\|AAA42968.1\|; | \|133517\|sp\|P16508\|RRP1_IAMAN\|; |
| \|133523\|sp\|P03430\|RRP1_IAWI1\|; | | \|2806782\|sp\|P16506\|RRP1_IAKOR\|; |
| \|133527\|sp\|P16512\|RRP1_IAZTF\|; | | \|1 33526\|sp\|P16510\|RRP1_IAZON\|; |
| \|133525\|sp\|P16509\|RRP1_IAZH3\|; | | \|133524\|sp\|P16514\|RRP1_IAWIS\|; |
| \|133522\|sp\|P16513\|RRP1_IATKM\|; | | \|1133521\|sp\|P16511\|RRP1_IASIN\|; |
| \|133518\|sp\|P16507\|RRP1_IAME8\|; | | \|133512\|sp\|P18882\|RRP1_IAKIE\|; |

-continued

| PB1 proteins | |
|---|---|
| \|133511\|sp\|P16505\|RRP1_IAHTE\|; | \|133510\|sp\|P16504\|RRP1_IAHLO\|; |
| \|133509\|sp\|P16503\|RRP1_IAGU2\|; | \|133506\|sp\|P16502\|RRP1_IABE1\|; |
| \|8647779\|sp\|Q82571\|RRP1_IAFOM\|; | \|6647775\|sp\|O91741\|RRP1_IAKIT\|; |
| \|8647773\|sp\|O89749\|RRP1_IACKH\|; | \|133531\|sp\|P19703\|RRP1_INCJJ\|; |
| \|133520\|sp\|P03431\|RRP1_IAPUE\|; | \|133519\|sp\|P03432\|RRP1_IANT6\|; |
| \|133505\|sp\|P21426\|RRP1_IAANN\|;   \|401026\|sp\|P31341\|RRP1_IAV17\|; | \|133516\|sp\|P26121\|RRP1_IALE3\|; |
| \|133515\|sp\|P26120\|RRP1_IALE2\|; | \|133514\|sp\|P26119\|RRP1_IALE1\|; |
| \|133508\|sp\|P26118\|RRP1_IADUN\|;   \|34733402\|gb\|AAQ81638.1\|; | \|34733400\|gb\|AAQ81637.1\|; |
| \|9863938\|gb\|AAG01228.1\|AF216740_1\|; | \|9863920\|gb\|AAG01218.1\|AF216732_1\|; |
| \|9863902\|gb\|AAG01208.1\|AF216724_1\|; | \|9863883\|gb\|AAG01198.1\|AF216716_1\|; |
| \|324980\|gb\|AAA43647.1\|; \|324970\|gb\|AAA43646.1 | |

The preferred influenza strains referred to in the present invention, for example against which the present polypeptides should be immunogenic, are those containing these specific proteins. The above accession numbers specify explicitly the identity of the strain in addition to the specific protein sequence.

In some preferred embodiments the polypeptide according to the present invention may comprise one or more sequences as described above and having at least 60% homology with a consensus sequence over known human and avian influenza virus strains (or two or more epitopes of 7 amino acids or more having at least 60% homology with such a sequence). In further preferred embodiments the polypeptide may comprise one or more sequences as described above and having at least 60% homology with a consensus sequence over known human influenza virus strains (or two or more epitopes of 7 amino acids or more having at least 60% homology with such a sequence).

The percent homology of a first polypeptide sequence to a second polypeptide sequence, as referred to in the context of the present invention, is defined as the number of amino acid residues in the second sequence that match in both position and identity to those in the first sequence, divided by the total number of amino acid residues in the second polypeptide (both first and second polypeptides must have the same number of amino acid residues) and multiplied by 100. In the present invention, it is preferred that the polypeptide homology to the defined sequences is 75% or more, 85% or more, 95% or more or 100% (or substantially 100%).

The epitopes within the sequences defined above are not especially limited, provided that they contain 7 amino acid residues or more. Preferably the epitopes are of a length that is appropriate for CTL epitopes in a particular vertebrate species, such as in a human, having a specific MHC. Typically the epitopes contain 8, 9, 10, or 11 amino acid residues, but may contain more if desired. Generally an appropriate epitope is one which is a CTL epitope in a vertebrate such as a human.

Typically, the polypeptide comprises between 7 and 100 amino acids, and preferably from 8-50 amino acids. The size should not be so great that useful epitopes suffer from competition with non-protective epitopes in the immune system (for this reason full proteins are not included), nor should the size be so small that only a very narrow range of protection is offered. More preferred ranges are from 8-40 amino acids, 15-40 amino acids and 15-35 amino acids. The most preferred length is from 20-35 amino acid residues. It is particularly preferred that the polypeptide consists of (or substantially consists of) a sequence selected from the sequences at the positions defined above in the specific list of proteins set out above.

In addition to the polypeptides described above, which should not be larger than 100 amino acid residues in length, the invention also provides multi-epitope immunogenic polypeptides comprising two or more polypeptides of the present invention. These multi-epitope polypeptides are not limited in size. Thus, they extend not only to the polypeptides having from 7-100 amino acid residues as outlined above, but also to larger polypeptides, provided that these larger polypeptides comprise two or more units, each unit consisting of a polypeptide of the invention. Thus, a polypeptide having 100 repeating units of a 7-mer according to the present invention is encompassed by the present invention, as is a polypeptide having, say 52 units of one 8-mer epitope, and 23 units of a second 10-mer epitope. Polypeptides of this type will not suffer from the competition problems associated with similar length polypeptides that comprise only one or two epitopes. For the avoidance of doubt, the multi-epitope polypeptide may comprise multiple copies of the same epitope, or single copies of a plurality of different epitopes, or multiple copies of 2 or more epitopes.

Also provided by the invention is a polypeptide composition comprising two or more different polypeptides as defined above. Thus, the polypeptide composition may comprise any number of polypeptides of the present invention together in the same mixture or formulation. The presence of a plurality of polypeptides together is useful since each may elicit its own immune response, widening the protective effect of the composition. It is particularly preferred that the composition contains all of the sequences of SEQ ID 1-6 either each in a separate peptide or several in a smaller number of peptides (e.g. 3 combined in one larger peptide and the other three 3 in another larger peptide, etc.).

The invention also provides a polypeptide construct, which construct comprises a polypeptide as defined above and a carrier. The construct may be formed by combining two or more epitopes and/or a polypeptide as defined above with the carrier. The carrier may be a molecule, such as an adjuvant and/or an excipient. Combining in this context means either mixing together, or attaching together (e.g. via a covalent linkage).

The present invention further provides a polypeptide as defined above for use in medicine. Also provided is a medicament or vaccine composition against influenza, comprising a polypeptide as defined above, and one or more appropriate excipients and/or adjuvants, or a polypeptide construct as defined above and optionally one or more appropriate excipients and/or adjuvants (if the carrier part of the construct is itself an excipient or adjuvant, then a further excipient or adjuvant may not be needed). The excipient or adjuvant is not especially limited, and any excipients or adjuvants used in medicaments and vaccines may be employed. The medicament or vaccine composition may be produced according to any known method appropriately adapted to the present invention, such as by mixing a polypeptide of the invention with an appropriate excipient.

A method of producing a polypeptide as defined above is also provided by the invention. The method is not especially limited, and typically comprises joining two or more epitopes to form the polypeptide. The polypeptide may, however, be synthesised by direct chemical synthesis (e.g. incorporating one amino acid at a time until the full polypeptide is formed) or by recombinant methods. Such general methods are well known to the skilled person and may be adapted to the present invention as desired. In some instances, the polypeptide of the present invention may comprise additional amino acid sequences at one or both termini to help in synthesis of the polypeptide. These additional sequences are preferably from 1-5 amino acids in length. Typically 3 amino acids are involved. For example, in one preferred embodiment, SEQ ID 6 comprises the amino acids AAS immediately prior to the IIG part of the sequence.

The invention still further provides use of a polypeptide or composition as defined above, in the manufacture of a medicament or vaccine, effective in the treatment or prevention of influenza. Also provided is a method of treating or preventing influenza, which method comprises administering a polypeptide, a composition, a medicament or a vaccine as defined above to a vertebrate. The method of administration is not especially limited, and may comprise subcutaneous, intramuscuscular, intra-venous, intra-dermal, or intra-nasal administration, or may be administered orally (e.g. in the form of a pill or a liquid preparation), or may be in the form of a suppository, if desired. The form of such administration preparations is not especially limited, and known forms may be employed with appropriate modifications that will be apparent to the skilled person. The dosage is not especially limited and may range from 1 µg to 100 g of the polypeptide per individual, depending upon the size, weight and species of the individual involved.

The invention may be applied to any vertebrate, since the immune systems of vertebrates operate in a related manner. Typically, the vertebrate referred to in the present context is a mammal, bird, a reptile or a fish. It is especially preferred that the vertebrate is a human, a domestic animal (such as a dog or a cat), a farm animal (such as a pig or a horse), a bovine animal (such as cattle, or a cow), or fowl (such as a domestic bird, a farm bird, or a game bird). When the vertebrate is a bird, it is preferably a chicken, a turkey, a duck, or a goose.

Examples of human MHCs (HLAs) that may be employed with the present invention include the following:

HLA-A

A*010101, A*010102, A*010103, A*0102, A*0103, A*0104N, A*0106, A*0107, A*0108, A*0109, A*0110, A*02010101, A*02010102L, A*020102, A*020103, A*020104, A*020105, A*020106, A*020107, A*020108, A*020109, A*020110, A*020111, A*0202, A*020301, A*020302, A*0204, A*0205, A*020601, A*020602, A*020603, A*0207, A*0208, A*0209, A*0210, A*0211, A*0212, A*0213, A*0214, A*0215N, A*0216, A*021701, A*021702, A*0218, A*0219, A*022001, A*022002, A*0221, A*0222, A*0224, A*0225, A*0226, A*0227, A*0228, A*0229, A*0230, A*0231, A*0232N, A*0233, A*0234, A*023501, A*023502, A*0236, A*0237, A*0238, A*0239, A*0240, A*0241, A*0242, A*0243N, A*0244, A*0245, A*0246, A*0247, A*0248, A*0249, A*0250, A*0251, A*0252, A*0253N, A*0254, A*0255, A*0256, A*0257, A*0258, A*0259, A*0260, A*0261, A*0262, A*0263, A*0264, A*0265, A*0266, A*0267, A*0268, A*0269, A*0270, A*0271, A*0272, A*0273, A*03010101, A*03010102N, A*03010103, A*030102, A*030103, A*0302, A*0303N, A*0304, A*0305, A*0306, A*0307, A*0308, A*0309, A*0310, A*0311N, A*0312, A*0313, A*0314, A*110101, A*110102, A*1102, A*1103, A*1104, A*1105, A*1106, A*1107, A*1108, A*1109, A*1110, A*1111, A*1112, A*1113, A*1114, A*1115, A*1116, A*1117, A*1118, A*119, A*2301, A*2302, A*2303, A*2304, A*2305, A*2306, A*2307N, A*2308N, A*2309, A*2310, A*2311N, A*2312, A*24020101, A*24020102L, A*240202, A*240203, A*240204, A*240205, A*240206, A*240301, A*240302, A*2404, A*2405, A*2406, A*2407, A*2408, A*2409N, A*2410, A*2411N, A*2413, A*2414, A*2415, A*2417, A*2418, A*2419, A*2420, A*2421, A*2422, A*2423, A*2424, A*2425, A*2426, A*2427, A*2428, A*2429, A*2430, A*2431, A*2432, A*2433, A*2434, A*2435, A*2436N, A*2437, A*2438, A*2439, A*2440N, A*2441, A*2442, A*2443, A*2444, A*2445N, A*2446, A*250101, A*250102, A*2502, A*2503, A*2504, A*2601, A*2602, A*2603, A*2604, A*2605, A*2606, A*260701, A*260702, A*2608, A*2609, A*2610, A*2611N, A*2612, A*2613, A*2614, A*2615, A*2616, A*2617, A*2618, A*2619, A*2620, A*2621, A*2622, A*2623, A*29010101, A*29010102N, A*290201, A*290202, A*290203, A*2903, A*2904, A*2905, A*2906, A*2907, A*2908N, A*2909, A*2910, A*2911, A*300101, A*300102, A*300201, A*300202, A*3003, A*3004, A*3006, A*3007, A*3008, A*3009, A*3010, A*3011, A*3012, A*310102, A*3102, A*3103, A*3104, A*3105, A*3106, A*3107, A*3108, A*3109, A*3110, A*3201, A*3202, A*3203, A*3204, A*3205, A*3206, A*3207, A*3208, A*3301, A*330301, A*330302, A*3304, A*3305, A*3306, A*3307, A*3401, A*3402, A*3403, A*3404, A*3405, A*3406, A*3601, A*3602, A*3603, A*3604, A*4301, A*6601, A*6602, A*6603, A*6604, A*680101, A*680102, A*680103, A*6802, A*680301, A*680302, A*6804, A*6805, A*6806, A*6807, A*6808, A*6809, A*6810, A*6811N, A*6812, A*6813, A*6814, A*6815, A*6816, A*6817, A*6818N, A*6819, A*6820, A*6821, A*6822, A*6823, A*6824, A*6825, A*6826, A*6827, A*6901, A*7401, A*7402, A*7403, A*7404, A*7405, A*7406, A*7407, A*7408, A*7409, A*7410, A*8001.

HLA-B

B*070201, B*070202, B*070203, B*070204, B*0703, B*0704, B*0705, B*0706, B*0707, B*0708, B*0709, B*0710, B*0711, B*0712, B*0713, B*0714, B*0715, B*0716, B*0717, B*0718, B*0719, B*0720, B*0721, B*0722, B*0723, B*0724, B*0725, B*0726, B*0727, B*0728, B*0729, B*0730, B*0731, B*0732, B*0733, B*0734, B*0735, B*0736, B*0737, B*0738, B*0801, B*0802, B*0803, B*0804, B*0805, B*0806, B*0807, B*0808N, B*0809, B*0810, B*0811, B*0812, B*0813, B*0814, B*0815, B*0816, B*0817, B*0818, B*0819N, B*0820, B*0821, B*0822, B*1301, B*1302, B*1303, B*1304, B*1306, B*1307N, B*1308, B*1309, B*1310, B*1311, B*1312, B*1313, B*1401, B*1402, B*1403, B*1404, B*1405, B*140601, B*140602, B*15010101, B*15010102N, B*150102, B*150103, B*150104, B*150105, B*1502, B*1503, B*1504, B*1505, B*1506, B*1507, B*1508, B*1509, B*1510, B*151101, B*151102, B*1512, B*1513, B*1514, B*1515, B*1516, B*15170101, B*15170102, B*1518, B*1519, B*1520, B*1521, B*1523, B*1524, B*1525, B*1526N, B*1527, B*1528, B*1529, B*1530, B*1531, B*1532, B*1533, B*1534, B*1535, B*1536, B*1537, B*1538, B*1539, B*1540, B*1542, B*1543, B*1544, B*1545, B*1546, B*1547, B*1548,

B*1549, B*1550, B*1551, B*1552, B*1553, B*1554, B*1555, B*1556, B*1557, B*1558, B*1560, B*1561, B*1562, B*1563, B*1564, B*1565, B*1566, B*1567, B*1568, B*1569, B*1570, B*1571, B*1572, B*1573, B*1574, B*1575, B*1576, B*1577, B*1578, B*1579N, B*1580, B*1581, B*1582, B*1583, B*1584, B*1585, B*1586, B*1587, B*1588, B*1589, B*1590, B*1591, B*1592, B*1593, B*1594N, B*180101, B*180102, B*1802, B*1803, B*1804, B*1805, B*1806, B*1807, B*1808, B*1809, B*1810, B*1811, B*1812, B*1813, B*1814, B*1815, B*1817N, B*1818, B*1819, B*1820, B*2701, B*2702, B*2703, B*2704, B*270502, B*270503, B*270504, B*270505, B*270506, B*270507, B*2706, B*2707, B*2708, B*2709, B*2710, B*2711, B*2712, B*2713, B*2714, B*2715, B*2716, B*2717, B*2718, B*2719, B*2720, B*2721, B*2723, B*2724, B*2725, B*2726, B*350101, B*350102, B*3502, B*3503, B*3504, B*3505, B*3506, B*3507, B*3508, B*350901, B*350902, B*3510, B*3511, B*3512, B*3513, B*351401, B*351402, B*3515, B*3516, B*3517, B*3518, B*3519, B*3520, B*3521, B*3522, B*3523, B*3524, B*3525, B*3526, B*3527, B*3528, B*3529, B*3530, B*3531, B*3532, B*3533, B*3534, B*3535, B*3536, B*3537, B*3538, B*3539, B*3540N, B*3541, B*3542, B*3543, B*3544, B*3545, B*3546, B*3547, B*3548, B*3549, B*3550, B*3551, B*3552, B*3553N, B*3701, B*3702, B*3703N, B*3704, B*3705, B*3706, B*3707, B*3801, B*380201, B*380202, B*3803, B*3804, B*3805, B*3806, B*3807, B*3808, B*3809, B*3810, B*390101, B*390103, B*390104, B*390201, B*390202, B*3903, B*3904, B*3905, B*390601, B*390602, B*3907, B*3908, B*3909, B*3910, B*3911, B*3912, B*3913, B*3914, B*3915, B*3916, B*3917, B*3918, B*3919, B*3920, B*3922, B*3923, B*3924, B*3925N, B*3926, B*3927, B*3928, B*3929, B*3930, B*3931, B*3932, B*400101, B*400102, B*400103, B*400104, B*400105, B*400201, B*400202, B*4003, B*4004, B*4005, B*40060101, B*40060102, B*4007, B*4008, B*4009, B*4010, B*4011, B*4012, B*4013, B*401401, B*401402, B*401403, B*4015, B*4016, B*4018, B*4019, B*4020, B*4021, B*4022N, B*4023, B*4024, B*4025, B*4026, B*4027, B*4028, B*4029, B*4030, B*4031, B*4032, B*4033, B*4034, B*4035, B*4036, B*4037, B*4038, B*4039, B*4040, B*4042, B*4043, B*4044, B*4045, B*4046, B*4047, B*4048, B*4049, B*4050, B*4051, B*4052, B*4053, B*4054, B*4055, B*4056, B*4057, B*4101, B*4102, B*4103, B*4104, B*4105, B*4106, B*4201, B*4202, B*4204, B*420501, B*420502, B*4206, B*44020101, B*440201025, B*440202, B*440203, B*440301, B*440302, B*4404, B*4405, B*4406, B*4407, B*4408, B*4409, B*4410, B*4411, B*4412, B*4413, B*4414, B*4415, B*4416, B*4417, B*4418, B*4419N, B*4420, B*4421, B*4422, B*4423N, B*4424, B*4425, B*4426, B*4427, B*4428, B*4429, B*4430, B*4431, B*4432, B*4433, B*4434, B*4435, B*4436, B*4437, B*4438, B*4439, B*4440, B*4501, B*4502, B*4503, B*4504, B*4505, B*4506, B*4507, B*4601, B*4602, B*4603, B*4604, B*47010101, B*47010102, B*4702, B*4703, B*4704, B*4705, B*4801, B*4802, B*4803, B*4804, B*4805, B*4806, B*4807, B*4808, B*4809, B*4810, B*4901, B*4902, B*4903, B*5001, B*5002, B*5004, B*510101, B*510102, B*510103, B*510104, B*510105, B*510201, B*510202, B*5103, B*5104, B*5105, B*5106, B*5107, B*5108, B*5109, B*5110, B*5111N, B*5112, B*511301, B*511302, B*5114, B*5115, B*5116, B*5117, B*5118, B*5119, B*5120, B*5121, B*5122, B*5123, B*5124, B*5126, B*5127N, B*5128, B*5129, B*5130, B*5131, B*5132, B*5133, B*5134, B*5135, B*5136, B*520101, B*520102, B*520103, B*520104, B*5202, B*5203, B*5204, B*5205, B*5206, B*530101, B*530102, B*5302, B*5303, B*5304, B*5305, B*5306, B*5307, B*5308, B*5309, B*5401, B*5402, B*5501, B*5502, B*5503, B*5504, B*5505, B*5507, B*5508, B*5509, B*5510, B*5511, B*5512, B*5513, B*5514, B*5515, B*5516, B*5601, B*5602, B*5603, B*5604, B*560501, B*560502, B*5606, B*5607, B*5608, B*5609, B*5610, B*5611, B*5612, B*5613, B*5614, B*570101, B*570102, B*5702, B*570301, B*570302, B*5704, B*5705, B*5706, B*5707, B*5708, B*5709, B*5801, B*5802, B*5804, B*5805, B*5806, B*5807, B*5808, B*5809, B*5810N, B*5901, B*670101, B*670102, B*6702, B*7301, B*7801, B*780201, B*780202, B*7803, B*7804, B*7805, B*8101, B*8102, B*8201, B*8202, B*8301.

HLA-C

Cw*010201, Cw*010202, Cw*0103, Cw*0104, Cw*0105, Cw*0106, Cw*0107, Cw*0108, Cw*0109, Cw*0110, Cw*020201, Cw*020202, Cw*020203, Cw*020204, Cw*020205, Cw*0203, Cw*0204, Cw*0205, Cw*0206, Cw*0207, Cw*0208, Cw*0209, Cw*030201, Cw*030202, Cw*030301, Cw*030302, Cw*030303, Cw*030304, Cw*030401, Cw*030402, Cw*030403, Cw*0305, Cw*0306, Cw*0307, Cw*0308, Cw*0309, Cw*0310, Cw*0311, Cw*0312, Cw*0313, Cw*0314, Cw*0315, Cw*0316, Cw*0317, Cw*0318, Cw*04010101, Cw*04010102, Cw*040102, Cw*0403, Cw*040401, Cw*040402, Cw*0405, Cw*0406, Cw*0407, Cw*0408, Cw*0409N, Cw*0410, Cw*0411, Cw*0412, Cw*0413, Cw*0414, Cw*0415, Cw*050101, Cw*050102, Cw*0502, Cw*0503, Cw*0504, Cw*0505, Cw*0506, Cw*0507N, Cw*0508, Cw*0509, Cw*0510, Cw*0602, Cw*0603, Cw*0604, Cw*0605, Cw*0606, Cw*0607, Cw*0608, Cw*0609, Cw*0610, Cw*0611, Cw*070101, Cw*070102, Cw*070103, Cw*07020101, Cw*07020102, Cw*07020103, Cw*0703, Cw*070401, Cw*070402, Cw*0705, Cw*0706, Cw*0707, Cw*0708, Cw*0709, Cw*0710, Cw*0711, Cw*0712, Cw*0713, Cw*0714, Cw*0715, Cw*0716, Cw*0717, Cw*0718, Cw*0719, Cw*0720, Cw*0721, Cw*0722, Cw*0723, Cw*0724, Cw*0725, Cw*0726, Cw*0727, Cw*0728, Cw*0729, Cw*080101, Cw*080102, Cw*0802, Cw*0803, Cw*0804, Cw*0805, Cw*0806, Cw*0807, Cw*0808, Cw*0809, Cw*0810, Cw*0811, Cw*0812, Cw*120201, Cw*120202, Cw*120203, Cw*120301, Cw*120302, Cw*120303, Cw*120401, Cw*120402, Cw*1205, Cw*1206, Cw*1207, Cw*1208, Cw*1209, Cw*1210, Cw*1211, Cw*1212, Cw*1213, Cw*1214, Cw*1215, Cw*140201, Cw*140202, Cw*140203, Cw*1403, Cw*1404, Cw*1405, Cw*150201, Cw*150202, Cw*1503, Cw*1504, Cw*150501, Cw*150502, Cw*150503, Cw*150504, Cw*1506, Cw*1507, Cw*1508, Cw*1509, Cw*1510, Cw*1511, Cw*1512, Cw*1601, Cw*1602, Cw*160401, Cw*1606, Cw*1701, Cw*1702, Cw*1703, Cw*1801, Cw*1802.

HLA-E

E*0101, E*010301, E*010302, E*010303, E*0104.

HLA-F

F*010101, F*010102.

HLA-G

G*010101, G*010102, G*010103, G*010104, G*010105, G*010106, G*010107, G*010108, G*0102, G*0103, G*010401, G*010402, G*010403, G*0105N, G*0106.

HLA-DRA

DRA*0101, DRA*010201, DRA*010202.

HLA-DRB1

DRB1*010101, DRB1*010102, DRB1*010103, DRB1*010201, DRB1*010202, DRB1*010203, DRB1*010204, DRB1*0103, DRB1*0104, DRB1*0105, DRB1*0106, DRB1*0107, DRB1*0108, DRB1*0109, DRB1*0110, DRB1*0111, DRB1*030101, DRB1*030102, DRB1*030201, DRB1*030202, DRB1*0303, DRB1*0304, DRB1*030501, DRB1*030502, DRB1*0306, DRB1*0307, DRB1*0308, DRB1*0309, DRB1*0310, DRB1*0311, DRB1*0312, DRB1*0313, DRB1*0314, DRB1*0315, DRB1*0316, DRB1*0317, DRB1*0318, DRB1*0319, DRB1*0320, DRB1*0321, DRB1*0322, DRB1*0323, DRB1*0324, DRB1*0325, DRB1*0326, DRB1*0327, DRB1*0328, DRB1*040101, DRB1*040102, DRB1*0402, DRB1*040301, DRB1*040302, DRB1*0404, DRB1*040501, DRB1*040502, DRB1*040503, DRB1*040504, DRB1*0406, DRB1*040701, DRB1*040702, DRB1*040703, DRB1*0408, DRB1*0409, DRB1*0410, DRB1*0411, DRB1*0412, DRB1*0413, DRB1*0414, DRB1*0415, DRB1*0416, DRB1*0417, DRB1*0418, DRB1*0419, DRB1*0420, DRB1*0421, DRB1*0422, DRB1*0423, DRB1*0424, DRB1*0425, DRB1*0426, DRB1*0427, DRB1*0428, DRB1*0429, DRB1*0430, DRB1*0431, DRB1*0432, DRB1*0433, DRB1*0434, DRB1*0435, DRB1*0436, DRB1*0437, DRB1*0438, DRB1*0439, DRB1*0440, DRB1*0441, DRB1*0442, DRB1*0443, DRB1*0444, DRB1*0445, DRB1*0446, DRB1*0447, DRB1*0448, DRB1*0449, DRB1*0450, DRB1*070101, DRB1*070102, DRB1*0703, DRB1*0704, DRB1*0705, DRB1*0706, DRB1*0707, DRB1*0708, DRB1*080101, DRB1*080102, DRB1*080201, DRB1*080202, DRB1*080203, DRB1*080302, DRB1*080401, DRB1*080402, DRB1*080403, DRB1*080404, DRB1*0805, DRB1*0806, DRB1*0807, DRB1*0808, DRB1*0809, DRB1*0810, DRB1*0811, DRB1*0812, DRB1*0813, DRB1*0814, DRB1*0815, DRB1*0816, DRB1*0817, DRB1*0818, DRB1*0819, DRB1*0820, DRB1*0821, DRB1*0822, DRB1*0823, DRB1*0824, DRB1*0825, DRB1*0826, DRB1*0827, DRB1*0828, DRB1*0829, DRB1*090102, DRB1*090103, DRB1*0902, DRB1*0903, DRB1*100101, DRB1*100102, DRB1*110101, DRB1*110102, DRB1*110103, DRB1*110104, DRB1*110105, DRB1*1102, DRB1*1103, DRB1*110401, DRB1*110402, DRB1*1105, DRB1*110601, DRB1*110602, DRB1*1107, DRB1*110801, DRB1*110802, DRB1*1109, DRB1*1110, DRB1*1111, DRB1*111201, DRB1*111202, DRB1*1113, DRB1*1114, DRB1*1115, DRB1*1116, DRB1*1117, DRB1*1118, DRB1*1119, DRB1*1120, DRB1*1121, DRB1*1122, DRB1*1123, DRB1*1124, DRB1*1125, DRB1*1126, DRB1*112701, DRB1*112702, DRB1*1128, DRB1*1129, DRB1*1130, DRB1*1131, DRB1*1132, DRB1*1133, DRB1*1134, DRB1*1135, DRB1*1136, DRB1*1137, DRB1*1138, DRB1*1139, DRB1*1140, DRB1*1141, DRB1*1142, DRB1*1143, DRB1*1144, DRB1*1145, DRB1*1146, DRB1*1147, DRB1*1148, DRB1*1149, DRB1*1150, DRB1*1151, DRB1*1152, DRB1*1153, DRB1*1154, DRB1*120101, DRB1*120102, DRB1*120201, DRB1*120202, DRB1*120302, DRB1*1204, DRB1*1205, DRB1*1206, DRB1*1207, DRB1*1208, DRB1*1209, DRB1*1210, DRB1*130101, DRB1*130102, DRB1*130103, DRB1*130201, DRB1*130202, DRB1*130301, DRB1*130302, DRB1*1304, DRB1*1305, DRB1*1306, DRB1*130701, DRB1*130702, DRB1*1308, DRB1*1309, DRB1*1310, DRB1*1311, DRB1*1312, DRB1*1313, DRB1*131401, DRB1*131402, DRB1*1315, DRB1*1316, DRB1*1317, DRB1*1318, DRB1*1319, DRB1*1320, DRB1*1321, DRB1*1322, DRB1*1323, DRB1*1324, DRB1*1325, DRB1*1326, DRB1*1327, DRB1*1328, DRB1*1329, DRB1*1330, DRB1*1331, DRB1*1332, DRB1*1333, DRB1*1334, DRB1*1335, DRB1*1336, DRB1*1337, DRB1*1338, DRB1*1339, DRB1*1340, DRB1*1341, DRB1*1342, DRB1*1343, DRB1*1344, DRB1*1345, DRB1*1346, DRB1*1347, DRB1*1348, DRB1*1349, DRB1*1350, DRB1*1351, DRB1*1352, DRB1*1353, DRB1*1354, DRB1*1355, DRB1*1356, DRB1*1357, DRB1*1358, DRB1*1359, DRB1*1360, DRB1*1361, DRB1*1362, DRB1*1363, DRB1*1364, DRB1*1365, DRB1*140101, DRB1*140102, DRB1*1402, DRB1*140301, DRB1*140302, DRB1*1404, DRB1*140501, DRB1*140502, DRB1*1406, DRB1*140701, DRB1*140702, DRB1*1408, DRB1*1409, DRB1*1410, DRB1*1411, DRB1*1412, DRB1*1413, DRB1*1414, DRB1*1415, DRB1*1416, DRB1*1417, DRB1*1418, DRB1*1419, DRB1*1420, DRB1*1421, DRB1*1422, DRB1*1423, DRB1*1424, DRB1*1425, DRB1*1426, DRB1*1427, DRB1*1428, DRB1*1429, DRB1*1430, DRB1*1431, DRB1*1432, DRB1*1433, DRB1*1434, DRB1*1435, DRB1*1436, DRB1*1437, DRB1*1438, DRB1*1439, DRB1*1440, DRB1*1441, DRB1*1442, DRB1*1443, DRB1*1444, DRB1*1445, DRB1*1446, DRB1*1447, DRB1*1448, DRB1*150101, DRB1*150102, DRB1*150103, DRB1*150104, DRB1*150105, DRB1*150201, DRB1*150202, DRB1*150203, DRB1*1503, DRB1*1504, DRB1*1505, DRB1*1506, DRB1*1507, DRB1*1508, DRB1*1509, DRB1*1510, DRB1*1511, DRB1*1512, DRB1*1513, DRB1*1514, DRB1*1515, DRB1*1516, DRB1*160101, DRB1*160102, DRB1*160201, DRB1*160202, DRB1*1603, DRB1*1604, DRB1*160501, DRB1*160502, DRB1*1607, DRB1*1608.

HLA-DRB2-9

DRB2*0101, DRB3*010101, DRB3*01010201, DRB3*01010202, DRB3*010103, DRB3*010104, DRB3*0102, DRB3*0103, DRB3*0104, DRB3*0105, DRB3*0106, DRB3*0107, DRB3*0108, DRB3*0109, DRB3*0110, DRB3*0111, DRB3*0201, DRB3*020201, DRB3*020202, DRB3*020203, DRB3*020204, DRB3*0203, DRB3*0204, DRB3*0205, DRB3*0206, DRB3*0207, DRB3*0208, DRB3*0209, DRB3*0210, DRB3*0211, DRB3*0212, DRB3*0213, DRB3*0214, DRB3*0215, DRB3*0216, DRB3*0217, DRB3*0218, DRB3*0219, DRB3*030101, DRB3*030102, DRB3*0302, DRB3*0303, DRB4*01010101, DRB4*0102, DRB4*01030101, DRB4*01030102N, DRB4*010302, DRB4*010303, DRB4*010304, DRB4*0104, DRB4*0105, DRB4*0106, DRB4*0107, DRB4*0201N, DRB4*0301N, DRB5*010101, DRB5*010102, DRB5*0102, DRB5*0103, DRB5*0104, DRB5*0105, DRB5*0106, DRB5*0107, DRB5*0108N, DRB5*0109, DRB5*0110N, DRB5*0111, DRB5*0112, DRB5*0113, DRB5*0202, DRB5*0203, DRB5*0204, DRB5*0205, DRB6*0101, DRB6*0201, DRB6*0202, DRB7*010101, DRB7*010102, DRB8*0101, DRB9*0101.

HLA-DQA1

DQA1*010101, DQA1*010102, DQA1*010201, DQA1*010202, DQA1*0103, DQA1*010401, DQA1*010402, DQA1*0105, DQA1*0106, DQA1*0107, DQA1*0201, DQA1*030101, DQA1*0302, DQA1*0303, DQA1*040101, DQA1*040102, DQA1*0402, DQA1*0403N, DQA1*0404, DQA1*050101,

DQA1*050102, DQA1*0502, DQA1*0503, DQA1*0504, DQA1*0505, DQA1*060101, DQA1*060102, DQA1*0602.

HLA-DQB1

DQB1*020101, DQB1*020102, DQB1*0202, DQB1*0203, DQB1*030101, DQB1*030102, DQB1*030201, DQB1*030202, DQB1*030302, DQB1*030303, DQB1*0304, DQB1*030501, DQB1*030502, DQB1*030503, DQB1*0306, DQB1*0307, DQB1*0308, DQB1*0309, DQB1*0310, DQB1*0311, DQB1*0312, DQB1*0313, DQB1*0401, DQB1*0402, DQB1*050101, DQB1*050102, DQB1*050201, DQB1*050202, DQB1*050301, DQB1*050302, DQB1*0504, DQB1*060101, DQB1*060102, DQB1*060103, DQB1*0602, DQB1*0603, DQB1*060401, DQB1*060402, DQB1*060501, DQB1*060502, DQB1*0606, DQB1*0607, DQB1*0608, DQB1*0609, DQB1*0610, DQB1*061101, DQB1*061102, DQB1*0612, DQB1*0613, DQB1*0614, DQB1*0615, DQB1*0616, DQB1*0617, DQB1*0618, DQB1*0619, DQB1*0620, DQB1*0621, DQB1*0622, DQB1*0623.

HLA-DPA1

DPA1*010301, DPA1*010302, DPA1*010303, DPA1*0104, DPA1*0105, DPA1*0106, DPA1*0107, DPA1*0108, DPA1*020101, DPA1*020102, DPA1*020103, DPA1*020104, DPA1*020105, DPA1*020106, DPA1*020201, DPA1*020202, DPA1*020203, DPA1*0203, DPA1*0301, DPA1*0302, DPA1*0303, DPA1*0401.

HLA-DPB1

DPB1*010101, DPB1*010102, DPB1*010103, DPB1*0102, DPB1*020102, DPB1*020103, DPB1*020104, DPB1*020105, DPB1*020106, DPB1*0202, DPB1*0203, DPB1*030101, DPB1*030102, DPB1*0302, DPB1*040101, DPB1*040102, DPB1*0402, DPB1*0501, DPB1*0601, DPB1*0801, DPB1*0901, DPB1*1001, DPB1*110101, DPB1*110102, DPB1*1301, DPB1*1401, DPB1*1501, DPB1*1601, DPB1*1701, DPB1*1801, DPB1*1901, DPB1*200101, DPB1*200102, DPB1*2101, DPB1*2201, DPB1*2301, DPB1*2401, DPB1*2501, DPB1*260101, DPB1*260102, DPB1*2701, DPB1*2801, DPB1*2901, DPB1*3001, DPB1*3101, DPB1*3201, DPB1*3301, DPB1*3401, DPB1*3501, DPB1*3601, DPB1*3701, DPB1*3801, DPB1*3901, DPB1*4001, DPB1*4101, DPB1*4401, DPB1*4501, DPB1*4601, DPB1*4701, DPB1*4801, DPB1*4901, DPB1*5001, DPB1*5101, DPB1*5201, DPB1*5301, DPB1*5401, DPB1*5501, DPB1*5601, DPB1*5701, DPB1*5801, DPB1*5901, DPB1*6001, DPB1*6101N, DPB1*6201, DPB1*6301, DPB1*6401N, DPB1*6501, DPB1*6601, DPB1*6701, DPB1*6801, DPB1*6901, DPB1*7001, DPB1*7101, DPB1*7201, DPB1*7301, DPB1*7401, DPB1*7501, DPB1*7601, DPB1*7701, DPB1*7801, DPB1*7901, DPB1*8001, DPB1*8101, DPB1*8201, DPB1*8301, DPB1*8401, DPB1*8501, DPB1*8601, DPB1*8701, DPB1*8801, DPB1*8901, DPB1*9001, DPB1*9101, DPB1*9201, DPB1*9301, DPB1*9401, DPB1*9501, DPB1*9601, DPB1*9701, DPB1*9801, DPB1*9901.

HLA-DMA

DMA*0101, DMA*0102, DMA*0103, DMA*0104.

HLA-DMB

DMB*0101, DMB*0102, DMB*0103, DMB*0104, DMB*0105, DMB*0106.

HLA-DOA

DOA*010101, DOA*01010201, DOA*01010202, DOA*01010203, DOA*010103, DOA*01010401, DOA*01010402, DOA*010105.

HLA-DOB

DOB*01010101, DOB*01010102, DOB*010102, DOB*010201, DOB*010202, DOB*0103, DOB*01040101, DOB*01040102.

MHC Class I

H-2 Db, H-2Dd, H-2Dk, H-2Dq, H-2 Kb, H-2 Kd, H-2Kk, H-2Ld, H-2M3, H-2Ad, H-2Ag7, H-2Ak, H2-Ab, H-2Ed, H-2Ek, H-2Bxk, H-2F, H-21, H-2P, H-2R, H-2S, H-2Sxd, H-2T4, H-2U.

MHC Class II

I-Ab, I-Ad, I-Ag7, I-Ak, I-Ap, I-Aq, I—Ar, I—As, I-Au, I-Av, I-Ea, I-Eb, I-Ed, I-Ek, I—Es, I—Eu, H-2Q, H-2Qa-2, H-2Qa-2a, Qa-1a, Qa-1b.

The invention is not limited to such MHC and HLA molecules, and can be adapted to newly discovered such molecules, if desired, simply by establishing the reactivity of substances such as peptides with the molecules. This can be readily achieved using known techniques that are standard in the field. Particularly preferred HLA alleles for use with the present invention include the following:

| HLA Class I | | |
|---|---|---|
| HLA A | HLA B | HLA Cw |
| A*6802 | B*5801 | Cw*1701 |
| A*6801 | B*5701 | Cw*1601 |
| A*6601 | B*5501 | Cw*1502 |
| A*3303 | B*5201 | Cw*1402 |
| A*3301 | B*5101 | Cw*1203 |
| A*3201 | B*5001 | Cw*0802 |
| A*310102 | B*4901 | Cw*0801 |
| A*3002 | B*4501 | Cw*0704 |
| A*3001 | B*4403 | Cw*0703 |
| A*2902 | B*4402 | Cw*0702 |
| A*2608 | B*4101 | Cw*0701 |
| A*2601 | B*4002 | Cw*0602 |
| A*2501 | B*4001 | Cw*0501 |
| A*2402 | B*3901 | Cw*0401 |
| A*2301 | B*3801 | Cw*0304 |
| A*1101 | B*3701 | Cw*0303 |
| A*0302 | B*3503 | Cw*0202 |
| A*0301 | B*3501 | Cw*0102 |
| A*0205 | B*2705 | |
| A*0201 | B*1801 | |
| A*0101 | B*1501 | |
| | B*1402 | |
| | B*1401 | |
| | B*1302 | |
| | B*0801 | |
| | B*0705 | |
| | B*0702 | |

| HLA Class II | | | |
|---|---|---|---|
| HLA DPB | HLA DQA | HLA DQB | HLA DRB |
| DPB1*1701 | DQA1*0505 | DQB1*0604 | DRB1*1601 |
| DPB1*1301 | DQA1*0501 | DQB1*0603 | DRB1*1501 |
| DPB1*1001 | DQA1*0401 | DQB1*0602 | DRB1*1401 |
| DPB1*0601 | DQA1*0303 | DQB1*0503 | DRB1*1302 |
| DPB1*0501 | DQA1*0302 | DQB1*0502 | DRB1*1301 |
| DPB1*0402 | DQA1*0301 | DQB1*0501 | DRB1*1201 |
| DPB1*0401 | DQA1*0201 | DQB1*0402 | DRB1*1104 |
| DPB1*0301 | DQA1*0104 | DQB1*0303 | DRB1*1101 |
| DPB1*0201 | DQA1*0103 | DQB1*0302 | DRB1*0801 |
| DPB1*0101 | DQA1*0102 | DQB1*0301 | DRB1*0701 |
| | DQA1*0101 | DQB1*0202 | DRB1*0404 |
| | | DQB1*0201 | DRB1*0401 |

-continued

| HLA Class II | | | |
|---|---|---|---|
| HLA DPB | HLA DQA | HLA DQB | HLA DRB |
| | | | DRB1*0301 |
| | | | DRB1*0103 |
| | | | DRB1*0102 |
| | | | DRB1*0101 |

The most preferred alleles according to the invention are the following:

HLA-A*0201, HLA-A*0206, HLA-A*0301, HLA-A*1101, HLA-A*2402, HLA-A*3401, HLA-B*0702, HLA-B*0801, HLA-B*1301, HLA-B*27, HLA-B*4002, HLA-B*5101, HLA-Cw*03, HLA-cW*07

HLA-DRB1*0301, HLA-DRB1*0401, HLA-DRB1*0701, HLA-DRB1*1501, HLA-DRB1*1104, HLA-DRB1*1101, HLA-DRB4*0101

HLA-DQA1*01, HLA-DQA1*02, HLA-DQA1*05

HLA-DQB1*03, HLA-DQB1*04, HLA-DQB1*05, HLA-DQB1*06

HLA-DPA1*01, HLA-DPA1*02

HLA-DPB1*02, HLA-DPB1*04

The invention will now be described by way of example only, with reference to the following specific embodiments.

EXAMPLES

Experiment 1

Reactivity of Polypeptides Against Influenza Antigens

The purpose of the study was to demonstrate the reactivity of the above-described influenza polypeptides and their ability to induce a specific Th1-type cytokine response against naturally processed and presented influenza proteins in the context of human HLA (HLA A*0201).

As background to the experiments, it is useful to understand that Th1 and Th2 responses are defined by the pattern of cytokines produced by the T helper cells involved in them. That, however, does not mean that the remaining lymphocytes (T and B cells) involved in those specific responses do not also produce cytokines that help drive the characteristic pattern of response in which they are involved. In this way, a Th1-like response is characterised by the production of IFN-γ and IL-2, leading to the stimulation of a CD8+ CTL response and an associated (in mice) IgG2a antibody response. The IFN-γ response can be produced both by the CD4+ T helper 1 cells as well as by the CD8+ T cells that also form part of it. In this case the IFN-γ component of the response produced by the CD8+ T cells was investigated. That was because the experiment was primarily investigating CD8+ T cell epitopes and it was desirable to prove that the response seen was caused by those cells. Since CD8+ T cells react to epitopes only on MHC class I molecules, human cells that share with the transgenic mouse only one MHC class I molecule (i.e. HLA-A*0201) were used. A Th2-like response is characterised by the production of IL-4 and IL-10, leading to the stimulation of an IgGE, IgG1 and (in mice) IgG2b antibody response. Both responses are antagonistic with IFN-γ and IL-10 downregulating the production of each other. All the experiments described below were carried out in duplicate.

Materials and Methods
Peptides and Recombinant Proteins

All the polypeptides used in this study (i.e. P1: MIA amino acid (aa) 36 to 75 (SEQ ID 1); P2: M1B aa 124 to 158 (SEQ ID 2); P3: NPA aa 255 to 275 (SEQ ID 3); P4: NPB aa 306 to 326 (SEQ ID 4); P5: PB1 aa 395 to 428 (SEQ ID 5); P6: M2 aa 32 to 55 (SEQ ID 6) and NRP: a control non-relevant polypeptide) were synthesised by Fmoc chemistry and resuspended in 10% DMSO in PBS.

Cell Lines and Viruses

The T1 and JURKAT cell lines are human lymphoblastoid lines derived from HLA-A*0201 bearing and non-bearing individuals respectively. T1 was maintained in IMDM medium (Invitrogen) whilst JURKAT was maintained in RPMI-1640 medium (Sigma) containing 10 mM HEPES and 1 mM sodium pyruvate. Both media were supplemented with 50 IU/50 mg/ml of penicillin/streptomycin (Sigma) and, as complete medium, 10% FCS. Cell cultures were maintained at 37° C. in a humidified atmosphere of 5% CO2.

Primary splenocytes were maintained in IMDM medium (Invitrogen) supplemented with 0.02 mM β-mercaptoethanol (Sigma), 50 IU/50 mg/ml of penicillin/streptomycin (Sigma) and 10% FCS (Sigma) at 37° C. in a humidified atmosphere of 5% CO2.

Influenza A strains New_Calcdonia/20/99, NYMC/X-147 and Influenza B strain Johannesburg/5/99 were obtained from NIBSC as lyophilised stocks and used for the infection of syngeneic (T1) and allogeneic (JURKAT) human cell lines.

Preparation of Target Cells for Cytokine Analysis

Cell cultures in exponential phase were harvested by centrifugation (250 g, 5 min) and resuspended at a density of $10^6$ cells/ml in serum-free medium. Aliquots of the cell suspensions were transfected with a range of polypeptide antigens at a concentration of 5 μg per $10^6$ cells using Lipofectin (Invitrogen) according to the manufacturers instructions and incubated in complete medium for 8-10 hours before Mytomicin C (MMC) treatment. Alternatively, aliquots of the cell suspensions were infected with a range of live Influenza virus (MOI of 5-10) for one hour, washed twice in serum free medium and incubated in complete medium for 24 hours before MMC treatment.

For MMC treatment, cells were harvested by centrifugation (250 g, 5 min) and resuspended in serum-free IMDM medium containing 50 μg/ml of Mitomycin C (Sigma). After 45 min incubation at 37° C., the cell suspensions were washed four times in serum-free IMDM medium (250 g, 5 min) and finally resuspended in complete IMDM medium.

Immunizations

Seven to ten week old C57BL/6-Tg(HLA-A2.1)1Enge/J mice (HLA-A*0201 transgenic on a C57/BL6 background, Jackson Labs) were immunised subcutaneously with a 200 μl dose of the antigen preparation per mouse. In the test group, each dose of the antigen preparation contained 60 nmol of an equimolar mixture of all six peptides (10 nmol each) prepared in IFA (Sigma) according to the manufacturers instructions (FLU-v preparation). In the control group, each dose of the antigen preparation contained an equivalent dose of the non-relevant polypeptide prepared in IFA (Sigma) according to the manufacturers instructions (NRP preparation).

On day 14 post-immunisation, all animals received a booster immunisation using the same doses and route of delivery as used originally. Finally, on day 21 or 22, all animals were culled and their spleens collected.

The immunisation protocol can be represented schematically as shown in FIG. 4.

Statistical Analysis

Statistically significant differences in the IFN-γ response to different antigens between FLU-v and NRP vaccinated animals were established through non-parametric Mann-Whitney analysis of the samples. Differences were considered statistically significant if the p value was below 0.05.

Cytokine ELISA

Mouse spleens belonging to the same experimental group were pooled, gently pressed through cell strainers and red blood cells removed by treatment with red cell lysis buffer (nine parts 0.16 M $NH_4Cl$ and one part of 0.17 M Tris, pH 7.2). Splenocyte suspensions from each experimental group were plated in 24-well plates at a density of $4 \times 10^6$ cells/well containing a range of polypeptide antigens (5 μg/ml) or, alternatively, MMC treated cell lines (splenocyte to cell (S:C) ratio 10:1) either transfected with polypeptide antigens or infected with different live Influenza virus as described above.

After 4 days incubation at 37° C., the supernatant was collected and analyzed for IFN-γ and IL-4 by a sandwich cytokine ELISA according to the manufacturers protocol (Pharmingen). The lower detection limits for the assay were 9.77 μg/ml for IL-4 and 39.06 μg/ml for IFN-γ.

Results

Each individual polypeptide peptide described in this patent application (including P1, P2, P3, P4, P5 and P6 tested in this example) has been defined as containing T cell epitopes reactive in multiple human HLA molecules, amongst them HLA-A*0201. The aim of this study is, therefore, to assess the ability of the above described polypeptides to induce a specific multi-antigen Th1-like immune (i.e. IFN-γ mediated) response as well as the ability of this response to specifically react to naturally processed and presented Influenza antigens from several non-related strains pathogenic to humans in the context of infected human HLA A*0201 bearing cells.

Reactivity of Peptide 1

Upon internal processing of the polypeptide by the antigen presenting cells (APCs) of the transgenic mice, the contained CD8+ T cell specific epitopes would be presented in the surface of the APC in association with the HLA-A*0201 molecules where they would proceed to activate naive CD8+ T cells and induce a P1 specific Th1-like immune response.

To confirm this, HLA-A*0201 bearing (T1) and non-bearing (JURKAT) human cell lines were intracellularly loaded with P1 by means of a lipid vehicle (Lipofectin, INVITROGEN). Splenocytes from animals immunised with the influenza polypeptide preparation (FLU-v) were found to produce significantly increased levels of IFN-γ compared to splenocytes from NRP immunised animals when co-cultured with MMC treated HLA-A*0201 bearing human cells (T1) transfected with P1, but not when co-cultured with non-HLA-A*0201 bearing human cells (JURKAT) treated in the same way (see FIG. 1A, the data for which is presented in Table 1 below).

TABLE 1

| Δ IFN-γ to Lys (pg/ml) | FLU-v | NRP |
| --- | --- | --- |
| Con A | 2395.6 ± 45.9 | 2257.5 ± 29.8 |
| FLU Peptide 1 (sol) | 119.3 ± 7.1 | <39 |
| T1-FLU pep 1 (pro) | 228.4 ± 16.6 | 55.8 ± 7 |
| Ju-FLU pep 1 (pro) | <39 | 51.2 ± 1.6 |

Note:
"Lys" means the negative control background upon which all values are calculated.
"Sol" means soluble peptide presented to the primary splenocyte population.
"Pro" means that the peptide is being presented complexed with the cell's HLA molecules following internal processing and loading of the resulting epitopes on to the MHC molecules.
Values represent average ± standard error of the Δ IFN-γ to Lys (pg/ml).

Figure 5:
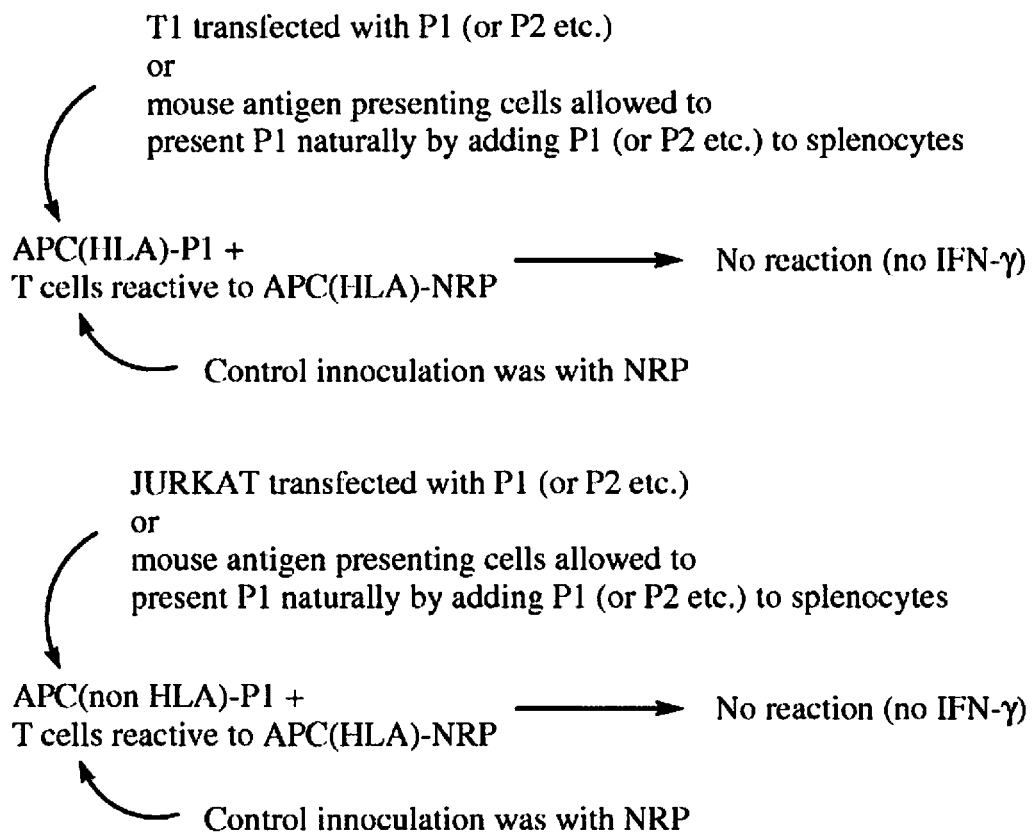
FIG. 5 shows Scheme 2—control test for T1 and JURKAT.

The experiment can be represented schematically as shown in FIG. 5 and FIG. 6.

As the transgenic mice used in these experiments do not bear any other human HLA and the ability of its CD8+ T cells to specifically recognise P1-derived epitopes in the context of other human HLAs which they have never encountered is low, these results clearly show that the observed IFN-γ response is specifically caused by primed CD8+ T cells recognising P1-derived epitopes in association with HLA-A*0201 molecules.

It is also important to note that no IL-4 response was detected against the P1 transfected cells in either FLU-v or NRP immunised animals (data not shown). Since IL-4 production is antagonistic to IFN-γ production and hence to the creation of antigen specific CD8+ T cell responses, the lack of IL-4 production in both groups clearly shows that immunisation with FLU-v induces a specific Th1-like response to the P1 component of the preparation.

A significantly increased level in IFN-γ production is also observed in the FLU-v compared to the NRP immunised groups when soluble P1 antigen is simply added to the splenocyte culture (in the absence of T1 or JURKAT cells). However, the overall level of this IFN-γ response is lower than that observed when the antigen was presented via the HLA-A*0201 bearing T1 cells. The explanation for this observation is that P1 was defined on the basis of containing epitopes that are primarily reactive in the context of human and not mouse HLAs. The transgenic mice here used contain a full complement of mouse MHC molecules in addition to the HLA-A*0201 molecules, hence the soluble P1 captured by the APC population present in the primary splenocyte cultures can also be processed into the mouse MHC Class I and II pathways (Peachman K K, Rao M, Alving C R, Palmer D R, Sun W, Rothwell S W. "Human dendritic cells and macrophages exhibit different intracellular processing pathways for soluble and liposome-encapsulated antigens." Immunobiology. 2005; 210(5):321-33), which mediate H-2D restricted CD8+ and CD4+ T cell responses respectively. As a result, if P1 contained multiple murine epitopes, it would be expected that the IFN-γ response to soluble P1 would be equal or greater to that observed for the case of human cell mediated presentation as a much larger pool of CD4+ and CD8+ T cells would be able to react to the stimulus. As this is not observed and the level of an immune response in vitro is primarily determined by the availability of antigen, it clearly follows that the P1-specific CD8+ T lymphocytes detected in the T1 co-culture experiments would simply be unable to respond at the same level due to the reduced amount of antigen being presented to them in the correct HLA-A*0201 context.

Reactivity of Peptide 2

Splenocytes from animals immunised with the FLU-v have been found to produce significantly increased levels of IFN-γ compared to splenocytes from NRP immunised animals when co-cultured with MMC treated HLA-A*0201 bearing human cells (T1) transfected with P2, but not when co-cultured with non-HLA-A*0201 bearing human cells (JURKAT) treated in the same way (see FIG. 1B, the data for which is set out in Table 2 below). As it was the case for P1, these results clearly show that the observed IFN-γ response is specifically caused by CD8+ T cells recognising P2-derived epitopes in association with HLA-A*0201 molecules. Similarly, as IL-4 production is antagonistic to IFN-γ production and hence to the development of CD8+ T cells, the lack of an IL-4 response against P2 transfected cells in either FLU-v or NRP immunised animals (data not shown) clearly shows that FLU-v immunisation induces a P2-specific Th1-like response.

TABLE 2

| Δ IFN-γ to Lys (pg/ml) | FLU-v | NRP |
| --- | --- | --- |
| Con A | 2395.6 ± 45.9 | 2257.5 ± 29.8 |
| FLU Peptide 1 (sol) | 976.9 ± 24.1 | 468.4 ± 14.7 |
| T1-FLU pep 1 (pro) | 372.9 ± 6.4 | 154.5 ± 10.7 |
| Ju-FLU pep 1 (pro) | <39 | <39 |

Note:
"Lys" means the negative control background upon which all values are calculated.
"Sol" means soluble peptide presented to the primary splenocyte population.
"Pro" means that the peptide is being presented complexed with the cell's HLA molecules following internal processing and loading of the resulting epitopes on to the MHC molecules.
Values represent average ± standard error of the Δ IFN-γ to Lys (pg/ml).

A significantly increased IFN-γ production was also observed in the FLU-v compared to NRP immunised groups when P2 was simply added to the splenocyte culture. In contrast to P1, however, the overall level of the IFN-γ response was greater to the soluble antigen than to that presented by the HLA-A*0201 bearing cells. This observation would indicate that P2 harbours not only strong HLA-A*0201 epitopes but also strong mouse (H-2D) epitopes.

Reactivity of Peptides 3, 4 and 5

As was the case for P2, significantly increased IFN-γ production can be observed between FLU-v and NRP immunised groups when P3, P4 and P5 are simply added to the culture as well as when they are presented via HLA-matched transfected human cells lines (T1), but not when they are presented via HLA-mismatched (JURKAT) human cell lines (see FIGS. 1C, 1D and 1E, the data for which is set out in Tables 3-5 below). In all three cases, the increment in IFN-γ production is greater when splenocytes are co-cultured with transfected human cells rather than when soluble antigen is simply added to the medium. These results, due to the same arguments developed for the case of P2, indicate that P3, P4 and P5 contain a number of strong mouse T cell epitopes in addition to the human ones.

TABLE 3

| Δ IFN-γ to Lys (pg/ml) | FLU-v | NRP |
| --- | --- | --- |
| Con A | 2395.6 ± 45.9 | 2257.5 ± 29.8 |
| FLU Peptide 1 (sol) | 1734.1 ± 57.2 | 268.0 ± 11.0 |
| T1-FLU pep 1 (pro) | 587.5 ± 14.9 | <39 |
| Ju-FLU pep 1 (pro) | 148.5 ± 3.0 | 146.5 ± 17.6 |

Note:
"Lys" means the negative control background upon which all values are calculated.
"Sol" means soluble peptide presented to the primary splenocyte population.
"Pro" means that the peptide is being presented complexed with the cell's HLA molecules following internal processing and loading of the resulting epitopes on to the MHC molecules.
Values represent average ± standard error of the Δ IFN-γ to Lys (pg/ml).

TABLE 4

| Δ IFN-γ to Lys (pg/ml) | FLU-v | NRP |
| --- | --- | --- |
| Con A | 2395.6 ± 45.9 | 2257.5 ± 29.8 |
| FLU Peptide 1 (sol) | 1170.5 ± 27.8 | 693.8 ± 5.6 |

TABLE 4-continued

| Δ IFN-γ to Lys (pg/ml) | FLU-v | NRP |
| --- | --- | --- |
| T1-FLU pep 1 (pro) | 229.9 ± 35.2 | 84.6 ± 11.6 |
| Ju-FLU pep 1 (pro) | <39 | <39 |

Note:
"Lys" means the negative control background upon which all values are calculated.
"Sol" means soluble peptide presented to the primary splenocyte population.
"Pro" means that the peptide is being presented complexed with the cell's HLA molecules following internal processing and loading of the resulting epitopes on to the MHC molecules.
Values represent average ± standard error of the Δ IFN-γ to Lys (pg/ml).

TABLE 5

| Δ IFN-γ to Lys (pg/ml) | FLU-v | NRP |
| --- | --- | --- |
| Con A | 2395.6 ± 45.9 | 2257.5 ± 29.8 |
| FLU Peptide 1 (sol) | 1067.75 ± 7.3 | 220.5 ± 6.6 |
| T1-FLU pep 1 (pro) | 405.6 ± 11.8 | <39 |
| Ju-FLU pep 1 (pro) | <39 | <39 |

Note:
"Lys" means the negative control background upon which all values are calculated.
"Sol" means soluble peptide presented to the primary splenocyte population.
"Pro" means that the peptide is being presented complexed with the cell's HLA molecules following internal processing and loading of the resulting epitopes on to the MHC molecules.
Values represent average ± standard error of the Δ IFN-γ to Lys (pg/ml).

Finally, as all three peptides fail to induce the production of IL-4 (data not shown), it is clear that the immune response induced by vaccination with the FLU-v preparation induces a Th1-like response to each of these three polypeptides.

Reactivity of Peptide 6

As was the case for P1, significantly increased IFN-γ production can be observed between FLU-v and NRP immunised groups when P6 is simply added to the culture as well as when it is presented via HLA-matched transfected human cells lines (T1), but not when it is presented via HLA-mismatched (JURKAT) human cell lines (see FIG. 1F, the data for which is set out in Table 6 below). Again as for P1, the greater response is observed to the soluble antigen, indicating that P6 does not contain strong H-2D epitopes. As the causes for these observations have already been explained for the case of P1 they shall not be developed further here and one shall refer to that earlier section.

TABLE 6

| Δ IFN-γ to Lys (pg/ml) | FLU-v | NRP |
| --- | --- | --- |
| Con A | 2395.6 ± 45.9 | 2257.5 ± 29.8 |
| FLU Peptide 1 (sol) | 496.2 ± 11.8 | 105.5 ± 7.0 |
| T1-FLU pep 1 (pro) | 1210.5 ± 11.5 | 817.6 ± 8.9 |
| Ju-FLU pep 1 (pro) | <39 | <39 |

Note:
"Lys" means the negative control background upon which all values are calculated.
"Sol" means soluble peptide presented to the primary splenocyte population.
"Pro" means that the peptide is being presented complexed with the cell's HLA molecules following internal processing and loading of the resulting epitopes on to the MHC molecules.
Values represent average ± standard error of the Δ IFN-γ to Lys (pg/ml).

The failure of stimulation with P6 to induce any IL-4 production (data not shown), clearly show that the immune response induced by FLU-v vaccination induces a Th1-like response to P6.

Reactivity of FLU-v to Non-Related Influenza Strains

The experiments described up to this point clearly show that immunisation with FLU-v induces a specific CD8$^+$ T cell IFN-γ response against each of the six constituent polypeptides. However, as these polypeptides were defined as containing reactive CD8$^+$ T cell epitopes subject to a low level of sequence variability within the influenza virus population analyzed, it was also desirable to establish whether FLU-v vaccinated mice were capable of recognising, and hence inducing a specific Th1-like immune response, T cell epitopes naturally processed and presented following infection with different non-related strains of influenza. Such analysis provides a clear indication of the potential efficacy of the FLU-v polypeptide mixture as an influenza vaccine which, by virtue of targeting T cell epitopes of low sequence variability across the human and animal influenza population, would provide protection against all current strains as well as those which may arise in the future from spontaneous recombination between highly pathogenic animal strains with current human strains.

For this analysis, primary splenocyte cultures of transgenic animals immunised with FLU-v or NRP were co-cultured with several influenza infected HLA-A*0201 bearing (T1) and non-bearing (JURKAT) human cells. The three influenza strains used for infection (A/New_Calcdonia/20/99, A/NYMC/X-147 and B/Johannesburg/5/99) are all pathogenic to humans and were obtained from the Influenza WHO repository, based at NIBSC (UK). As an antigen specific positive control an equimolar soluble preparation of the six polypeptides added to the primary splenocyte preparation was used.

Splenocytes from FLU-v vaccinated animals produced a significantly higher level of IFN-γ compared to those of NRP vaccinated animals when co-cultured with MMC treated influenza infected HLA-A*0201 bearing human cells (T1) transfected, but not when co-cultured with non-HLA-A*0201 bearing human cells (JURKAT) treated in the same way (see FIG. 2, the data for which is set out in Table 7 below). No IL-4 response was detected in any of the vaccinated mice against either the soluble polypeptide antigen or the Influenza infected cells (data not shown). These results clearly show that the observed IFN-γ response is specifically caused by primed $CD8^+$ T cells recognising epitopes contained in the FLU-v preparation and which are also naturally processed and presented in association with HLA-A*0201 molecules in influenza infected human cells.

TABLE 7

| Δ IFN-γ to Lys (pg/ml) | FLU-v | NRP |
|---|---|---|
| Con A | 2395.6 ± 45.9 | 2257.5 ± 29.8 |
| FLU peptide mix (sol) | 1440.2 ± 44.9 | 678.3 ± 29.2 |
| T1-Flu A/NC/20/99 | 2146.4 ± 23.7 | 1282.1 ± 4.8 |
| Ju-Flu A/NC/20/99 | 1246.9 ± 48.8 | 1206.4 ± 10.9 |
| T1-Flu A/NYMC/X147 | 1949.4 ± 37.9 | 1101 ± 5.9 |
| Ju-Flu A/NYMC/X147 | 1342.3 ± 14.5 | 1248.6 ± 8.3 |
| T1-Flu B/Johannesburg/5/99 | 1769.0 ± 33.6 | 1196.0 ± 16.2 |
| Ju-Flu B/Johannesburg/5/99 | 257.6 ± 3.0 | 257.0 ± 8.3 |

Note:
"Lys" means the negative control background upon which all values are calculated.
"Sol" means soluble peptide presented to the primary splenocyte population.
"Pro" means that the peptide is being presented complexed with the cell's HLA molecules following internal processing and loading of the resulting epitopes on to the MHC molecules.
T1 is the HLA-A*0201-bearing human cell line.
"Ju" refers to JURKAT which is the HLA-A*0201 non-bearing human cell line.
A/NC/20/99 (i.e. A/New_Caledonia/20/99), A/NYMC/X-147 and B/Johannesburg/5/99 are, respectively, the two influenza A and one influenza B strains used for infection of the human cell lines.
Values represent average ± standard error of the Δ IFN-γ to Lys (pg/ml).

Interestingly, the background production of IFN-γ for all influenza infected groups was greater than observed when similar analysis were carried out using purified polypeptide antigen. This observation, however, most likely reflects the inability of MMC treatment to fully inactivate the virus present in the cell preparation. This, in turn, would result in viable Influenza virus infecting susceptible mouse cells in the primary splenocyte cultures, thus leading to a primary response in vitro. This interpretation is sustained by the observation that most influenza virus strains used induced the same level of background IFN-γ response independently of the human cell line infected and the vaccinated group considered. The only exception to this rule is the much reduced background IFN-γ production observed in JURKAT cells infected with B/Johannesburg/5/99. However, as even in this case IFN-γ production for both FLU-v and NRP vaccinated animals is equivalent, it would appear that the observed difference is caused more by the reduced susceptibility of JURKAT cells to infection by Influenza B/Johannesburg/5/99, than by any cause intrinsically associated to the different vaccination regimes. Whatever the case, this observation, does not detract from the clear fact that vaccination with FLU-v leads to the specific recognition of naturally processed influenza epitopes presented in association with HLA-A*0201 molecules following infection of human cells with several non-related strains of infectious influenza virus. Therefore, FLU-v constitutes an effective candidate vaccine preparation for protection against multiple influenza strains, thus obviating the need for the current yearly re-vaccination protocols.

Experiment 2

Protective Effect of Polypeptides in Mice

The purpose of this study was to demonstrate that low dose immunisation with the identified Influenza conserved T cell polyepitope peptides (FLU-v) induces protection, mediated by $CD8^+$ T cells, against lethal challenge with the influenza virus.

Materials and Methods

Peptides, Antisera and Virus:

The candidate vaccine preparation (FLU-v) tested in this study is composed of several peptides (i.e. P1: MIA amino acid (aa) 36 to 75 (SEQ ID 1); P2: M1B aa 124 to 158 (SEQ ID 2); P3: NPA aa 255 to 275 (SEQ ID 3); P4: NPB aa 306 to 326 (SEQ ID 4); P5: PB1 aa 395 to 428 (SEQ ID 5); P6: M2 aa 32 to 55 (SEQ ID 6)) which were all synthesised by Fmoc chemistry and resuspended in DMSO in PBS (the concentration of DMSO in the final preparation was less than 5%). Lysozyme (Sigma) denatured by boiling was used as the control non relevant preparation (NRP-v).

Purified rat anti-mouse CD8 IgG2a (clone YTS169.4) was obtained from AbD Serotec (UK) whilst the infectious virus Influenza A/PR/8/34 were obtained from NIBSC as lyophilised standard stock.

Immunizations

On day 1, seven to ten week old C57BL/6-Tg(HLA-A2.1) 1Enge/J mice (HLA-A*0201 transgenic on a C57/BL6 background, Jackson Labs) were immunised subcutaneously at the base of the tail with a 200 µl dose of the antigen preparation emulsified in IFA (Sigma). In the test group (n=14), each dose of the antigen preparation contained 60 nmol of an equimolar mixture of all six peptides (10 nmol each) whilst in the control group (n=14), each dose of the antigen preparation contained an equivalent dose of the non-relevant polypeptide.

On day 15 all animals received a booster immunisation using the same doses and route of delivery as used originally.

On Day 16 both the test and control groups were split into two equal subgroups (n=7 each; i.e. Ctrol-1, Ctrol-2, Test-1 and Test-2).

On Day 19, all animals in the Ctrol-1 and Test-1 groups received a 200 μl intraperitoneal injection of rat anti-mouse-CD8 sera (100 μg) whilst all animals in the Ctrol-2 and Test-2 groups received an equivalent injection of unrelated sera.

The following day (Day 20), all groups were challenged intranasally under anaesthesia with a large lethal dose (approximately $1.5 \times 10^7$ pfu) of Influenza A/PR/8/34.

On day 22, animals were again intraperitoneally injected with either rat anti-mouse-CD8 or unrelated sera as described above.

From day 20 all animals were monitored daily for symptoms of influenza (e.g. sneezing and pyrexia) as well as weight loss.

All animals still alive on day 27 were culled and the study was terminated.

Results

In order to assess the efficacy of the FLU-v preparation as a candidate Influenza vaccine it was desirable to set up a challenge study in NRP-v and FLU-v immunised animals using the Influenza A/PR/8/34 strain. Typically, an intranasal dose of approximately $1.5 \times 10^7$ pfu will kill non-immunised C57BL/6-Tg(HLA-A2.1)1 Enge/J mice on day 4 or 5 after challenge (data not shown).

Figure 3B:
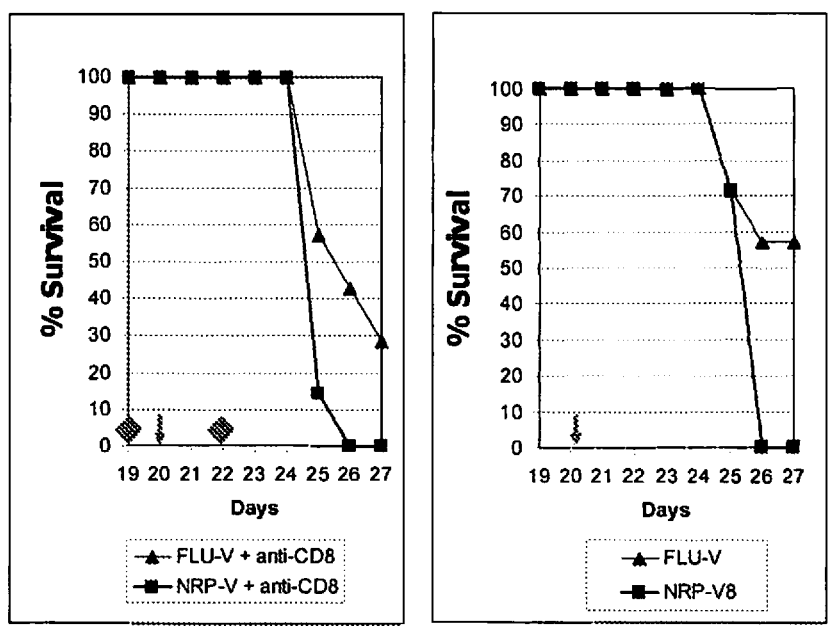

As shown in FIG. 3A, most animals immunised with either the FLU-v or NRP-v peptide preparations, but subject to CD8 depletion, had succumbed to infection by Influenza A/PR/8/34 by day 7 after intranasal challenge (71% vs 100% respectively). In contrast, as shown in FIG. 3B and in the absence of CD8 depletion, animals immunised with the FLU-v preparation showed a significant reduction ($p<0.05$) in their mortality rate compared to animals immunised with the NRP-v preparation (28% vs 100%).

The results of this study clearly indicate that vaccination with the FLU-v peptide preparation, even at a low level dose of each of its constituent active peptides (10 nmol), induces a significant level of protection against lethal challenge with Influenza. These peptides, as indicated earlier, where identified in silico primarily by their T cell reactivity within the context of Human HLA Class I. The results corroborate the fact that CD8[+] T cells stimulated by vaccination with the FLU-v peptide preparation play a significant role in conferring protection against Influenza infection.

The invention claimed is:

1. A polypeptide composition, the composition comprising an adjuvant and one or more isolated polypeptides, each of the one or more isolated polypeptides being from 8 to 50 amino acids in length,
wherein the one or more isolated polypeptides include
a polypeptide comprising an amino acid sequence with 85% or more amino acid sequence identity to SEQ ID NO: 1 or a fragment of SEQ ID NO: 1 having 8 or more consecutive amino acids from SEQ ID NO: 1,
a polypeptide comprising an amino acid sequence with 85% or more amino acid sequence identity to SEQ ID NO: 2 or a fragment of SEQ ID NO: 2 having 8 or more consecutive amino acids from SEQ ID NO: 2,
a polypeptide comprising an amino acid sequence with 85% or more amino acid sequence identity to SEQ ID NO: 3 or a fragment of SEQ ID NO: 3 having 8 or more consecutive amino acids from SEQ ID NO: 3,
a polypeptide comprising an amino acid sequence with 85% or more amino acid sequence identity to SEQ ID NO: 4 or a fragment of SEQ ID NO: 4 having 8 or more consecutive amino acids from SEQ ID NO: 4,
a polypeptide comprising an amino acid sequence with 85% or more amino acid sequence identity to SEQ ID NO: 5 or a fragment of SEQ ID NO: 5 having 8 or more consecutive amino acids from SEQ ID NO: 5, and
a polypeptide comprising an amino acid sequence with 85% or more amino acid sequence identity to SEQ ID NO: 6 or a fragment of SEQ ID NO: 6 having 8 or more consecutive amino acids from SEQ ID NO: 6,
wherein, the one or more polypeptides are immunogenic to one or more influenza strains in a vertebrate expressing a major histocompatibility complex (MHC) allele, and wherein the one or more isolated polypeptides are not a complete influenza virus protein.

2. The composition according to claim 1, wherein the one or more isolated polypeptides each comprises a cytotoxic T lymphocyte (CTL) epitope.

3. The composition according to claim 1, wherein the one or more polypeptides comprise a polypeptide comprising an amino acid sequence with 95% or more amino acid sequence identity to SEQ ID NO: 1 or a fragment of SEQ ID NO: 1 having 9 or more consecutive amino acids from SEQ ID NO: 1, a polypeptide comprising an amino acid sequence with 95% or more amino acid sequence identity to SEQ ID NO: 2 or a fragment of SEQ ID NO: 2 having 9 or more consecutive amino acids from SEQ ID NO: 2, a polypeptide comprising an amino acid sequence with 95% or more amino acid sequence identity to SEQ ID NO: 3 or a fragment of SEQ ID NO: 3 having 9 or more consecutive amino acids from SEQ ID NO: 3, a polypeptide comprising an amino acid sequence with 95% or more amino acid sequence identity to SEQ ID NO: 4 or a fragment of SEQ ID NO: 4 having 9 or more consecutive amino acids from SEQ ID NO: 4, a polypeptide comprising an amino acid sequence with 95% or more amino acid sequence identity to SEQ ID NO: 5 or a fragment of SEQ ID NO: 5 having 9 or more consecutive amino acids from SEQ ID NO: 5, and a polypeptide comprising an amino acid sequence with 95% or more amino acid sequence identity to SEQ ID NO: 6 or a fragment of SEQ ID NO: 6 having 9 or more consecutive amino acids from SEQ ID NO: 6.

4. The composition according to claim 3, wherein the one or more polypeptides comprise a polypeptide comprising an amino acid sequence with 95% or more amino acid sequence identity to SEQ ID NO: 1, a polypeptide comprising an amino acid sequence with 95% or more amino acid sequence identity to SEQ ID NO: 2, a polypeptide comprising an amino acid sequence with 95% or more amino acid sequence identity to SEQ ID NO: 3, a polypeptide comprising an amino acid sequence with 95% or more amino acid sequence identity to SEQ ID NO: 4, a polypeptide comprising an amino acid sequence with 95% or more amino acid sequence identity to SEQ ID NO: 5, and a polypeptide comprising an amino acid sequence with 95% or more amino acid sequence identity to SEQ ID NO: 6.

5. The composition according to claim 4, wherein the one or more polypeptides comprise a polypeptide comprising SEQ ID NO: 1, a polypeptide comprising SEQ ID NO: 2, a polypeptide comprising SEQ ID NO: 3, a polypeptide comprising SEQ ID NO: 4, a polypeptide comprising SEQ ID NO: 5, and a polypeptide comprising SEQ ID NO: 6.

6. The composition according to claim 5, wherein the one or more polypeptides comprise a polypeptide of SEQ ID NO: 1, a polypeptide of SEQ ID NO: 2, a polypeptide of SEQ ID NO: 3, a polypeptide of SEQ ID NO: 4, a polypeptide of SEQ ID NO: 5, and a polypeptide of SEQ ID NO: 6.

7. The composition according to claim 1, wherein each of the one or more isolated polypeptides are in an amount of 1 µg to 100 g.

8. The composition according to claim 1, wherein the adjuvant in incomplete Freund's adjuvant.

9. The composition according to claim 1, which is immunogenic to one influenza virus strains.

10. The composition according to claim 1, which is immunogenic to a plurality of influenza virus strains.

11. The composition according to claim 1, wherein the one or more influenza strains includes an influenza A strain, an influenza B strain, or both an influenza A strain and an influenza B strain.

12. A polypeptide composition, the composition comprising an adjuvant and one or more isolated polypeptides, each of the one or more isolated polypeptides being from 8 to 50 amino acids in length,
  wherein the one or more isolated polypeptides include
    a polypeptide an amino acid sequence with 85% or more amino acid sequence identity to SEQ ID NO: 1 or a fragment of SEQ ID NO: 1 having 8 or more consecutive amino acids from SEQ ID NO: 1,
    a polypeptide comprising an amino acid sequence with 85% or more amino acid sequence identity to SEQ ID NO: 3 or a fragment of SEQ ID NO: 3 having 8 or more consecutive amino acids from SEQ ID NO: 3,
    a polypeptide comprising an amino acid sequence with 85% or more amino acid sequence identity to SEQ ID NO: 4 or a fragment of SEQ ID NO: 4 having 8 or more consecutive amino acids from SEQ ID NO: 4, and
    a polypeptide comprising an amino acid sequence with 85% or more amino acid sequence identity to SEQ ID NO: 6 or a fragment of SEQ ID NO: 61 having 8 or more consecutive amino acids from SEQ ID NO: 6,
  wherein, the one or more polypeptides are immunogenic to one or more influenza strains in a vertebrate expressing a major histocompatibility complex (MHC) allele, and wherein the one or more isolated polypeptides are not a complete influenza virus protein.

13. The composition according to claim 12, wherein the one or more polypeptides comprise
  a polypeptide comprising an amino acid sequence with 95% or more amino acid sequence identity to SEQ ID NO: 1 or a fragment of SEQ ID NO: 1 having 9 or more consecutive amino acids from SEQ ID NO: 1,
  a polypeptide comprising an amino acid sequence with 95% or more amino acid sequence identity to SEQ ID NO: 3 or a fragment of SEQ ID NO: 3 having 9 or more consecutive amino acids from SEQ ID NO: 3,
  a polypeptide comprising an amino acid sequence with 95% or more amino acid sequence identity to SEQ ID NO: 4 or a fragment of SEQ ID NO: 4 having 9 or more consecutive amino acids from SEQ ID NO: 4, and
  a polypeptide comprising an amino acid sequence with 95% or more amino acid sequence identity to SEQ ID NO: 6.

14. The composition according to claim 13, wherein the one or more polypeptides comprise
  a polypeptide comprising an amino acid sequence with 95% or more amino acid sequence identity to SEQ ID NO: 1,
  a polypeptide comprising an amino acid sequence with 95% or more amino acid sequence identity to SEQ ID NO: 3,
  a polypeptide comprising an amino acid sequence with 95% or more amino acid sequence identity to SEQ ID NO: 4, and
  a polypeptide comprising an amino acid sequence with 95% or more amino acid sequence identity to SEQ ID NO: 6.

15. The composition according to claim 14, wherein the one or more polypeptides comprise
  a polypeptide comprising SEQ ID NO: 1,
  a polypeptide comprising SEQ ID NO: 3,
  a polypeptide comprising SEQ ID NO: 4, and
  a polypeptide comprising SEQ ID NO: 6.

16. The composition according to claim 15, wherein the one or more polypeptides comprise a polypeptide of SEQ ID NO: 1, a polypeptide of SEQ ID NO: 3, a polypeptide of SEQ ID NO: 4, and a polypeptide of SEQ ID NO: 6.

17. The composition according to claim 12, further comprising
  a polypeptide comprising an amino acid sequence with 85% or more amino acid sequence identity to SEQ ID NO: 2 or a fragment of SEQ ID NO: 2 having 8 or more consecutive amino acids from SEQ ID NO: 2, and
  a polypeptide comprising an amino acid sequence with 85% or more amino acid sequence identity to SEQ ID NO: 5 or a fragment of SEQ ID NO: 5 having 8 or more consecutive amino acids from SEQ ID NO: 5.

18. The composition according to claim 12, further comprising
  a polypeptide comprising an amino acid sequence with 95% or more amino acid sequence identity to SEQ ID NO: 2 or a fragment of SEQ ID NO: 2 having 9 or more consecutive amino acids from SEQ ID NO: 2, and
  a polypeptide comprising an amino acid sequence with 95% or more amino acid sequence identity to SEQ ID NO: 5 or a fragment of SEQ ID NO: 5 having 9 or more consecutive amino acids from SEQ ID NO: 5.

19. The composition according to claim 12, further comprising
  a polypeptide comprising an amino acid sequence with 95% or more amino acid sequence identity to SEQ ID NO: 2, and
  a polypeptide comprising an amino acid sequence with 95% or more amino acid sequence identity to SEQ ID NO: 5.

20. The composition according to claim 12, further comprising
  a polypeptide comprising SEQ ID NO: 2, and
  a polypeptide comprising SEQ ID NO: 5.

21. The composition according to claim 12, further comprising
  a polypeptide of SEQ ID NO: 2, and
  a polypeptide of SEQ ID NO: 5.

22. The composition according to claim 12, wherein each of the one or more isolated polypeptides are in an amount of 1 µg to 100 g.

23. The composition according to claim 12, wherein the adjuvant in incomplete Freund's adjuvant.

24. The composition according to claim 12, which is immunogenic to one influenza virus strains.

25. The composition according to claim 12, which is immunogenic to a plurality of influenza virus strains.

26. The composition according to claim 12, wherein the one or more influenza strains includes an influenza A strain, an influenza B strain, or both an influenza A strain and an influenza B strain.

* * * * *